US007794083B2

(12) United States Patent
Tsukada et al.

(10) Patent No.: US 7,794,083 B2
(45) Date of Patent: Sep. 14, 2010

(54) FUNDUS OCULI OBSERVATION DEVICE AND FUNDUS OCULI IMAGE DISPLAY DEVICE

(75) Inventors: Hisashi Tsukada, Tokyo (JP); Koki Harumoto, Tokyo (JP); Tsutomu Kikawa, Tokyo (JP); Yasufumi Fukuma, Tokyo (JP); Hiroyuki Otsuka, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 11/962,786

(22) Filed: Dec. 21, 2007

(65) Prior Publication Data

US 2008/0151187 A1 Jun. 26, 2008

(30) Foreign Application Priority Data

Dec. 22, 2006 (JP) .............................. 2006-345302

(51) Int. Cl.
*A61B 3/14* (2006.01)
*A61B 3/10* (2006.01)
(52) U.S. Cl. ...................................... 351/206; 351/221
(58) Field of Classification Search ......... 351/205–206, 351/221; 354/62
See application file for complete search history.

(56) References Cited

U.S. PATENT DOCUMENTS

| 5,975,697 | A | 11/1999 | Podoleanu et al. | |
| 2002/0051512 | A1* | 5/2002 | Toida | 378/21 |
| 2007/0216909 | A1* | 9/2007 | Everett et al. | 356/479 |

FOREIGN PATENT DOCUMENTS

| EP | 1 769 732 A2 | 4/2007 |
| EP | 1 775 545 | 4/2007 |
| EP | 1 836 952 | 9/2007 |
| JP | 2003-000543 | 1/2003 |
| JP | 2004-502483 | 1/2004 |
| JP | 2004-350849 | 12/2004 |
| JP | 2005-241464 | 9/2005 |
| JP | 2007-029460 | 2/2007 |

(Continued)

OTHER PUBLICATIONS

European Search Report dated May 27, 2008, issued in EP 07 02 4347.

(Continued)

*Primary Examiner*—Scott J Sugarman
*Assistant Examiner*—Dawayne A Pinkney
(74) *Attorney, Agent, or Firm*—Edwards Angell Palmer & Dodge LLP

(57) ABSTRACT

A fundus oculi observation device comprises: a first image forming part configured to optically acquire data and form a 2-dimensional image of a surface of a fundus oculi of an eye based on the data; a second image forming part configured to optically acquire data and form a tomographic image of the fundus oculi based on the data; a display; a controller configured to cause the display to display the 2-dimensional image and the tomographic image side by side; and a designating part configured to designate a partial region of the displayed tomographic image, wherein the controller finds a position within the 2-dimensional image corresponding to the designated partial region, and displays designated-position information in a superimposed state on the position within the 2-dimensional image.

20 Claims, 36 Drawing Sheets

FOREIGN PATENT DOCUMENTS

JP          2007-181632          7/2007

OTHER PUBLICATIONS

Jiao et al., "Simultaneous acquisition of sectional and fundus ophthalmic images with spectral-domain optical coherence tomography," Optics Express, Optical Society of America, vol. 13, No. 2, pp. 444-452, Jan. 24, 2005.

Yannuzzi et al., "Ophthalmic Fundus Imaging: Today and Beyond," American Journal of Ophthalmology, vol. 137, No. 3, pp. 511-524, Mar. 2004.

European Search Report dated Dec. 4, 2009 issued in European Patent Application No. 07 024 347.2.

* cited by examiner

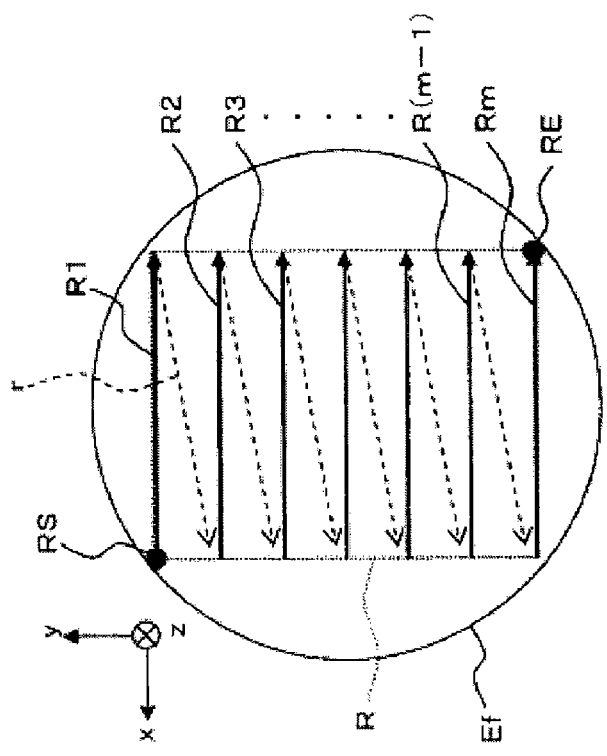
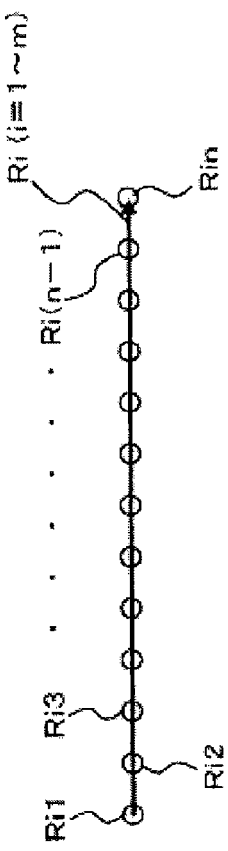
FIG. 8A
FIG. 8B

FUNDUS OCULI OBSERVATION DEVICE AND FUNDUS OCULI IMAGE DISPLAY DEVICE

BACKGROUND OF THE INVENTION

1. Field of the Invention

The present invention relates to a fundus oculi observation device and a fundus oculi image display device that are used for observing the state of a fundus oculi of an eye.

2. Description of the Related Art

As a fundus oculi observation device, a retinal camera has been widely used conventionally. FIG. 36 shows one example of the appearance of a general retinal camera used conventionally. FIG. 37 shows one example of the configuration of an optical system internally accommodated in the retinal camera (refer to Japanese Unexamined Patent Application Publication No. 2004-350849, for example). Herein, "observation" includes at least a case of observing a photographed fundus oculi image (observation of a fundus oculi with a naked eye may be included).

First, referring to FIG. 36, the appearance of a conventional retinal camera 1000 will be described. This retinal camera 1000 is provided with a platform 3 mounted on a base 2 so as to be slidable in the front and rear, right and left directions (horizontal directions). On this platform 3, an operation panel and a control lever 4 for an examiner to perform various operations are mounted.

The examiner can freely move the platform 3 on the base 2 by operating the control lever 4. On the top of the control lever 4, an operation button 4a pressed down for requiring execution of production of a fundus oculi image is mounted.

On the base 2, a post 5 is mounted standing upward. This post 5 is provided with a jaw rest 6 where a jaw of a subject is rested, and an external fixation lamp 7 serving as a light source for fixing an eye E.

On the platform 3, a main body part 8 is placed for accommodating various optical systems and control systems of the retinal camera 1000. The control system may be placed, for example, inside the base 2 or the platform 3, or in an external device such as a computer connected to the retinal camera 1000.

On the eye E side of the main body part 8, an objective lens part 8a placed facing the eye E is disposed. On the examiner's side, an eyepiece part 8b is disposed.

Further, to the main body part 8, a still camera 9 for producing a still image of the fundus oculi of the eye E and an imaging device 10 such as a TV camera for producing a still image or moving image of the fundus oculi are connected. The still camera 9 and the imaging device 10 are formed so as to be removable from the main body part 8.

As the still camera 9, in accordance with various conditions such as the purpose of an examination and a method of saving a photographed image, a digital camera equipped with a CCD, a film camera, an instant camera and the like may be interchangeably used as necessary. The main body part 8 is provided with a mounting part 8c for interchangeably mounting the still camera 9.

In a case where the still camera 9 and the imaging device 10 are of digital imaging type, it is possible to transmit and store image data into an image recording device such as a computer connected to the retinal camera 1000.

Furthermore, on the examiner's side of the main body part 8, a touch panel monitor 11 is disposed. On this touch panel monitor 11, a fundus oculi image of the eye E formed based on video signals outputted from the (digital-type) still camera 9 or imaging device 10 is displayed. Moreover, on the touch panel monitor 11, an x-y coordinate system taking the center of a screen as the origin is displayed superimposed on the fundus oculi image. When the examiner touches the screen, coordinate values corresponding to a touched position are displayed.

Next, referring to FIG. 37, the configuration of the optical system of the retinal camera 1000 will be described. The retinal camera 1000 is provided with an illumination optical system 100 that illuminates a fundus oculi Ef of the eye E, and an imaging optical system 120 that guides the illumination light reflected by the fundus oculi to the eyepiece part 8b, the still camera 9 and the imaging device 10.

The illumination optical system 100 comprises: a halogen lamp 101; a condenser lens 102; a xenon lamp 103; a condenser lens 104; exciter filters 105 and 106; a ring transparent plate 107; a mirror 108; an LCD 109; an illumination diaphragm 110; a relay lens 111; an aperture mirror 112; and an objective lens 113.

The halogen lamp 101 is an observation light source that emits continuous light. The condenser lens 102 is an optical element for converging the continuous light (observation illumination light) emitted by the halogen lamp 101 and evenly applying the observation illumination light to the eye E (fundus oculi Ef).

The xenon lamp 103 is an imaging light source that is flashed at the time of imaging of the fundus oculi Ef. The condenser lens 104 is an optical element for converging the flash light (imaging illumination light) emitted by the xenon lamp 103 and evenly applying the imaging illumination light to the fundus oculi Ef.

The exciter filters 105 and 106 are filters used at the time of fluorography of an image of the fundus oculi Ef. The exciter filters 105 and 106 can be respectively inserted into and removed from an optical path by a drive mechanism such as a solenoid. The exciter filter 105 is placed on the optical path at the time of FAG (fluorescein angiography). The exciter filter 106 is placed on the optical path at the time of ICG (indocyanine green angiography). At the time of color-imaging, both the exciter filters 105 and 106 are retracted from the optical path.

The ring transparent plate 107 is placed in a conjugating position with a pupil of the eye E, and is provided with a ring transparent part 107a taking the optical axis of the illumination optical system 100 as the center. The mirror 108 reflects the illumination light emitted by the halogen lamp 101 or xenon lamp 103, in a direction of the optical axis of the imaging optical system 120. The LCD 109 displays a fixation target (not illustrated) for fixing the eye E.

The illumination diaphragm 110 is a diaphragm member to shut out part of the illumination light in order to prevent flare and the like. This illumination diaphragm 110 is configured so as to be movable in the optical axis direction of the illumination optical system 100, and is thus capable of changing an illumination region of the fundus oculi Ef.

The aperture mirror 112 is an optical element that combines the optical axis of the illumination optical system 100 and the optical axis of the imaging optical system 120. In the center region of the aperture mirror 112, an aperture 112a is opened. The optical axis of the illumination optical system 100 and the optical axis of the imaging optical system 120 cross each other at a substantially central position of the aperture 112a. The objective lens 113 is installed in the objective lens part 8a of the main body part 8.

The illumination optical system 100 having such a configuration illuminates the fundus oculi Ef in the following manner. First, at the time of fundus oculi observation, the halogen lamp 101 is turned on and an observation illumination light is emitted. This observation illumination light is applied to the ring transparent plate 107 through the condenser lenses 102 and 104. The light passed through the ring transparent part 107a of the ring transparent plate 107 is reflected by the mirror 108 and, after passing through the LCD 109, the illumination diaphragm 110 and the relay lens 111, is reflected by the aperture mirror 112 so as to be along the optical axis direction of the imaging optical system 120. Then, the light is converged by the objective lens 113 to enter the eye E, thereby illuminating the fundus oculi Ef.

At this moment, since the ring transparent plate 107 is placed in a conjugating position with the pupil of the eye E, a ring-shaped image of the observation illumination light entering the eye E is formed on the pupil. The entering fundus oculi reflection light of the entered observation illumination light is emitted from the eye E through a central dark part of the ring-shaped image on the pupil.

On the other hand, at the time of imaging of the fundus oculi Ef, flush light is emitted from the xenon lamp 103, and the imaging illumination light is applied to the fundus oculi Ef through the same path. In the case of fluorography, either the exciter filter 105 or the exciter filter 106 is selectively placed on the optical path, depending on whether FAG imaging or ICG imaging is carried out.

The imaging optical system 120 comprises: an objective lens 113; an aperture mirror 112 (an aperture 112a thereof); an imaging diaphragm 121; barrier filters 122 and 123; a variable magnifying lens 124; a relay lens 125; an imaging lens 126; a quick return mirror 127; and an imaging media 9a. Herein, the imaging media 9a is an imaging media (a CCD, camera film, instant film or the like) for the still camera 9.

The fundus oculi reflection light of the illumination light exiting through the central dark part of the ring-shaped image formed on the pupil of the eye E enters the imaging diaphragm 121 through the aperture 112a of the aperture mirror 112. The aperture mirror 112 reflects cornea reflection light of the illumination light, and acts so as not to mix the cornea reflection light into the fundus oculi reflection light entering the imaging diaphragm 121. Consequently, generation of flare in observation images and photographed images is inhibited.

The imaging diaphragm 121 is a plate-shaped member having a plurality of circular light-transmitting parts of different sizes. The plurality of light-transmitting parts compose diaphragms with different diaphragm values (F values), and are placed alternatively on the optical path by a drive mechanism (not illustrated).

The barrier filters 122 and 123 can be inserted into and removed from the optical path by a drive mechanism such as a solenoid. In FAG imaging, the barrier filter 122 is placed on the optical path, whereas in ICG imaging, the barrier filter 123 is placed on the optical path. Further, at the time of color-imaging, both the barrier filters 122 and 123 are retracted from the optical path.

The variable magnifying lens 124 is movable in the optical axis direction of the imaging optical system 120 by a drive mechanism (not illustrated). This makes it possible to change an observation magnifying ratio and an imaging magnifying ratio, and to focus images of the fundus oculi. The imaging lens 126 is a lens that focuses the fundus oculi reflection light from the eye E onto the imaging media 9a.

The quick return mirror 127 is disposed so as to be capable of being rotated around a rotary shaft 127a by a drive mechanism (not illustrated). In a case where imaging of the fundus oculi Ef is performed with the still camera 9, the fundus oculi reflection light is guided to the imaging media 9a by springing up the quick return mirror 127 that is obliquely mounted on the optical path. Meanwhile, in a case where imaging of the fundus oculi is performed with the imaging device 10, or in a case where observation of the fundus oculi is performed with the naked eye of the examiner, the quick return mirror 127 is obliquely mounted on the optical path to upwardly reflect the fundus oculi reflection light.

The imaging optical system 120 is further provided with, for guiding the fundus oculi reflection light reflected by the quick return mirror 127, a field lens 128, a switching mirror 129, an eyepiece 130, a relay lens 131, a reflection mirror 132, an imaging lens 133, and an image pick-up element 10a. The image pick-up element 10a is an image pick-up element such as a CCD installed in the imaging device 10. On the touch panel monitor 11, a fundus oculi image Ef' imaged by the image pick-up element 10a is displayed.

The switching mirror 129 is rotatable around a rotary shaft 129a in the same manner as the quick return mirror 127. This switching mirror 129 is obliquely disposed on the optical path during observation with the naked eye, thereby reflecting and guiding the fundus oculi reflection light to the eyepiece 130.

In the case of imaging of a fundus oculi image by the imaging device 10, the switching mirror 129 is retracted from the optical path. The fundus oculi reflection light is focused on the image pick-up element 10a via the relay lens 131, the mirror 132 and the imaging lens 133, and the fundus oculi image Ef' is displayed on the touch panel monitor 11.

The retinal camera 1000 is a fundus oculi observation device used for observing the state of the surface of the fundus oculi Ef, that is, the surface of the retina. On the other hand, in the deep layer of retina, tissues such as the choroidea and sclera exist. In recent years, a device for observing these deep-layer tissues has been practically implemented (refer to Japanese Unexamined Patent Application Publications Nos. JP-A 2003-000543, JP-A 2005-241464 and JP-A 2004-502483).

Each of the fundus oculi observation devices disclosed in JP-A 2003-000543, JP-A 2005-241464 and JP-A 2004-502483 is a device to which a so-called OCT (Optical Coherence Tomography) technology is applied (referred to as an optical image measurement device, an optical coherence tomography device, and the like). Such a fundus oculi observation device is a device that splits low-coherence light into two, guides one (signal light) of the lights to the fundus oculi and the other (reference light) to a given reference object and, based on interference light obtained by superimposing the signal light passed through the fundus oculi and the reference light reflected by the reference object, forms tomographic images of the surface and deep layer tissue of the fundus oculi.

In order to ascertain, in detail, the condition of the fundus oculi (such as the presence or absence of a disease, the progression stage of a disease, the degree of therapeutic effect, and the recovery condition), it is regarded as desirable to consider the condition of the surface of the fundus oculi (surface of the retina) and the condition of deeper tissues of the fundus oculi (such as deep tissues of the retina, choroids, and sclera). However, it is difficult to ascertain, in detail, the condition of deeper tissues, by merely observing an image obtained by a retinal camera. Meanwhile, only with an image obtained through an optical image measurement device, it is difficult to grasp the state of the retina surface over a wide area.

Further, in order to comprehensively assess the condition of the fundus oculi, it is regarded as desirable to assess the state of a disease or the like by considering the condition of the surface of the fundus oculi and the condition of deeper tissues.

In order to enable the diagnoses as described above, it is necessary to present an image obtained by the retinal camera and an image obtained by the optical image measurement device in a display form in which they can be compared with each other. For example, it is desirable to facilitate the comparative work by presenting both the images simultaneously.

Further, it is desirable to display so that it is possible to easily grasp a mutual relation between a position in an image by the retinal camera and a position in an image by the optical image measurement device can be easily ascertained, making it possible to easily perform the comparative work.

In particular, when an attention site such as an involved area is specified on one image, it is often desirable to ascertain the condition of the attention site in more detail by referring to the condition of the attention site on another image.

However, with a conventional fundus oculi observation device, it has been impossible to display an image photographed by a retinal camera and an image obtained by an optical image measurement device so as to be comparable to each other and, moreover, it has been impossible to easily grasp a relation of the positions in the images. Therefore, it has been difficult to grasp in detail the state or position of a lesion site or the like of the fundus oculi.

SUMMARY OF THE INVENTION

The present invention was created to solve such problems, and an object of the present invention is to provide a fundus oculi observation device and a fundus oculi image display device that are capable of grasping in detail the state and/or position of a lesion site or the like of a fundus oculi.

In order to achieve the aforementioned object, in a first aspect of the present invention, a fundus oculi observation device comprises: a first image forming part configured to optically acquire data and form a 2-dimensional image of a surface of a fundus oculi of an eye based on the data; a second image forming part configured to optically acquire data and form a tomographic image of the fundus oculi based on the data; a display; a controller configured to cause the display to display the 2-dimensional image and the tomographic image side by side; and a designating part configured to designate a partial region of the displayed tomographic image, wherein the controller finds a position within the 2-dimensional image corresponding to the designated partial region, and displays designated-position information in a superimposed state on the position within the 2-dimensional image.

Further, in a second aspect of the present invention, a fundus oculi observation device comprises: an image forming part configured to optically acquire data, form a plurality of tomographic images of a fundus oculi of an eye based on the data, accumulate the plurality of tomographic images in a depth direction, and form an accumulated image of the fundus oculi; a display; a controller configured to cause the display to display one or more of the tomographic images and the accumulated image side by side; and a designating part configured to designate a partial region of the displayed tomographic image, wherein the controller finds a position within the accumulated image corresponding to the designated partial region, and displays designated-position information in a superimposed state on the position within the accumulated image.

Further, in a third aspect of the present invention, a fundus oculi observation device comprises: an image forming part configured to optically acquire data, form a plurality of tomographic images of a fundus oculi of an eye based on the data, and form a 3-dimensional image of the fundus oculi based on the plurality of tomographic images; a display; a controller configured to cause the display to display one or more of the tomographic images and the 3-dimensional image side by side; and a designating part configured to designate partial regions of the displayed tomographic image, wherein the controller finds a position within the 3-dimensional image corresponding to the designated partial region and display designated-position information in a superimposed state on the position within the 3-dimensional image.

Further, in a fourth aspect of the present invention, a fundus oculi image display device comprises: a storage configured to store an image representing a surface of a fundus oculi of an eye and a tomographic image of the fundus oculi; a display; a controller configured to cause the display to display the image representing the surface of the fundus oculi and the tomographic image side by side; and a designating part configured to designate a partial region of the displayed tomographic image, wherein the controller finds a position within the image representing the surface of the fundus oculi corresponding to the designated partial region, and displays the designated-position information in a superimposed state on the position within the image representing the surface of the fundus oculi.

Further, in a fifth aspect of the present invention, a fundus oculi image display device comprises: a storage configured to store a plurality of tomographic images of a fundus oculi of an eye and a 3-dimensional image of the fundus oculi based on the plurality of tomographic images; a display; a controller configured to cause the display to display the tomographic images and the 3-dimensional image side by side; and a designating part configured to designate a partial region of the displayed tomographic image, wherein the controller finds a position within the 3-dimensional image corresponding to the designated partial region, and displays designated-position information in a superimposed state on the position within the 3-dimensional image.

DESCRIPTION OF THE DRAWINGS

FIGS. 8A and 8B are schematic diagrams showing one example of a feature of scan of signal light in the preferred embodiment of the fundus oculi observation device according to the present invention. FIG. 8A shows one example of the feature of scan of signal light when a fundus oculi is seen from the incident side of the signal light with respect to an eye. FIG. 8B shows one example of a feature of arrangement of scanning points on each scanning line.

DETAILED DESCRIPTION OF THE PREFERRED EMBODIMENT

Figure 1:
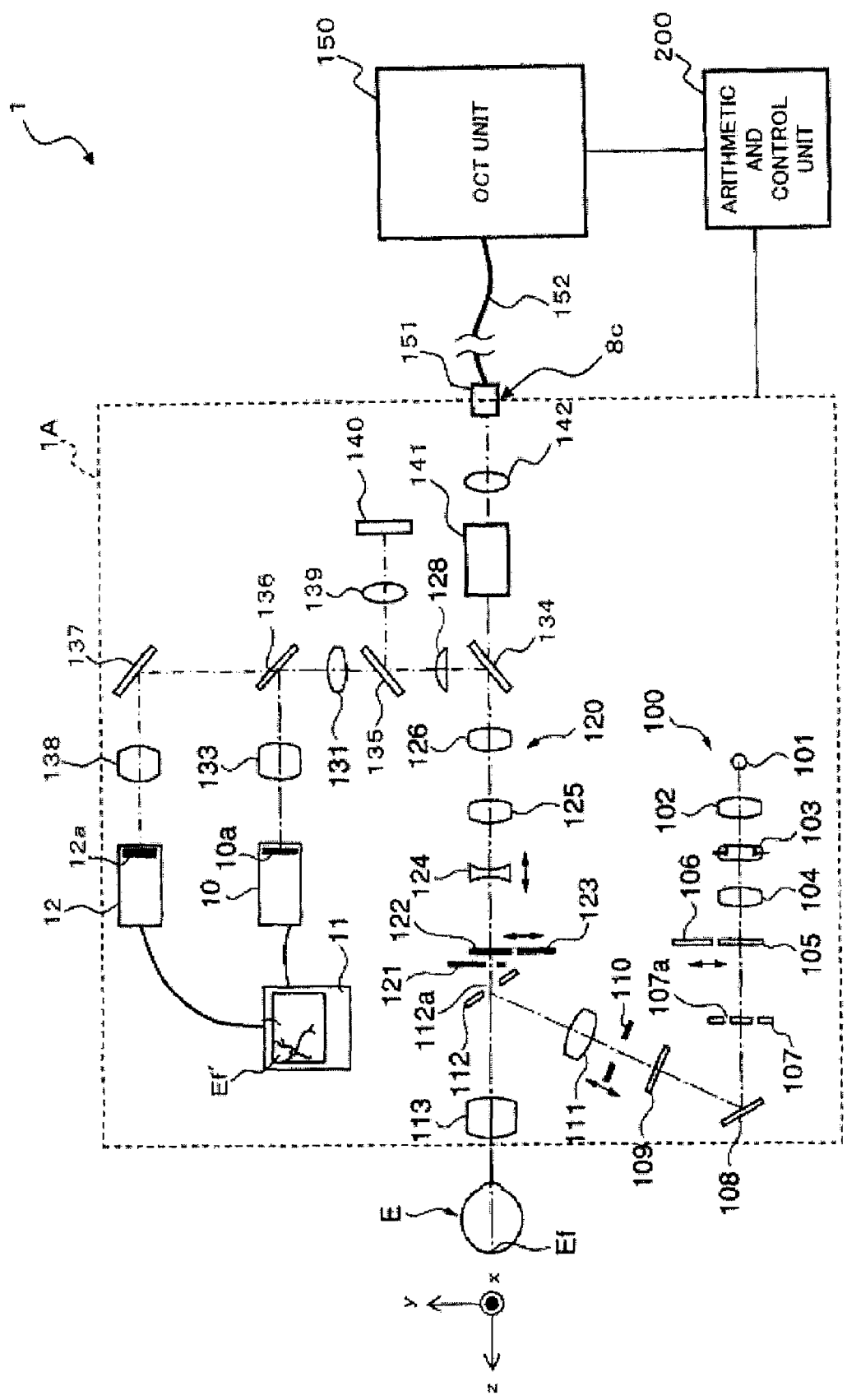
FIG. 1 is a schematic diagram showing one example of the entire configuration in a preferred embodiment of the fundus oculi observation device according to the present invention.

One example of a preferred embodiment of a fundus oculi observation device and a fundus oculi image display device according to the present invention will be described in detail referring to the drawings. Herein, the same components as the conventional ones shown in FIGS. 36 and 37 will be denoted by the same reference numerals used therein.

First Embodiment

[Configuration of Device]

Figure 2:
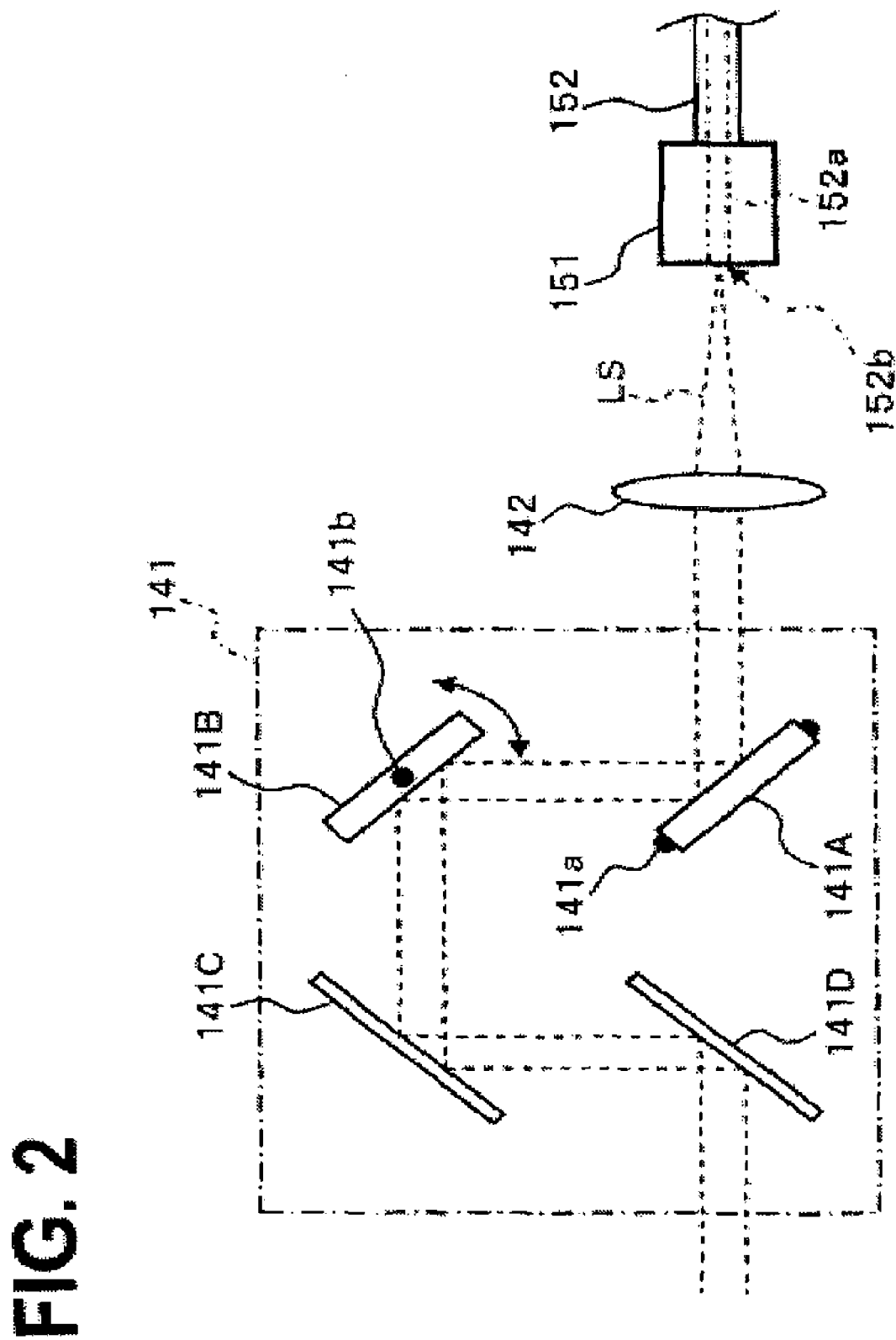
FIG. 2 is a schematic diagram showing one example of the configuration of a scanning unit installed in a retinal camera unit in the preferred embodiment of the fundus oculi observation device according to the present invention.
Figure 3:
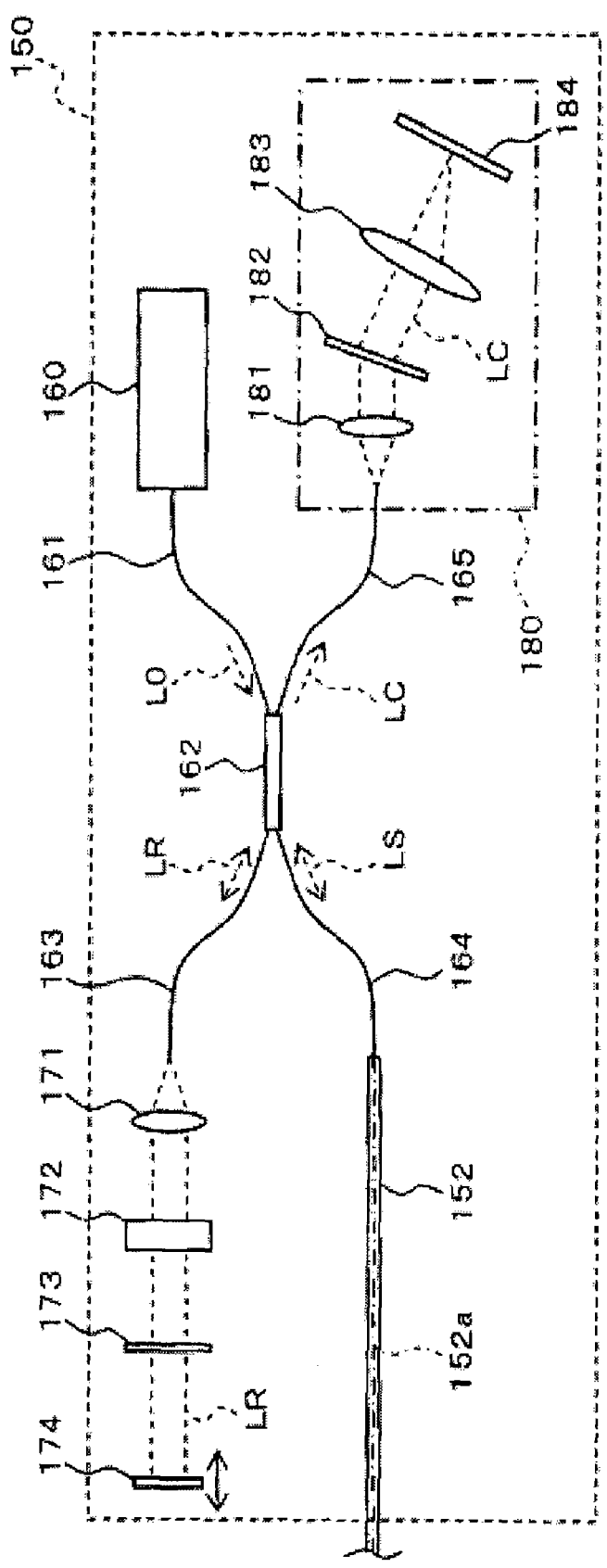
FIG. 3 is a schematic diagram showing one example of the configuration of an OCT unit in the preferred embodiment of the fundus oculi observation device according to the present invention.
Figure 4:
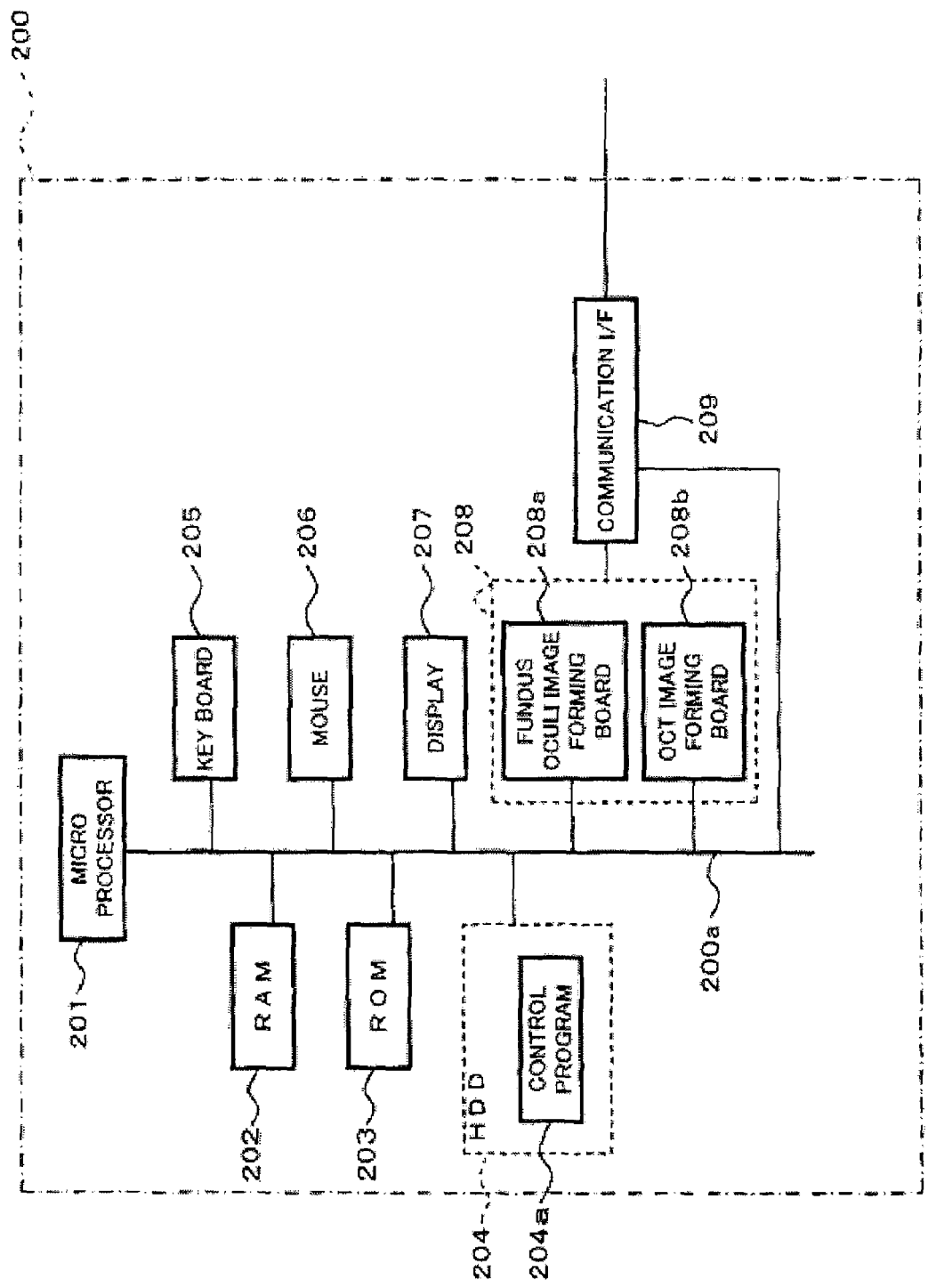
FIG. 4 is a schematic block diagram showing one example of the hardware configuration of an arithmetic and control unit in the preferred embodiment of the fundus oculi observation device according to the present invention.
Figure 5:
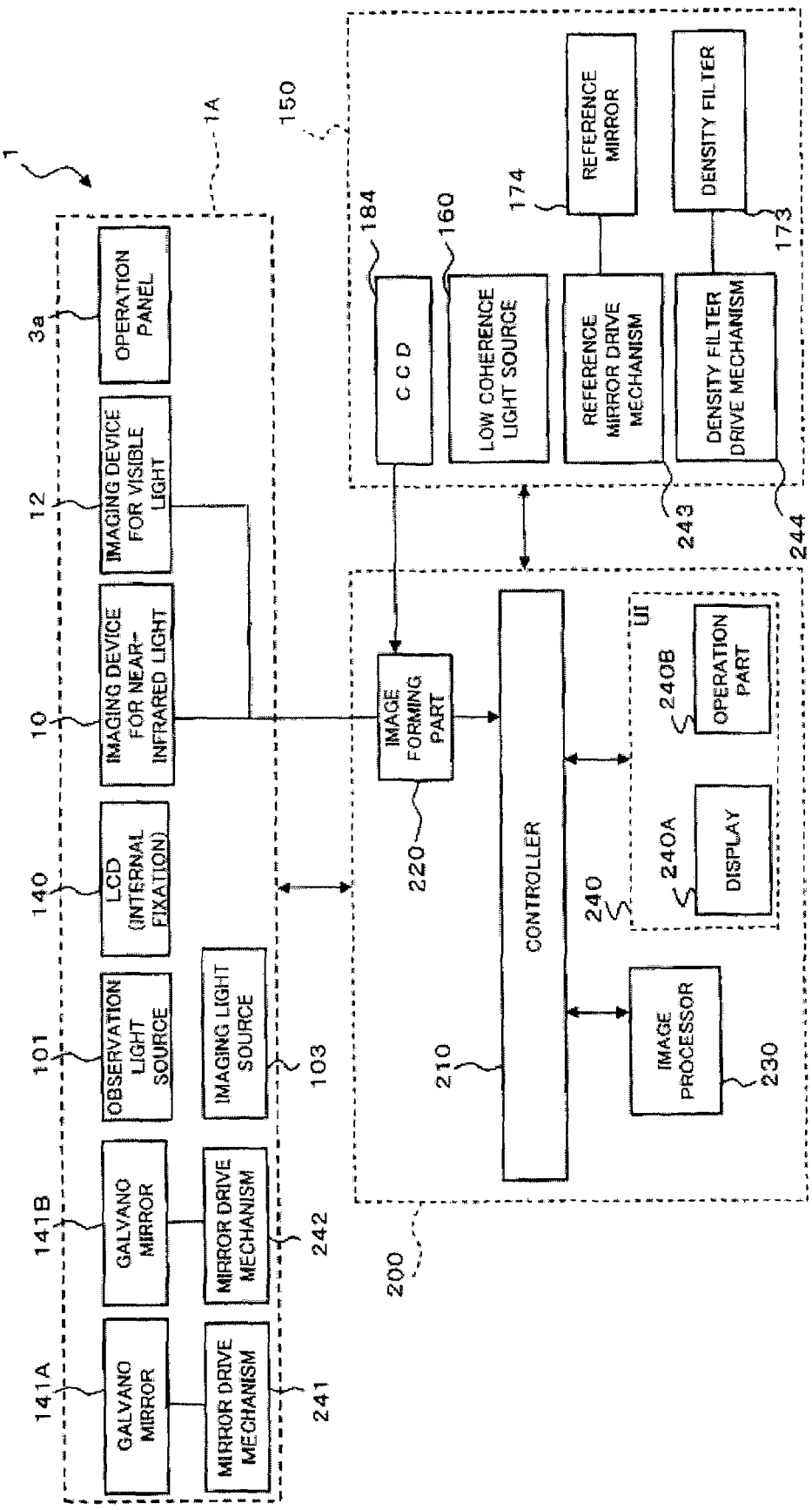
FIG. 5 is a schematic block diagram showing one example of the configuration of a control system in the preferred embodiment of the fundus oculi observation device according to the present invention.
Figure 6:
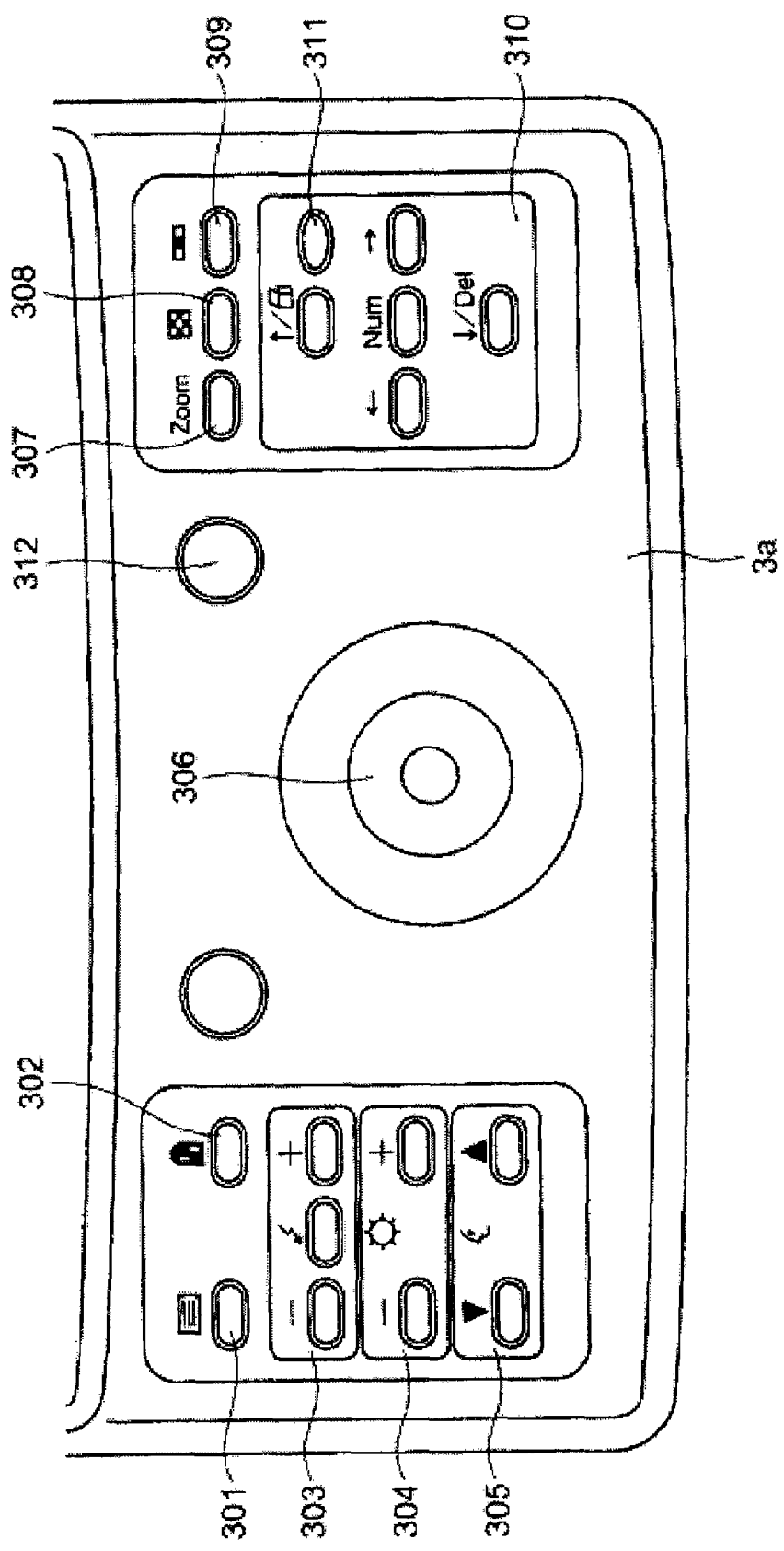
FIG. 6 is a schematic diagram showing an example of the appearance of an operation panel in the preferred embodiment of the fundus oculi observation device according to the present invention.
Figure 7:
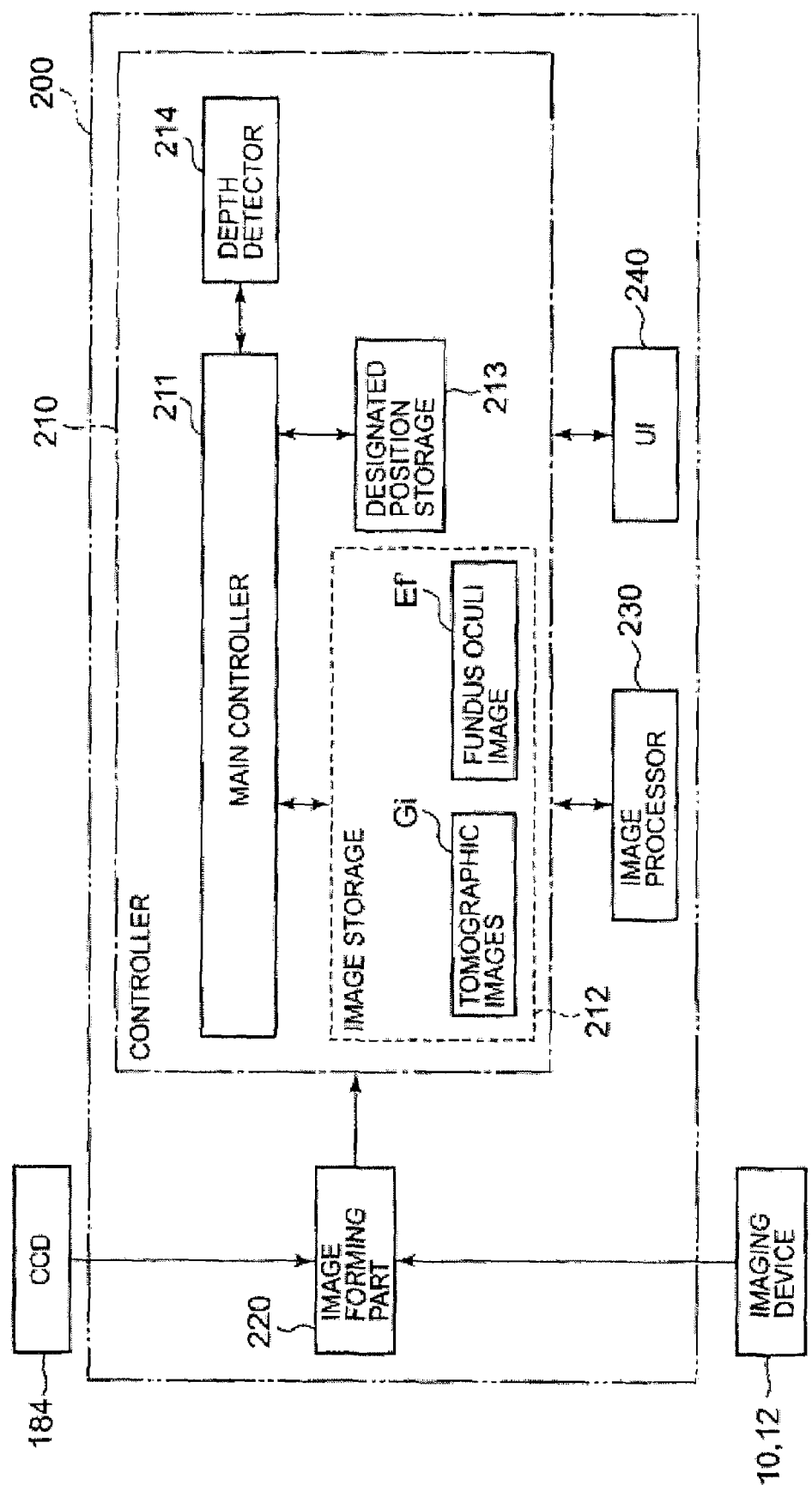
FIG. 7 is a schematic block diagram showing one example of the functional configuration of the arithmetic and control unit in the preferred embodiment of the fundus oculi observation device according to the present invention.

First, referring to FIGS. 1 through 7, the configuration of the fundus oculi observation device according to a first embodiment of the present invention will be described. FIG. 1 shows one example of the entire configuration of a fundus oculi observation device 1 according to the present embodiment. FIG. 2 shows one example of the configuration of a scanning unit 141 in a retinal camera unit 1A. FIG. 3 shows one example of the configuration of an OCT unit 150. FIG. 4 shows one example of the hardware configuration of an arithmetic and control unit 200. FIG. 5 shows one example of the configuration of a control system of the fundus oculi observation device 1. FIG. 6 shows one example of the configuration of an operation panel 3a disposed to the retinal camera unit 1A. FIG. 7 shows one example of the configuration of a control system of the arithmetic and control unit 200.

[Entire Configuration]

Figure 36:
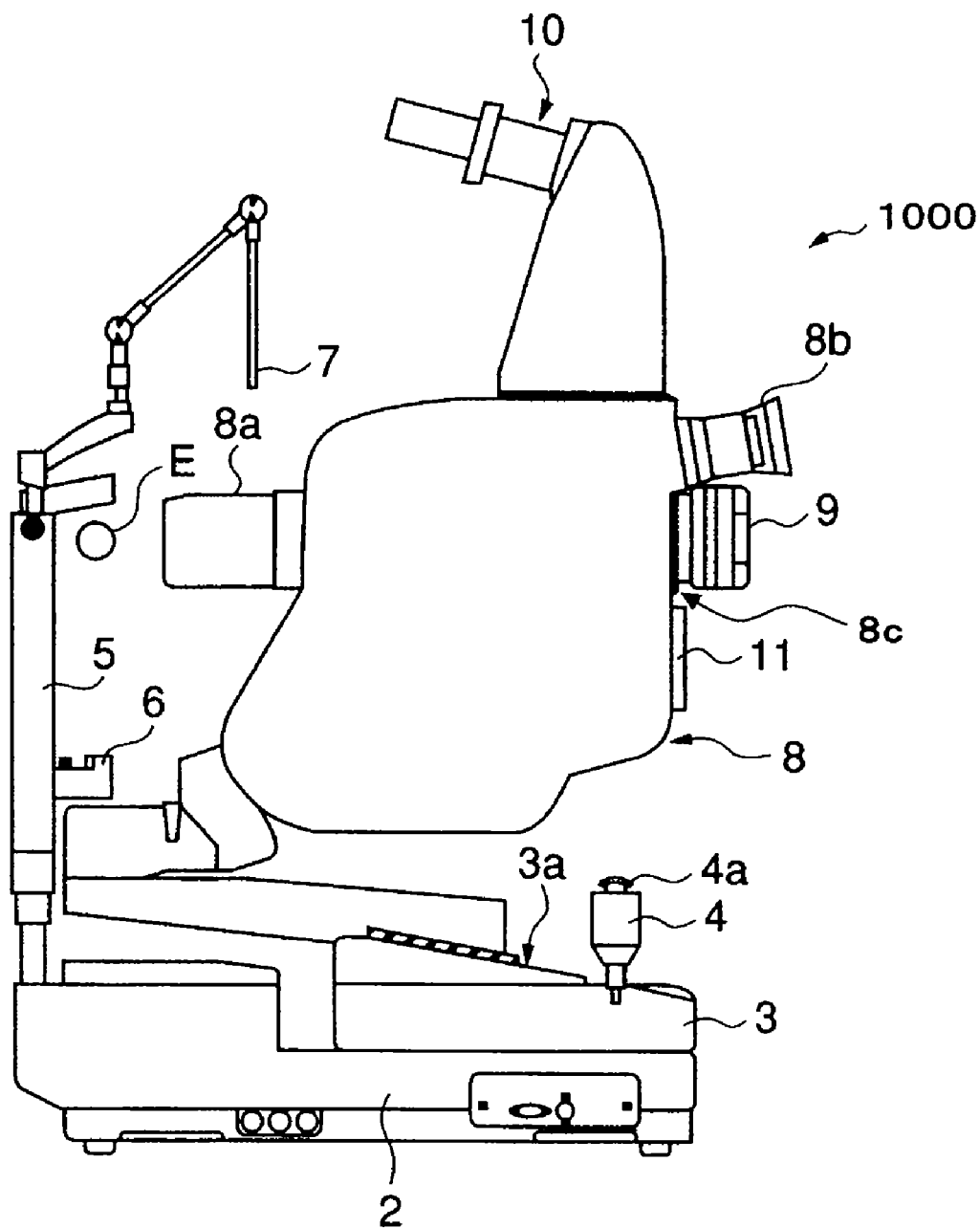
FIG. 36 is a schematic side view showing one example of the appearance of a conventional fundus oculi observation device (retinal camera).
Figure 37:
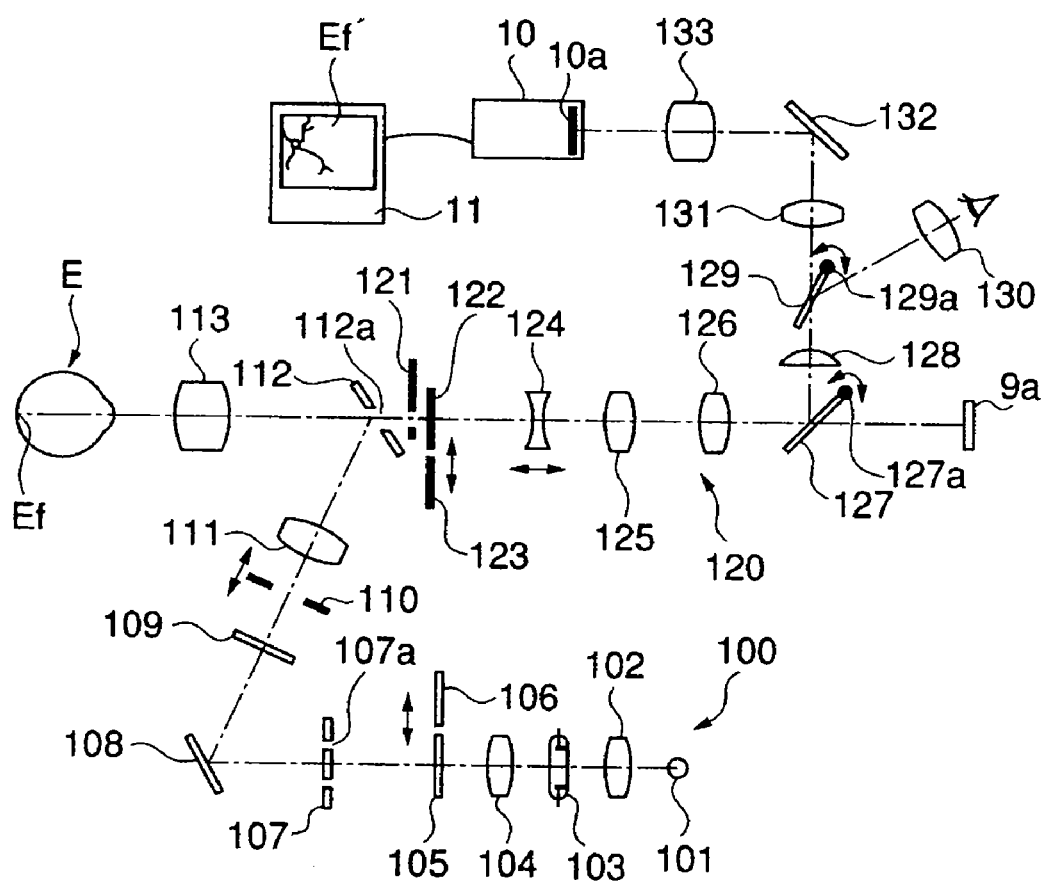
FIG. 37 is a schematic diagram showing one example of the internal configuration (optical system configuration) of a conventional fundus oculi observation device (retinal camera).

As shown in FIG. 1, the fundus oculi observation device 1 according to the present embodiment comprises: the retinal camera unit 1A that has the same function as the retinal camera of FIGS. 36 and 37; the OCT unit 150 accommodating an optical system of an optical image measurement device (OCT device); and the arithmetic and control unit 200 that executes various arithmetic processes, control processes, and the like.

To the OCT unit 150, one end of a connection line 152 is attached. To the other end of the connection line 152, a connector part 151 is attached. This connector part 151 is mounted on a mounting part (refer to the mounting part 8c shown in FIG. 36) of a case of the retinal camera unit 1A. Moreover, a conductive optical fiber runs through the inside of the connection line 152. Thus, the OCT unit 150 and the retinal camera unit 1A are optically connected via the connection line 152. The detailed configuration of the OCT unit 150 will be described later referring to FIG. 3.

[Configuration of Retinal Camera Unit]

The retinal camera unit 1A is a device configured to form a 2-dimensional image of the surface of a fundus oculi of an eye, based on optically obtained data (data detected by the imaging devices 10 and 12), and has almost the same appearance as the conventional retinal camera 1000 shown in FIG. 36. Herein, a "2-dimensional image of the surface of a fundus oculi" refers to a color or monochrome image of the surface of the fundus oculi having been photographed, a fluorescent image (a fluorescein angiography image, an indocyanine green fluorescent image, etc.), and the like. As in the conventional optical system shown in FIG. 37, the retinal camera unit 1A is provided with an illumination optical system 100 that illuminates the fundus oculi Ef of the eye E, and an imaging optical system 120 that guides the fundus oculi reflection light of the illumination light to the imaging device 10.

Although the details will be described later, the imaging device 10 in the imaging optical system 120 of the present embodiment detects the illumination light having a wavelength in the near-infrared region. Moreover, this imaging optical system 120 is further provided with the imaging device 12 for detecting the illumination light having a wavelength in the visible region. Moreover, this imaging optical system 120 guides a signal light coming from the OCT unit 150 to the fundus oculi Ef, and guides the signal light passed through the fundus oculi Ef to the OCT unit 150.

As in the conventional one, the illumination optical system 100 comprises: an observation light source 101; a condenser lens 102; an imaging light source 103; a condenser lens 104; exciter filters 105 and 106; a ring transparent plate 107; a mirror 108; an LCD (Liquid Crystal Display) 109; an illumination diaphragm 110; a relay lens 111; an aperture mirror 112; and an objective lens 113.

The observation light source 101 emits an illumination light having a wavelength of the visible region included in a range of, for example, about 400 nm thorough 700 nm. Moreover, the imaging light source 103 emits an illumination light having a wavelength of the near-infrared region included in a range of, for example, about 700 nm through 800 nm. The near-infrared light emitted from this imaging light source 103 is set so as to have a shorter wavelength than the light used by the OCT unit 150 (described later).

Further, the imaging optical system 120 comprises: an objective lens 113; an aperture mirror 112 (an aperture 112a thereof); an imaging diaphragm 121; barrier filters 122 and 123; a variable magnifying lens 124; a relay lens 125; an imaging lens 126; a dichroic mirror 134; a field lens 128; a half mirror 135; a relay lens 131; a dichroic mirror 136; an imaging lens 133; the imaging device 10 (image pick-up element 10a); a reflection mirror 137; an imaging lens 138; the imaging device 12 (image pick-up element 12a); a lens 139; and an LCD 140.

The imaging optical system 120 according to the present embodiment is different from the conventional imaging optical system 120 shown in FIG. 37 in that the dichroic mirror 134, the half mirror 135, the dichroic mirror 136, the reflection mirror 137, the imaging lens 138, the lens 139 and the LCD 140 are disposed.

The dichroic mirror 134 is configured to reflect the fundus oculi reflection light (having a wavelength included in a range of about 400 nm through 800 nm) of the illumination light from the illumination optical system 100, and transmit a signal light LS (having a wavelength included in a range of, for example, about 800 nm through 900 nm; described later) from the OCT unit 150.

Further, the dichroic mirror 136 is configured to transmit the illumination light having a wavelength of the visible region from the illumination optical system 100 (a visible light having a wavelength of about 400 nm through 700 nm emitted from the observation light source 101), and reflect the illumination light having a wavelength of the near-infrared region (a near-infrared light having a wavelength of about 700 nm through 800 nm emitted from the imaging light source 103).

On the LCD 140, a fixation target (internal fixation target) or the like for fixing the eye E is displayed. The light from this LCD 140 is reflected by the half mirror 135 after being converged by the lens 139, and is reflected by the dichroic mirror 136 through the field lens 128. Then, the light passes through the imaging lens 126, the relay lens 125, the variable magnifying lens 124, the aperture mirror 112 (aperture 112a thereof), the objective lens 113 and the like, and enters the eye E. Consequently, an internal fixation target or the like is projected in the fundus oculi Ef of the eye E.

The image pick-up element 10a is an image pick-up element such as a CCD and a CMOS installed in the imaging device 10 such as a TV camera, and is particularly used for detecting light having a wavelength of the near-infrared region (that is, the imaging device 10 is an infrared TV camera for detecting near-infrared light). The imaging device 10 outputs video signals as a result of detection of the near-infrared light.

A touch panel monitor 11 displays a 2-dimensional image (a fundus oculi image Ef′) of the surface of the fundus oculi Ef, based on the video signals. The video signals are sent to the arithmetic and control unit 200, and the fundus oculi image is displayed on the display (described later).

At the time of imaging of the fundus oculi by the imaging device 10, for example, the illumination light emitted from the imaging light source 103 of the illumination optical system 100 and having a wavelength of the near-infrared region is used.

On the other hand, the image pick-up element 12a is an image pick-up element such as a CCD and a CMOS installed in the imaging device 12 such as a TV camera, and is particularly used for detecting light having a wavelength of the visible region (that is, the imaging device 12 is a TV camera for detecting visible light). The imaging device 12 outputs video signals as a result of detection of the visible light.

The touch panel monitor 11 displays a 2-dimensional image (fundus oculi image Ef) of the surface of the fundus oculi Ef, based on the video signals. The video signals are sent to the arithmetic and control unit 200, and the fundus oculi image Ef is displayed on the display (described later).

At the time of imaging of the fundus oculi by the imaging device 12, for example, the illumination light emitted from the observation light source 101 of the illumination optical system 100 and having a wavelength of the visible region is used.

The imaging optical system 120 according to the present embodiment is provided with 150 a scanning unit 141 and a lens 142. The scanning unit 141 includes a component for scanning at an application position of the fundus oculi Ef with light emitted from the OCT unit (signal light LS; described later).

The lens 142 makes the signal light LS guided from the OCT unit 150 through the connection line 152 enter the scanning unit 141 in the form of a parallel light flux. Moreover, the lens 142 acts so as to converge the fundus oculi reflection light of the signal light LS passed through the scanning unit 141.

FIG. 2 shows one example of a specific configuration of the scanning unit 141. The scanning unit 141 comprises Galvano mirrors 141A and 141B, and reflection mirrors 141C and 141D.

The Galvano mirrors 141A and 141B are reflection mirrors disposed so as to be rotatable about rotary shafts 141a and 141b, respectively. The Galvano mirrors 141A and 141B are rotated about the rotary shafts 141a and 141b, respectively, by a drive mechanism described later (mirror drive mechanisms 241 and 242 shown in FIG. 5), whereby the orientations of reflection surfaces thereof (faces reflecting the signal light LS), namely, the positions of the Galvano mirrors 141A and 141B are changed, respectively.

The rotary shafts 141a and 141b are arranged so as to be orthogonal to each other. In FIG. 2, the rotary shaft 141a of the Galvano mirror 141A is arranged in parallel to the paper face of this figure, whereas the rotary shaft 141b of the Galvano mirror 141B is arranged so as to be orthogonal to the paper face of this figure.

That is, the Galvano mirror 141B is formed so as to be rotatable in the directions indicated by an arrow pointing in both directions in FIG. 2, whereas the Galvano mirror 141A is formed so as to be rotatable in the directions orthogonal to the arrow pointing in both the directions. Consequently, the pair of Galvano mirrors 141A and 141B act so as to change the reflecting directions of the signal light LS to directions orthogonal to each other. As seen from FIGS. 1 and 2, scan with the signal light LS is performed in the x direction when the Galvano mirror 141A is rotated, and scan with the signal light LS is performed in the y direction when the Galvano mirror 141B is rotated.

The signal lights LS reflected by the Galvano mirrors 141A and 141B are reflected by reflection mirrors 141C and 141D, thereby traveling in the same directions as having entered into the Galvano mirror 141A.

As described before, the conductive optical fiber 152a runs through the inside of the connection line 152, and an end face 152b of the optical fiber 152a is arranged facing the lens 142. The signal light LS emitted from this end face 152b travels while expanding its beam diameter toward the lens 142. The light is converged into a parallel light flux by this lens 142. On the contrary, the signal light LS passed through the fundus oculi Ef is converged toward the end face 152b by the lens 142, and guided to the optical fiber 152a.

Configuration of OCT Unit

Next, the configuration of the OCT unit 150 will be described referring to FIG. 3. The OCT unit 150 shown in FIG. 3 is a device configured to form a tomographic image of the fundus oculi based on optically obtained data (data detected by a CCD 184 described later).

The OCT unit 150 has almost the same optical system as the conventional optical image measurement device. That is, the OCT unit 150 has: an interferometer that splits the light emitted from the light source into a reference light and a signal light and generates interference light by superposing the reference light passed through a reference object and the signal light passed through a measurement object (fundus oculi Ef); and a part configured to detect this interference light and output signals as the result of the detection (detection signals) toward the arithmetic and control unit 200. The arithmetic and control unit 200 forms a tomographic image of the measurement object (fundus oculi Ef), by analyzing the detection signals.

A low coherence light source 160 is composed of a broadband light source, such as a super luminescent diode (SLD) and a light emitting diode (LED), configured to emit a low coherence light L0. This low coherence light L0 is, for example, a light that has a wavelength of the near-infrared region and has a time-wise coherence length of approximately several tens of micrometers.

The low coherence light L0 has a longer wavelength than the illumination light (wavelength: about 400 nm through 800 nm) of the retinal camera unit 1A, for example, a wavelength included in a range of about 800 nm through 900 nm.

The low coherence light L0 emitted from the low coherence light source 160 is guided to an optical coupler 162 through an optical fiber 161 composed of, for example, a single mode fiber or a PM (Polarization maintaining) fiber. The optical coupler 162 splits this low coherence light L0 into a reference light LR and the signal light LS.

Although the optical coupler 162 acts as both a part (splitter) for splitting light and a part (coupler) for superposing lights, it will be herein referred to as an "optical coupler" idiomatically.

The reference light LR generated by the optical coupler 162 is guided by an optical fiber 163 composed of a single mode fiber or the like, and emitted from the end face of the fiber. The emitted reference light LR is converged into a parallel light flux by a collimator lens 171, passed through a glass block 172 and a density filter 173, and then reflected by a reference mirror 174 (reference object).

The reference light LR reflected by the reference mirror 174 is converged to the fiber end face of the optical fiber 163 by the collimator lens 171 again through the density filter 173 and the glass block 172. The converged reference light LR is guided to the optical coupler 162 through the optical fiber 163.

The glass block 172 and the density filter 173 act as a delaying part for making the optical path lengths (optical distances) of the reference light LR and the signal light LS coincide, and also as a dispersion correction part for making the dispersion characteristics of the reference light LR and the signal light LS coincide.

Further, the density filter 173 also acts as a dark filter for reducing the amount of the reference light, and is composed of a rotating ND (neutral density) filter, for example. This density filter 173 acts so as to change the reduction amount of the reference light LR by being rotary driven by a drive mechanism including a drive unit such as a motor (a density filter drive mechanism 244 described later; refer to FIG. 5). Consequently, it is possible to change the amount of the reference light LR contributing to generation of the interference light LC.

Furthermore, the reference mirror 174 is configured so as to move in the traveling direction (the direction of the arrow pointing both sides shown in FIG. 3) of the reference light LR. As a result, the optical path length of the reference light LR according to the axial length of the eye E, etc. is ensured. The reference mirror 174 is moved by a drive mechanism (a reference mirror driving mechanism 243 described later; refer to FIG. 5) including a driving part such as a motor.

On the other hand, the signal light LS generated by the optical coupler 162 is guided to the end of the connection line 152 through an optical fiber 164 composed of a single mode fiber or the like. The conductive optical fiber 152a runs inside the connection line 152. Herein, the optical fiber 164 and the optical fiber 152a may be composed of a single optical fiber, or may be jointly formed by connecting the end faces of the respective fibers. In either case, it is sufficient as far as the optical fiber 164 and 152a are configured to be capable of transferring the signal light LS between the retinal camera unit 1A and the OCT unit 150.

The signal light LS is guided through the inside of the connection line 152 and led to the retinal camera unit 1A. Then, the signal light LS enters into the eye E through the lens 142, the scanning unit 141, the dichroic mirror 134, the imaging lens 126, the relay lens 125, the variable magnifying lens 124, the imaging diaphragm 121, the aperture 112a of the aperture mirror 112, and the objective lens 113. The barrier filter 122 and 123 are retracted from the optical path in advance, respectively, when the signal light LS is made to enter the eye E.

The signal light LS having entered the eye E forms an image on the fundus oculi (retina) Ef and is then reflected. At this moment, the signal light LS is not only reflected on the surface of the fundus oculi Ef, but also scattered at the refractive index boundary after reaching the deep area of the fundus oculi Ef. As a result, the signal light LS passed through the fundus oculi Ef is a light containing information reflecting the state of the surface of the fundus oculi Ef and information reflecting the state of backscatter at the refractive index boundary of the deep area tissue of the fundus oculi Ef. This light may be simply referred to as "fundus oculi reflection light of the signal light LS."

The fundus oculi reflection light of the signal light LS travels reversely on the above path within the retinal camera unit 1A to be converged at the end face 152b of the optical fiber 152a, enters into the OCT unit 150 through the optical fiber 152a, and returns to the optical coupler 162 through the optical fiber 164.

The optical coupler 162 superimposes the signal light LS returning through the fundus oculi Ef and the reference light LR reflected by the reference mirror 174, thereby generating the interference light LC. The generated interference light LC is guided into a spectrometer 180 through an optical fiber 165 composed of a single mode fiber or the like.

Herein, although a Michelson-type interferometer is adopted in the present embodiment, for instance, a Mach Zender type, etc. and any type of interferometer may be adopted appropriately.

The spectrometer 180 comprises a collimator lens 181, a diffraction grating 182, an image-forming lens 183, and a CCD 184. The diffraction grating 182 in the present embodiment is a transmission-type diffraction grating that transmits light; however, needless to say, a reflection-type diffraction grating that reflects light may also be used. Moreover, needless to say, it is also possible to adopt, in place of the CCD 184, other photo-detecting elements.

The interference light LC having entered the spectrometer 180 is split (resolved into spectra) by the diffraction grating 182 after converged into a parallel light flux by the collimator lens 181. The split interference light LC forms an image on the image pick-up surface of the CCD 184 by the image-forming lens 183. The CCD 184 receives the interference light LC and converts to electrical detection signals, and outputs the detection signals to the arithmetic and control unit 200.

[Configuration of Arithmetic and Control Unit]

Next, the configuration of the arithmetic and control unit 200 will be described. This arithmetic and control unit 200 corresponds to one example of the "fundus oculi image display device" according to the present invention.

The arithmetic and control unit 200 performs a process of analyzing the detection signals inputted from the CCD 184 of the spectrometer 180 of the OCT unit 150, and forming tomographic images of the fundus oculi Ef of the eye E. A technique for this analysis is the same as a conventional technique for the Fourier domain OCT.

Further, the arithmetic and control unit 200 performs a process of forming (image data of) a 2-dimensional image showing the state of the surface (retina) of the fundus oculi Ef, based on the video signals outputted from the imaging devices 10 and 12 of the retinal camera unit 1A.

Furthermore, the arithmetic and control unit 200 executes control of each part of the retinal camera unit 1A and the OCT unit 150.

Control of the retinal camera unit 1A is, for example: control of emission of illumination light by the observation light source 101 or the imaging light source 103; control of insertion/retraction operations of the exciter filters 105 and 106 or the barrier filters 122 and 123 to/from the optical path; control of the operation of a display device such as the LCD 140; control of shift of the illumination diaphragm 110 (control of the diaphragm value); control of the diaphragm value of the imaging diaphragm 121; and control of shift of the variable magnifying lens 124 (control of the magnification). Moreover, the arithmetic and control unit 200 executes control of the operation of the Galvano mirrors 141A and 141B inside the scanning unit 141 (operation of changing the directions of the reflection faces).

Further, control of the OCT unit 150 is, for example: control of emission of the low coherence light L0 by the low coherence light source 160; control of shift of the reference mirror 174; control of the rotary operation of the density filter 173 (operation of changing the reduction amount of the reference light LR); and control of the accumulated time of the CCD 184.

One example of the hardware configuration of the arithmetic and control unit 200 that acts as described above will be described referring to FIG. 4.

The arithmetic and control unit 200 is provided with the same hardware configuration as that of a conventional computer. To be specific, the arithmetic and control unit 200 comprises: a microprocessor 201 (CPU, MPU, etc.), a RAM202, a ROM203, a hard disk drive (HDD) 204, a keyboard 205, a mouse 206, a display 207, an image forming board 208, and a communication interface (I/F) 209. These parts are connected via a bus 200a.

The microprocessor 201 executes operations characteristic to the present embodiment, by loading a control program 204a stored in the hard disk drive 204, onto the RAM 202.

Further, the microprocessor 201 executes control of each part of the device described above, various arithmetic processes, etc. Moreover, the microprocessor 201 executes control of each part of the device corresponding to an operation signal from the keyboard 205 or the mouse 206, control of a display process by the display 207, and control of a transmission/reception process of various data, control signals and so on by the communication interface 209.

The keyboard 205, the mouse 206 and the display 207 are used as user interfaces in the fundus oculi observation device 1. The keyboard 205 is used as, for example, a device for typing letters, figures, etc. The mouse 206 is used as a device for performing various input operations to the display screen of the display 207.

Further, the display 207 is any display device composed of an LCD, a CRT (Cathode Ray Tube) display or the like. The display 207 displays various images of the fundus oculi Ef formed by the fundus oculi observation device 1, and displays various screens such as an operation screen and a set-up screen.

The user interface of the fundus oculi observation device 1 is not limited to the above configuration, and may be configured by using any user interface having a function of displaying and outputting various information, and a function of inputting various information and operating the device, such as a track ball, a control lever, a touch panel type of LCD, and a control panel for opthalmology examinations.

The image forming board 208 is a dedicated electronic circuit for a process of forming (image data of) images of the fundus oculi Ef of the eye E. This image forming board 208 is provided with a fundus oculi image forming board 208a and an OCT image forming board 208b.

The fundus oculi image forming board 208a is a dedicated electronic circuit that operates to form image data of fundus oculi images based on the video signals from the imaging device 10 and the imaging device 12 of the retinal camera unit 1A.

Further, the OCT image forming board 208b is a dedicated electronic circuit that operates to form image data of tomographic images of the fundus oculi Ef, based on the detection signals from the CCD 184 of the spectrometer 180 in the OCT unit 150.

By providing the image forming board 208, it is possible to increase the processing speed for forming image data of fundus oculi images and tomographic images.

The communication interface 209 performs a process of sending control signals from the microprocessor 201, to the retinal camera unit 1A or the OCT unit 150. Moreover, the communication interface 209 performs a process of receiving video signals from the imaging devices 10 and 12 of the retinal camera unit 1A and detection signals from the CCD 184 of the OCT unit 150, and inputting the signals to the image forming board 208. At this time, the communication interface 209 operates to input the video signals from the imaging devices 10 and 12, to the fundus oculi image forming board 208a, and input the detection signal from the CCD 184, to the OCT image forming board 208b.

Further, in a case where the arithmetic and control unit 200 is connected to a network such as a LAN (Local Area Network) and the Internet, it is possible to configure so as to be capable of data communication via the network, by providing the communication interface 209 with a network adapter like a LAN card or communication equipment like a modem. In this case, by mounting a server accommodating the control program 204a on the network, and at the same time, configuring the arithmetic and control unit 200 as a client terminal of the server, it is possible to cause the fundus oculi observation device 1 to execute the operation according to the present invention.

[Configuration of Control System]

Next, the configuration of the control system of the fundus oculi observation device 1 will be described referring to FIG. 5 through FIG. 7. FIG. 5 is a block diagram showing a part related to the operations and processes according to the present invention particularly selected from among constituents composing the fundus oculi observation device 1. FIG. 6 shows one example of the configuration of the operation panel 3a disposed to the retinal camera unit 1A. FIG. 7 is a block diagram showing a detailed configuration of the arithmetic and control unit 200.

(Controller)

The control system of the fundus oculi observation device 1 is configured mainly having a controller 210 of the arithmetic and control unit 200 shown in FIG. 5. The controller 210 comprises the microprocessor 201, the RAM202, the ROM203, the hard disk drive 204 (control program 204a), and the communication interface 209.

The controller 210 executes the aforementioned controlling processes through the microprocessor 201 operating based on the control program 204a. In specific, for the retinal camera unit 1A, the controller 210 performs control of the mirror drive mechanisms 241 and 242 for changing the positions of the Galvano mirrors 141A and 141B, control of the display operation of the internal fixation target by the LCD 140, etc.

Further, for the OCT unit 150, the controller 210 performs control of the low coherence light source 160 and the CCD 184, control of the density filter drive mechanism 244 for rotating the density filter 173, control of the reference mirror drive mechanism 243 for moving the reference mirror 174 in the traveling direction of the reference light LR, etc.

Furthermore, the controller 210 performs control for causing the display 240A of the user interface (UI) 240 to display two kinds of images photographed by the fundus oculi observation device 1: that is, a 2-dimensional image (fundus oculi image Ef') of the surface of the fundus oculi Ef obtained by the retinal camera unit 1A, and a tomographic image of the fundus oculi Ef formed based on the detection signals obtained by the OCT unit 150. These images may be displayed on the display 240A separately, or may be displayed side by side simultaneously.

In the controller 210, as shown in FIG. 7, a main controller 211, an image storage 212, a designated-position storage 213, and a depth detector 214 are provided. The main controller 211 executes the previously described various control processes by the controller 210. Furthermore, the main controller 211 executes processes for storing information in the image storage 212 or in the designated-position storage 213, and processes for reading out the information stored in the image storage 212 or in the designated-position storage 213.

The image storage 212 stores images formed by the image-forming part 220. The image storage 212 stores (image data of) images such as a tomographic image Gi (i=1 to m) along each scanning line Ri, or the fundus oculi image Ef. The image storage 212 functions as one example of the "storage" in the fundus oculi image display device according to the present invention or in a computer, and comprises, for example, a hard disk drive 204.

The designated-position storage 213 stores the position (coordinate values) of a region designated by an examiner in a tomographic image displayed on the display 240A, and comprises, for example, a RAM 202 and/or a hard disk drive 204.

The depth detector 214 detects the depth of the region designated by the examiner in the tomographic image displayed on the display 240A, and functions as one example of the "depth detector" in the present invention. One example of the operations of the depth detector 214 is described. The depth detector 214 specifies an image region corresponding to the fundus oculi surface by analyzing the pixel values (brightness values) of a tomographic image, and also finds the distance (depth) from the fundus oculi surface to the designated region by counting the number of pixels in the depth direction (z-direction) from the image region (surface) to the region designated by the examiner. The depth detector 214 comprises the microprocessor 201 operating based on the control program 204a.

The controller 210 configured as described above functions as one example of the "controller" according to the present invention.

(Image Forming Part)

An image forming part 220 performs a process of forming image data of the fundus oculi image based on the video signals from the imaging devices 10 and 12 of the retinal camera unit 1A. Moreover, the image forming part 220 performs a process of forming image data of the tomographic images of the fundus oculi Ef based on the detection signals from the CCD 184 of the OCT unit 150. The imaging forming part 220 comprises the imaging forming board 208 and the communication interface 209. In this specification, "image" may be identified with "image data" corresponding thereto.

(Image Processor)

The image processor 230 applies various image processing to image data of images formed by the image forming part 220. For example, the image processor 230 executes a process of forming image data of a 3-dimensional image of the fundus oculi Ef based on the tomographic images corresponding to the detection signal from the OCT unit 150, and various correction processes such as brightness correction and dispersion correction of the images.

Herein, image data of a 3-dimensional image is image data made by assigning pixel values to each of a plurality of voxels arranged 3-dimensionally, and is referred to as volume data, voxel data, and the like. When displaying an image based on volume data, the image processor 230 operates to apply a rendering process (such as volume rendering and MIP (Maximum Intensity Projection)) to this volume data and form image data of a pseudo 3-dimensional image seen from a specified viewing direction. On a display device such as the display 207, the pseudo 3-dimensional image based on the image data is displayed.

The image processor 230 comprises the microprocessor 201, the RAM 202, the ROM 203, and the hard disk drive 204 (control program 204a).

A "first image forming part" according to the present invention comprises each part of the retinal camera unit 1A for capturing 2-dimensional images of the surface of the fundus oculi Ef, and the image forming part 220 (fundus oculi image forming board 208a). Moreover, a "second image forming part" according to the present invention comprises each part of the retinal camera unit 1A for capturing tomographic images of the fundus oculi Ef, the OCT unit 150, the image forming part 220 (OCT image forming board 208b), and the image processor 230.

(User Interface)

The user interface (UI) 240 comprises the display 240A and an operation part 240B. The display 240A is composed of a display device such as the display 207, and functions as one example of the "display" according to the present invention. Further, the operation part 240B is composed of an input device or an operation device such as the keyboard 205 and the mouse 206, and functions as one example of the "operation part" according to the present invention. Herein, the "operating part" functions as one example of the "designating part" according to the present invention.

(Operation Panel)

The operation panel 3a of the retinal camera unit 1A will be described below. As shown in FIG. 36, this operation panel 3a is arranged on the platform 3 of the retinal camera unit 1A, for example.

The operation panel 3a according to the present embodiment is, different from the conventional configuration described in Background of the Invention, provided with an operating part used to instruct an operation for capturing an image of the surface of the fundus oculi Ef and the vicinity thereof, and an operating part used to instruct an operation for capturing a tomographic image of the fundus oculi Ef (in the conventional configuration, only the former operating part is provided).

In the present embodiment, placement of the operation panel 3a makes it possible to execute an operation for capturing various images in the same manner as when operating a conventional retinal camera.

As shown in FIG. 6, the operation panel 3a is provided with, for example, a menu switch 301, a split switch 302, an imaging light amount switch 303, an observation light amount switch 304, a jaw holder switch 305, a photographing switch 306, a zoom switch 307, an image switching switch 308, a fixation target switching switch 309, a fixation target position adjusting switch 310, a fixation target size switching switch 311, and a mode switching knob 312.

The menu switch 301 is a switch operated to display a certain menu screen for a user to select and designate various menus (such as an imaging menu for imaging a 2-dimensional image of the surface of the fundus oculi Ef, a tomographic image and the like, and a setting menu for inputting various settings).

When this menu switch 301 is operated, the operation signal is inputted to the controller 210. The controller 210 causes the touch panel monitor 11 or the display 240A to display a menu screen, in response to the input of the operation signal. A controller (not shown) may be provided in the retinal camera unit 1A, whereby the controller causes the touch panel monitor 11 to display the menu screen.

The split switch 302 is a switch operated to switch the light on and off of the split bright line for focusing (e.g., see JP Patent laid-open No. H9-66031. Also referred to as split target, split mark and so on.). The configuration for projecting this split bright line onto the eye E (split bright line projection part) is housed, for example, in the retinal camera unit 1A (not shown in FIG. 1).

When this split switch 302 is operated, the operation signal is inputted to the controller 210 (or the aforementioned controller inside the retinal camera unit 1A; the same hereinafter). The controller 210 projects the split bright line onto the eye E by controlling the split bright line projection part, in response to the input of this operation signal.

The imaging light amount switch 303 is a switch operated to adjust the emitted light amount of the imaging light source 103 (photographing light amount) depending on the state of the eye E (such as the degree of opacity of the lens). This imaging light amount switch 303 is provided with, for example, a photographing light amount increasing switch "+" for increasing the photographing light amount, a photographing light amount decreasing switch "−" for decreasing the photographing light amount, and a reset switch (a button in the middle) for setting the photographing light amount to a predetermined initial value (default value).

When one of the imaging light amount switches 303 is operated, the operation signal is inputted to the controller 210. The controller 210 controls the imaging light source 103 in response to the inputted operation signal and adjusts the photographing light amount.

The observation light amount switch 304 is a switch operated to adjust the emitted light amount (observation light amount) of the observation light source 101. The observation light amount switch 304 is provided with, for example, an observation light amount increasing switch "+" for increasing the observation light amount, and an observation light amount decreasing switch "−" for decreasing the observation light amount.

When one of the observation light amount switches 304 is operated, the operation signal is inputted to the controller 210. The controller 210 controls the observation light source 101 in response to the inputted operation signal and adjusts the observation light amount.

The jaw holder switch 305 is a switch to move the position of the jaw holder 6 shown in FIG. 36. This jaw holder switch 305 is provided with, for example, an upward movement switch (upward triangle) for moving the jaw holder 6 upward, and a downward movement switch (downward triangle) for moving the jaw holder 6 downward.

When one of the jaw holder switches 305 is operated, the operation signal is inputted to the controller 210. The controller 210 controls a jaw holder movement mechanism (not shown) in response to the inputted operation signal and moves the jaw holder 6 upward or downward.

The photographing switch 306 is a switch used as a trigger switch for capturing a 2-dimensional image of the surface of the fundus oculi Ef or a tomographic image of the fundus oculi Ef.

When the photographing switch 306 is operated in a state where a menu to photograph a 2-dimensional image is selected, the controller 210 that has received the operation signal controls the imaging light source 103 to emit photographing illumination light, and also causes the display 240A or the touch panel monitor 11 to display a 2-dimensional image of the surface of the fundus oculi Ef, based on the video signal outputted from the imaging device 10 having detected the fundus oculi reflection light.

On the other hand, when the photographing switch 306 is operated in a state where a menu to capture a tomographic image is selected, the controller 210 that has received the operation signal controls the low coherence light source 160 to emit the low coherence light L0, and also controls the Galvano mirrors 141A and 141B to scan the signal light LS. Moreover, the controller 210 causes the display 240A or the touch panel monitor 11 to display a tomographic image of the fundus oculi Ef formed by the image forming part 220 (and image processor 230), based on the detection signal outputted from the CCD 184 that has detected the interference light LC.

The zoom switch 307 is a switch operated to change the angle of view (zoom magnification) at the time of photographing of the fundus oculi Ef. Every time this zoom switch 307 is operated, the photographing angle is set alternately to 45 degrees and 22.5 degrees, for example.

When this zoom switch 307 is operated, the controller 210 that has received the operation signal controls a variable magnifying lens driving mechanism (not shown) to move the variable magnifying lens 124 in the optical axis direction of the imaging optical system 120, thereby changing the photographing angle of view.

The image switching switch 308 is a switch operated to switch displayed images. When the image switching switch 308 is operated in a state where a fundus oculi observation image (a 2-dimensional image of the surface of the fundus oculi Ef based on the video signal from the imaging device 12) is displayed on the display 240A or the touch panel monitor 11, the controller 210 having received the operation signal controls the display 240A or touch panel monitor 11 to display the tomographic image of the fundus oculi Ef.

On the other hand, when the image switching switch 308 is operated in a state where a tomographic image of the fundus oculi is displayed on the display 240A or the touch pane monitor 11, the controller 210 having received the operation signal controls the display 240A or the touch panel monitor 11 to display the fundus oculi observation image.

The fixation target switching switch 309 is a switch operated to switch the position of the internal fixation target displayed by the LCD 140 (i.e. the projection position of the internal fixation target on the fundus oculi Ef). By operating this fixation target switching switch 309, the display position of the internal fixation target can be switched, for example, among "fixation position to capture the image of the peripheral region of the center of the fundus oculi (fixation position for fundus oculi center imaging)," "fixation position to capture the image of the peripheral region of macula lutea (fixation position for macula lutea imaging)" and "fixation position to capture the image of the peripheral region of papilla (fixation position for papilla imaging)," in a circulative fashion.

In response to the operation signals from the fixation target switching switch 309, the controller 210 causes the LCD 140 to display the internal fixation target in different positions on the display surface thereof. The display positions of the internal fixation target corresponding to the above three fixation positions, for example, can be preset based on clinical data, or can be set for each eye E (image of the fundus oculi Ef) in advance.

The fixation target position adjusting switch 310 is a switch operated to adjust the display position of the internal fixation target. This fixation target position adjusting switch 310 is provided with, for example, an upward movement switch for moving the display position of the internal fixation target upward, a downward movement switch for moving it downward, a leftward movement switch for moving it leftward, a rightward movement switch for moving it rightward, and a reset switch for moving it to a predetermined initial position (default position).

Upon reception of the operation signal from either of these switches of the fixation target position adjusting switch 310, the controller 210 controls the LCD 140 to move the display position of the internal fixation target, in response to the operation signal.

The fixation target size switching switch 311 is a switch operated to change the size of the internal fixation target. When this fixation target size switching switch 311 is operated, the controller 210 that has received the operation signal controls the LCD 140 to change the display size of the internal fixation target. The display size of the internal fixation target can be switched, for example, between "normal size" and "enlarged size," alternately. As a result, the size of the projection image of the fixation target projected onto the fundus oculi Ef is changed. Upon reception of the operation signal from the fixation target position adjusting switch 311, the controller 210 controls the LCD 140 to change the display size of the internal fixation target, in response to the operation signal.

The mode switching knob 312 is a knob rotationally operated to select various photographing modes, such as a fundus oculi photographing mode to photograph a 2-dimensional image of the fundus oculi Ef, a B-scan mode to perform B-scan of the signal light LS, and a 3-dimensional scan mode to scan with the signal light LS 3-dimensionally. In addition, the mode switching knob 312 may be configured so as to be capable of selecting a replay mode to replay and display a captured 2-dimensional image or tomographic image of the fundus oculi Ef. In addition, it may be configured so as to be capable of selecting a photographing mode to control so that the photographing of the fundus oculi Ef would be performed immediately after scanning of the signal light LS. Control of each part of the device for causing the fundus oculi observation device 1 to execute the operation corresponding to the each mode is executed by the controller 210.

Herein, the feature of control of scanning of the signal light LS by the controller 210, and the feature of processing to the detection signal from the OCT unit 150 by the image forming part 220 and the image processor 230 will be respectively described. An explanation regarding the process by the image forming part 220, etc., to the video signal from the retinal camera unit 1A will be omitted because it is the same as the conventional process.

[Signal Light Scanning]

Scanning of the signal light LS is performed by changing the positions (directions of the reflecting surfaces) of the Galvano mirrors 141A and 141B of the scanning unit 141 in the retinal camera unit 1A. By controlling the mirror drive mechanisms 241 and 242 respectively to change the directions of the reflecting surfaces of the Galvano mirrors 141A and 141B respectively, the controller 210 scans the application position of the signal light LS on the fundus oculi Ef.

When the facing direction of the reflecting surface of the Galvano mirror 141A is changed, the signal light LS is scanned in the horizontal direction (x-direction in FIG. 1) on the fundus oculi Ef. Whereas, when the facing direction of the reflecting surface of the Galvano mirror 141B is changed, the signal light LS is scanned in the vertical direction (y-direction in FIG. 1) on the fundus oculi Ef. Further, by changing the facing directions of the reflecting surfaces of both the Galvano mirrors 141A and 141B simultaneously, it is possible to scan the signal light LS in the composed direction of the x-direction and y-direction. That is, by controlling these two Galvano mirrors 141A and 141B, it is possible to scan the signal light LS in any direction on the x-y plane.

FIGS. 8A and 8B shows one example of the feature of scanning of the signal light LS for forming images of the fundus oculi Ef. FIG. 8A shows one example of the feature of scanning of the signal light LS, when the fundus oculi Ef is seen from a direction that the signal light LS enters the eye E (that is, seen from −z side toward +z side in FIG. 1). Further, FIG. 8B shows one example of the feature of arrangement of scanning points (positions at which image measurement is carried out; target positions of the signal light LS) on each scanning line on the fundus oculi Ef.

As shown in FIG. 8A, the signal light LS is scanned within a rectangular-shaped scanning region R that has been preset. Within this scanning region R, a plurality of (m number of) scanning lines R1 through Rm are set in the x-direction. When the signal light LS is scanned along the respective scanning lines Ri (i=1 through m), detection signals of the interference light LC are generated.

Herein, a direction of each scanning line Ri will be referred to as the "main scanning direction" and a direction orthogonal thereto will be referred to as the "sub-scanning direction". Accordingly, scanning of the signal light LS in the main scanning direction is performed by changing the facing direction of the reflecting surface of the Galvano mirror 141A, and scanning in the sub-scanning direction is performed by changing the facing direction of the reflecting surface of the Galvano mirror 141B.

On each scanning line Ri, as shown in FIG. 8B, a plurality of (n number of) scanning points Ri1 through Rin are preset.

In order to execute the scanning shown in FIGS. 8A and 8B, the controller 210 firstly controls the Galvano mirrors 141A and 141B to set the target of the signal light LS entering into the fundus oculi Ef to a scan start position RS (scanning point R11) on the first scanning line R1. Subsequently, the controller 210 controls the low coherence light source 160 to flush the low coherence light L0, thereby making the signal light LS enter the scan start position RS. The CCD 184 receives the interference light LC based on the fundus oculi reflection light of this signal light LS at the scan start position RS, and outputs the detection signal to the controller 210.

Next, the controller 210 controls the Galvano mirror 141A to scan the signal light LS in the main scanning direction and set the incident target of the signal light LS to a scanning point R12, and makes the low coherence light L0 flushed to make the signal light LS enter into the scanning point R12. The CCD 184 receives the interference light LC based on the fundus oculi reflection light of this signal light LS at the scanning point R12, and then outputs the detection signal to the controller 210.

Likewise, the controller 210 obtains detection signals outputted from the CCD 184 in response to the interference light LC for each scanning point, by flushing the low coherence light L0 at each scanning point while shifting the incident target of the signal light LS from scanning point R13 to R14, - - -, R1 (n−1), and R1n in order.

Once the measurement at the last scanning point R1n of the first scanning line R1 is finished, the controller 210 controls the Galvano mirrors 141A and 141B simultaneously to shift the incident target of the signal light LS to the first scanning point R21 of the second scanning line R2 following a line switching scan r. Then, by conducting the previously described measurement on each scanning point R2j (j=1 through n) of this second scanning line R2, detection signals corresponding to the respective scanning points R2j are obtained.

Likewise, the measurement is conducted for each of the third scanning line R3, - - -, the m−1th scanning line R(m−1), the mth scanning line Rm to obtain the detection signals corresponding to the respective scanning points. Symbol RE on a scanning line Rm is a scan end position corresponding to a scanning point Rmn.

As a result, the controller 210 obtains m×n number of detection signals corresponding to m×n number of scanning points Rij (i=1 through m, j=1 through n) within the scanning region R. Hereinafter, a detection signal corresponding to the scanning point Rij may be represented by Dij.

Such interlocking control of the shift of scanning points and the emission of the low coherence light L0 can be realized by synchronizing, for instance, timing for transmission of control signals to the mirror drive mechanisms 241 and 242 and timing for transmission of control signals (output request signals) to the low coherence light source 160.

As described above, when each of the Galvano mirrors 141A and 141 B is operated, the controller 210 stores the position of each scanning line Ri and the position of each scanning point Rij (coordinates on the x-y coordinate system) as information representing the content of the operation. This stored content (scanning point coordinate information) is used in an image forming process as in conventional one.

[Image Processing]

Next, one example of a process on OCT images (tomography images of the fundus oculi Ef) by the image forming part 220 and the image processor 230 will be described.

The image forming part 220 executes the formation process of tomographic images of the fundus oculi Ef along each scanning line Ri (main scanning direction). Further, the image processor 230 executes the formation process of a 3-dimensional image of the fundus oculi Ef based on these tomographic images formed by the image forming part 220, etc.

The formation process of a tomographic image by the image forming part 220, as in the conventionally one, includes a 2-step arithmetic process. In the first step of the arithmetic process, based on a detection signal Dij corresponding to each scanning point Rij, an image in the depth-wise direction (z-direction in FIG. 1) of the fundus oculi Ef at the scanning point Rij is formed.

Figure 9:
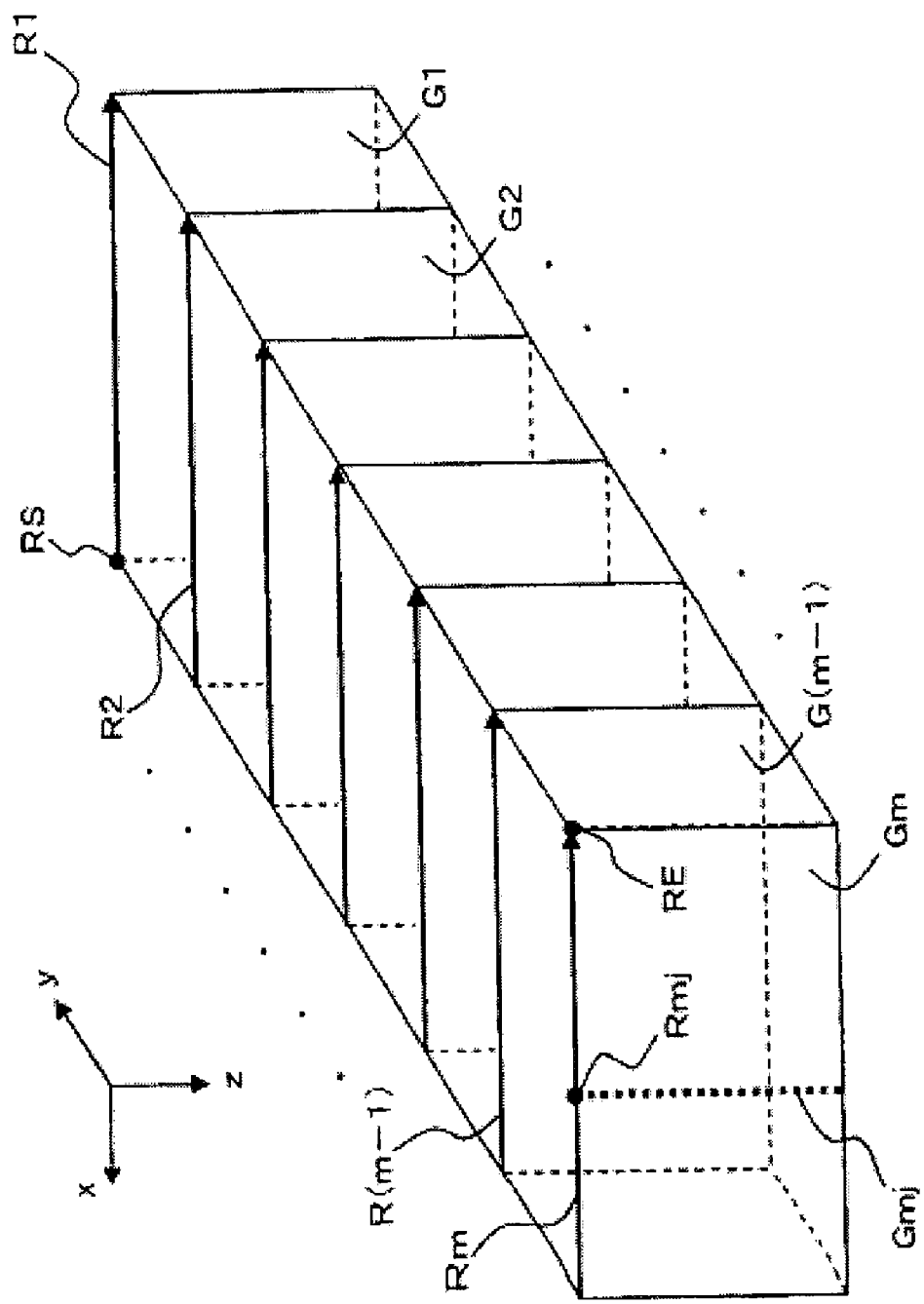
FIG. 9 is a schematic diagram showing one example of a feature of scan of signal light and a feature of a tomographic image formed along each scanning line in the preferred embodiment of the fundus oculi observation device according to the present invention.

FIG. 9 shows a feature of (a group of) tomographic images formed by the image forming part 220. In the second step of the arithmetic process, on each scanning line Ri, based on the images in the depth-wise direction at the n number of scanning points Ri1 through Rin, a tomographic image Gi of the fundus oculi Ef along the scanning line Ri is formed. Then, the image forming part 220 determines the arrangement and the distance of the scanning points Ri1 through Rin referring to the positional information (scanning point coordinate information described before) of the scanning points Ri1 through Rin, and forms a tomographic image Gi along this scanning line Ri.

Through the above process, m number of tomographic images (a group of tomographic images) G1 through Gm at different positions in the sub-scanning direction (y-direction) are obtained.

Here, the formation process of a 3-dimensional image of the fundus oculi Ef by the image processor 230 will be explained. A 3-dimensional image of the fundus oculi Ef is formed based on the m number of tomographic images obtained through the above arithmetic process. The image processor 230 forms a 3-dimensional image of the fundus oculi Ef by performing a known interpolating process to interpolate an image between the adjacent tomographic images Gi and G (i+1).

Here, the image processor 230 determines the arrangement and the distance of each scanning line Ri while referring to the positional information of each scanning line Ri to form this 3-dimensional image. For this 3-dimensional image, a 3-dimensional coordinate system (x,y,z) is set, based on the positional information (the scanning point coordinate information) of each scanning point Rij and the z-coordinate in the depth-wise image.

Furthermore, based on this 3-dimensional image, the image processor 230 can form a tomographic image of the fundus oculi Ef at a cross-section in any direction other than the main scanning direction (x-direction). Once the cross-section is designated, the image processor 230 determines the position of each scanning point (and/or an interpolated depth-wise image) on this designated cross-section, and extracts a depth-wise image at each determined position (and/or an interpolated depth-wise image), thereby forming a tomographic image of the fundus oculi Ef at the designated cross-section by arranging plural extracted depth-wise images.

Furthermore, an image Gmj shown in FIG. 9 represents an image in the depth-wise direction (z-direction) at the scanning point Rmj on the scanning line Rm. A depth-wise image at each scanning point Rij on the scanning line Ri formed by the first-step arithmetic process is represented as "image Gij."

[Usage Pattern]

Figure 10:
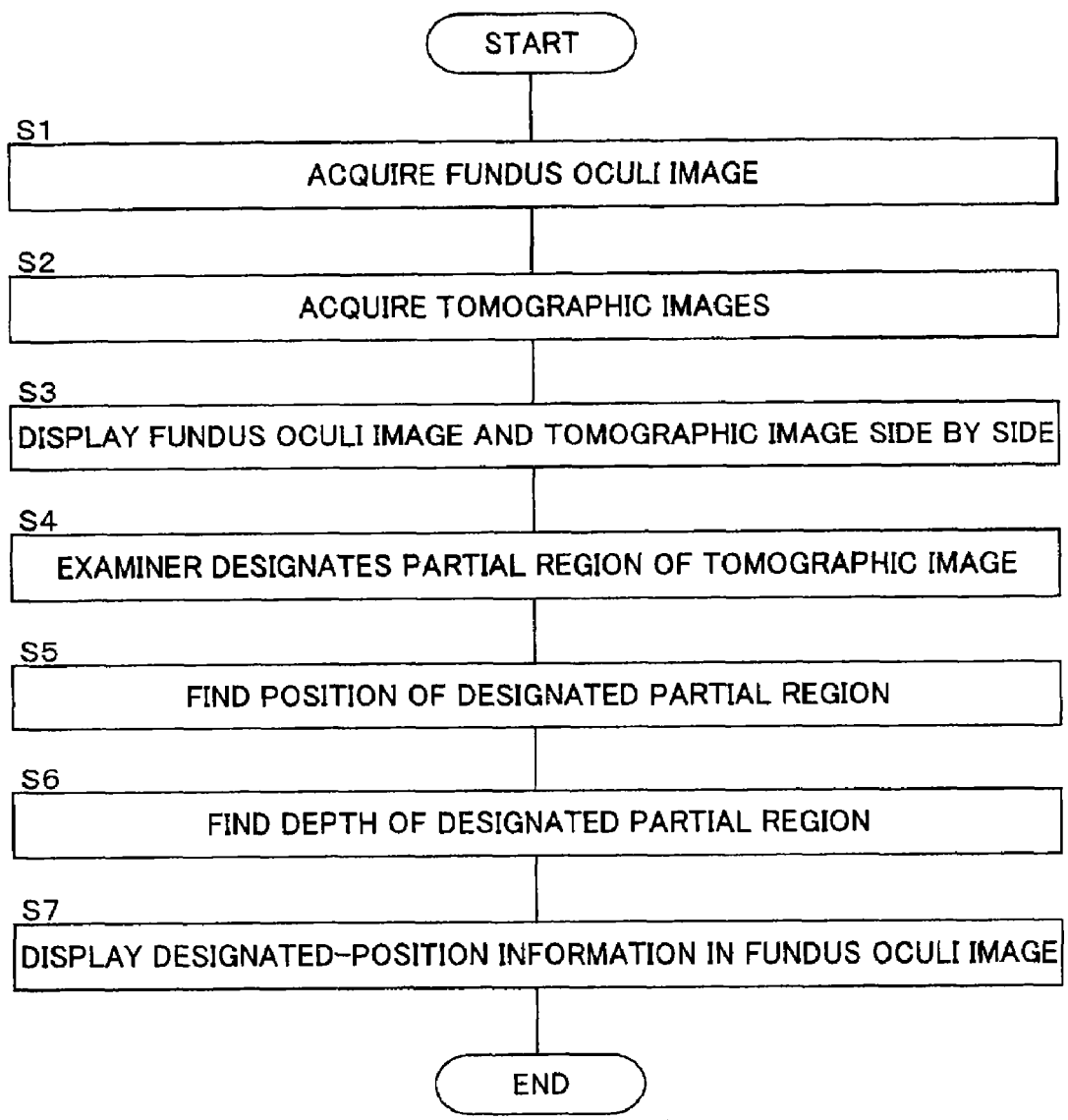
FIG. 10 is a flowchart showing one example of a usage pattern in the preferred embodiment of the fundus oculi observation device according to the present invention.
Figure 12:
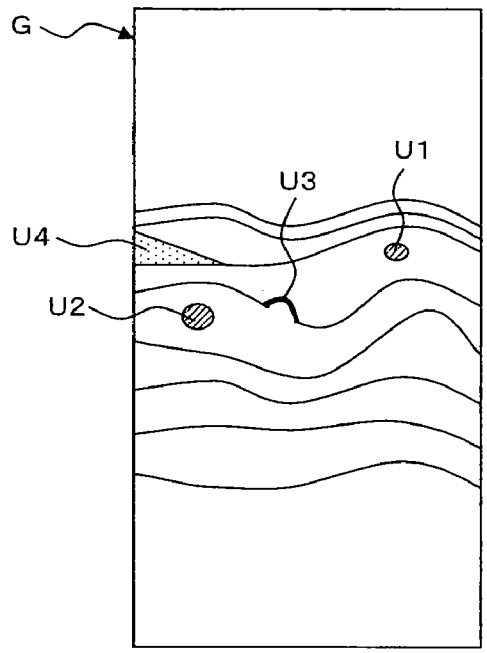
FIG. 12 is a schematic diagram showing one example of a display screen displayed in the preferred embodiment of the fundus oculi observation device according to the present invention.
Figure 13:
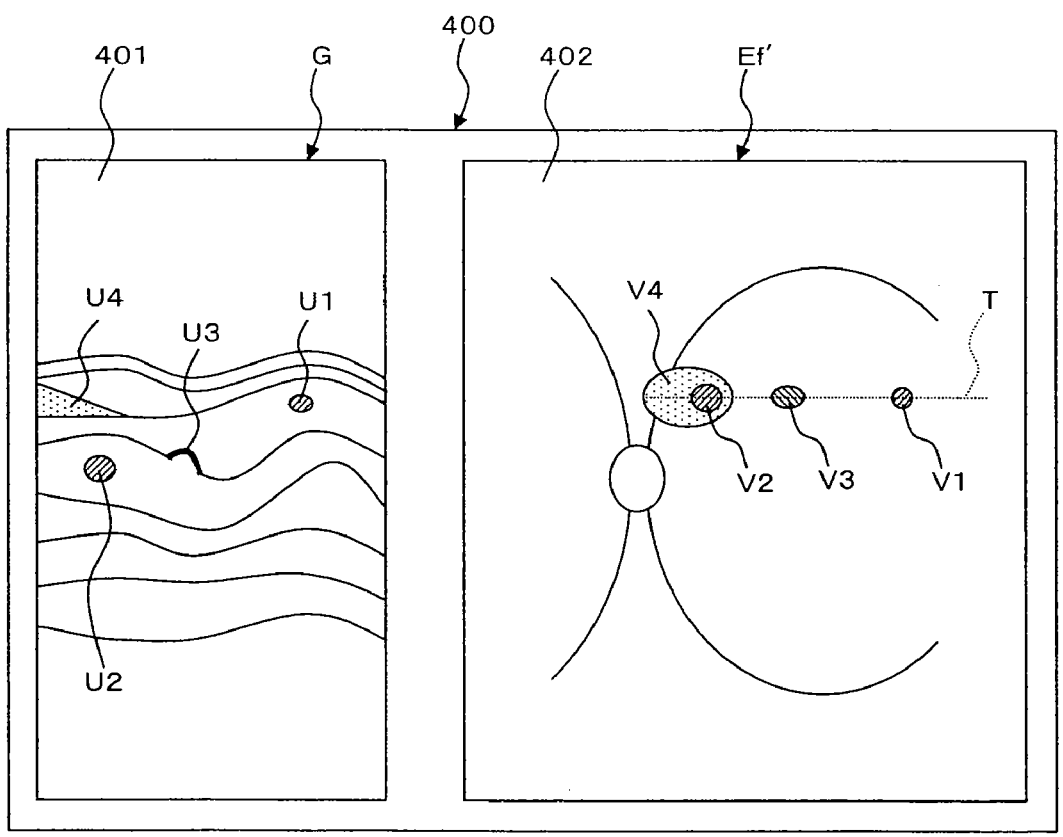
FIG. 13 is a schematic diagram showing one example of a display screen displayed in the preferred embodiment of the fundus oculi observation device according to the present invention.

A usage pattern of the fundus oculi observation device 1 having the configuration as described above will be explained. A flowchart of FIG. 10 shows one example of the usage pattern of the fundus oculi observation device 1. Moreover, FIGS. 11 through 13 show one example of a display screen to be displayed in this usage pattern.

First, the fundus oculi image Ef' and the tomographic images Gi are acquired (S1, S2). Herein, the fundus oculi image Ef' and the tomographic image Gi can be acquired in any order. The main controller 211 causes the image storage 212 to store the acquired fundus oculi image Ef' and tomographic image Gi.

Figure 11:
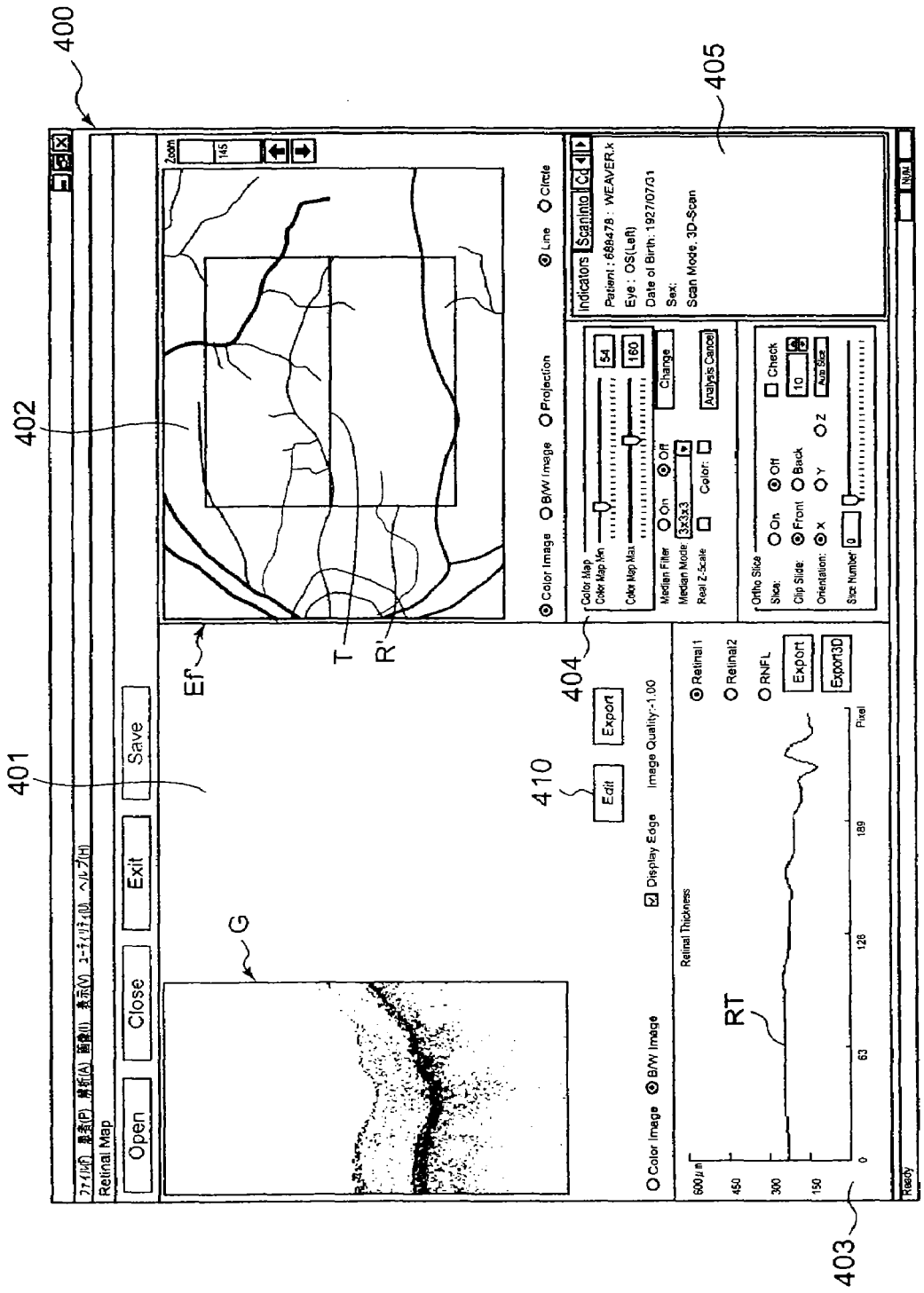
FIG. 11 is a schematic diagram showing one example of a display screen displayed in the preferred embodiment of the fundus oculi observation device according to the present invention.

The main controller 211 causes the display 240A to display a fundus oculi observation screen 400 as shown in FIG. 11. A tomographic image G is displayed in the tomographic image display 401 of the fundus oculi observation screen 400, and the fundus oculi image Ef' is displayed in the fundus oculi image display 402 (S3). At this time, an image indicating the cross-sectional position of the tomographic image G may be displayed in the fundus oculi image Ef'. Furthermore, an image indicating a scanning region R at the time of acquisition of the tomographic image Gi may be displayed in the fundus oculi image Ef'.

The tomographic image G to be displayed is designated by, for example, an examiner. As one example, the examiner designates the cross-sectional position in the fundus oculi image Ef' by using the mouse 206 or the like. The main controller 211 selects and displays the tomographic image Gi of the designated cross-sectional position as the tomographic image G. The tomographic image G of any cross-sectional position can be displayed by forming a 3-dimensional image based on the tomographic image Gi that has been acquired in step S2.

The fundus oculi observation screen 400 has a fundus-oculi-thickness graph display 403, a setting operation part 404, and an information display 405. In the fundus-oculi-thickness graph display 403, a fundus-oculi-thickness graph RT showing the thickness of a fundus oculi (e.g. distance between a retina surface and a retinal pigment epithelium) at each position of the cross section of the tomographic image G is displayed. The fundus-oculi-thickness graph RT is formed by, for example, the image processor 230 analyzing the pixel values of the tomographic image G to specify an image region equivalent to the retina surface and the retina pixel epithelial layer and calculating the distance between them. For the setting operation part 404, various kinds of software keys are designed to be used for setting operations related to display modes of the fundus oculi image Ef' or the tomographic image G. In the information display 405, various kinds of information related to the fundus oculi image Ef' or the tomographic image G (e.g. information related to a patient (patient information) such as patient ID, patient name, patient date of birth, patient sex, etc., or distinction between the right or the left eye being examined E (left eye/right eye), or the scanning method used when the tomographic image Gi is formed) are displayed.

The examiner specifies an attention site such as a lesion by observing the tomographic image G, and designates a partial region of the tomographic image G equivalent to the specified attention site (S4). This designating operation can be conducted, for example, through dragging operations using the mouse 206. The main controller 211 finds a position of each designated partial region, and causes the designated-position storage 213 to store (S5).

A position in the fundus oculi image Ef' and a position in the tomographic image G are associated with each other by the previously described xyz coordinate system. The position of the designated partial region is stored in the designated-position storage 213 as, for example, coordinate values in the xyz coordinate system.

The "partial region" designated by the examiner may be an image region having 2-dimensional spreading, a 1-dimensional linear image region, or an image region composed of a single point. Moreover, the examiner can designate any number of one or more partial regions.

One example of a designating pattern of a partial image is described with reference to FIG. 12. As lesions of the fundus oculi Ef, cavities U1, U2, protruding part U3 of a tumor etc., and an area where a layer has been peeled (peeled area) U4 are represented in the tomographic image G shown in the same figure. By operating the mouse 206 or the like, the examiner designates a partial region so as to surround each of the cavities U1, U2, designates a partial region so as to trace the protruding part U3, and designates a partial region so as to surround the peeled area U4.

From hereon, the partial regions having been designated with respect to the respective lesions U1 to U4 are respectively represented by the same symbols of U1 through U4. Moreover, the positions (ref. step S5) of the respective partial regions Ui (i=1 to 4) are described as (xi, yi, zi).

Next, the depth detector 214 finds the depth of each designated partial region Ui (S6). The depth of each partial region Ui is described as di.

The main controller 211 displays the designated-position information indicating the position of each partial region Ui within the fundus oculi image Ef' so as to be superimposed on the fundus oculi image Ef', based on the position (xi, yi, zi) of each partial region Ui stored in the designated-position storage 213 and the depth di of each partial region Ui.

FIG. 13 shows one example of a display mode of the designated-position information. The designated-position information V1, V2, V3, V4 indicating positions that correspond to partial regions U1, U2, U3, U4 are respectively displayed on the fundus oculi image Ef' of the fundus oculi observation screen 400 shown in the same figure. The symbol T is cross-section position information indicating the cross-sectional position of a tomographic image G in the fundus oculi image Ef'. There is no need to display the cross-section position information.

Each designated-position information Vi indicates a position of a lesion of the partial region Ui when the fundus oculi Ef of the eye E is seen from the anterior side of the eye. The tomographic image G in FIG. 13 is an image of the x-z cross-section of the fundus oculi Ef. Each designated-position information Vi in FIG. 13 spreads also in a y-direction (vertical direction in the fundus oculi observation screen 400). The spreading in the y-direction may be found by conducting the same process as in the tomographic image G described above, for example, with respect to tomographic images G (p±1), G (p±2), . . . , G (p±q) of a cross-sectional position close to the tomographic image G (described as Gp).

Furthermore, the designated-position information Vi is displayed in a display mode appropriate for the type of partial region Ui. For example, the designated-position information V1, V2 that correspond to the cavities U1, U2 are displayed in blue; the designated-position information V3 that corresponds to the protruding part U3 is displayed in green; and the designated-position information V4 that corresponds to the peeped area U4 is displayed in pink. A concrete example of this process is described. First, when designating a partial region Ui, the examiner inputs the type of the partial region Ui. Regarding the inputting method, software keys for inputting the type may be provided for the display screen, but it is also possible to configure so as to selectively input by displaying the choice of types through a right-click operation of the mouse 206 or the like. The controller 210 stores the designated partial region Ui and the inputted type by associating the two. Moreover, list information etc. in which the type of partial region and the display color have been associated is stored preliminarily in the controller 210. Then, the controller 210 specifies the display color that corresponds to the associated type in the partial region Ui when the designated-position information Vi of the partial region Ui is displayed and displays the designated-position information Vi in the specified display color.

An optional display mode in which the type of a partial region is distinguishable (e.g. changing daubing patterns (shade, solid paint, etc.)) may be adapted instead of changing the display color as described. Furthermore, it is also possible to make the type of the partial region distinguishable by using information such as character strings, figures, or images indicating the type of partial region. Also, it is possible to constitute so as to pop-up display the information indicating the type of a partial region that corresponds to the designated-position information in response to operations such as pointing a mouse pointer on the designated-position information that has been displayed. In addition, voice information indicating the type of a partial region that corresponds to the designated-position information may also be outputted in response to an operation such as pointing the mouse pointer on the designated-position information.

Furthermore, in step S7 the main controller 211 displays the designated-position information Vi in a display mode appropriate for the depth di of the partial region Ui. As for the display mode, for example, the display density (gradation) of the designated-position information Vi may also be changed appropriately for the depth di. As a concrete example of this, a display density ρk appropriate for levels Dk (k=1 to K) of a depth D is stored in the main controller 211 (hard disk drive 204, etc.) preliminarily. It is also possible to constitute so as to display the designated-position information Vi with a density ρk corresponding to the level Dk by specifying the level Dk that the depth di of the partial region Ui belongs to.

An optional display mode in which the depth of a partial region is distinguishable by, for example, changing the daubing pattern or the like may be adapted instead of changing the display density as described. Moreover, it is also possible to make the depth of the partial region distinguishable by using information such as character strings representing the depth of the partial region. It is also possible to constitute to pop-up display the information indicating the depth of the partial region that corresponds to the designated-position information in response to an operation such as pointing a mouse pointer on the designated-position information that has been displayed. In addition, voice information indicating the depth of the partial region that corresponds to the designated-position information may also be output in response to an operation such as pointing the mouse pointer on the designated-position information.

[Actions and Advantageous Effects]

The actions and advantageous effects of the fundus oculi observation device 1 will be described.

This fundus oculi observation device 1 forms a 2-dimensional image (fundus oculi image Ef) of the surface of the fundus oculi Ef and the tomographic image Gi of the fundus oculi Ef, and displays the fundus oculi image Ef and the tomographic image G side by side in the display 240A. Furthermore, in response to the examiner's designation of the partial region Ui of the tomographic image G, the fundus oculi observation device 1 finds the position in the fundus oculi image Ef corresponding to the partial region Ui, and acts so as to display the designated-position information Vi in the superimposed state on the fundus oculi image Ef.

According to the described fundus oculi observation device 1, the examiner can grasp of what site of the fundus oculi surface an attention site such as a lesion existing in the deep part of the fundus oculi is located in the deep part. Therefore, it is possible to grasp in detail the size, position and distribution state of the attention site.

Further, according to the fundus oculi observation device 1, when plural types of the partial regions Ui are designated, the device acts so as to display the designated-position information Vi in different display modes for the respective types of the partial regions Ui, so that it is possible to grasp in detail the states and positions of attention sites such as lesions of the fundus oculi Ef.

Further, according to the fundus oculi observation device 1, the device acts so as to detect the depth di of the designated partial region Ui in the tomographic image G and display the designated-position information Vi in a display mode appropriate for the depth di, so that it is possible to grasp in detail the state and position of an attention site such as a lesion of the fundus oculi Ef.

MODIFICATIONS

A modification of the fundus oculi observation device 1 according to the present embodiment will be described.

Figure 14:
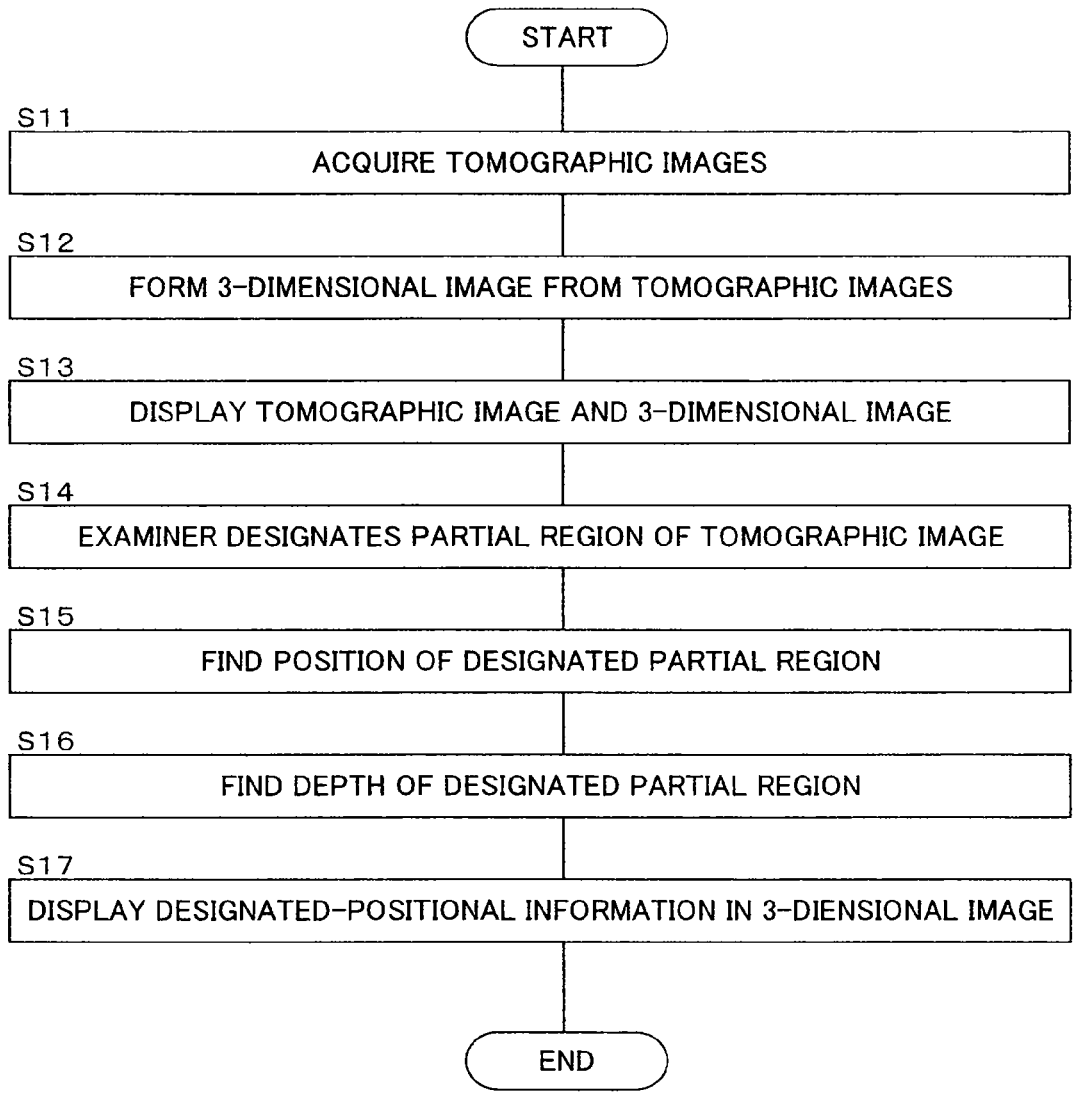
FIG. 14 is a flowchart showing one example of a usage pattern in the preferred embodiment of the fundus oculi observation device according to the present invention.

In the above embodiment, the designated-position information corresponding to the partial region of the tomographic image G is displayed in the fundus oculi image Ef, but the same designated-position information may be displayed so as to be superimposed on a 3-dimensional image. One example of the usage pattern will be described below (refer to a flowchart of FIG. 14).

First, the tomographic images Gi are acquired (S11). The image processor 230 forms a 3-dimensional image H of the fundus oculi Ef based on the acquired tomographic images Gi (S12). The main controller 211 causes the image storage 212 to store (the image data of) the tomographic image Gi and 3-dimensional image H.

Figure 15:
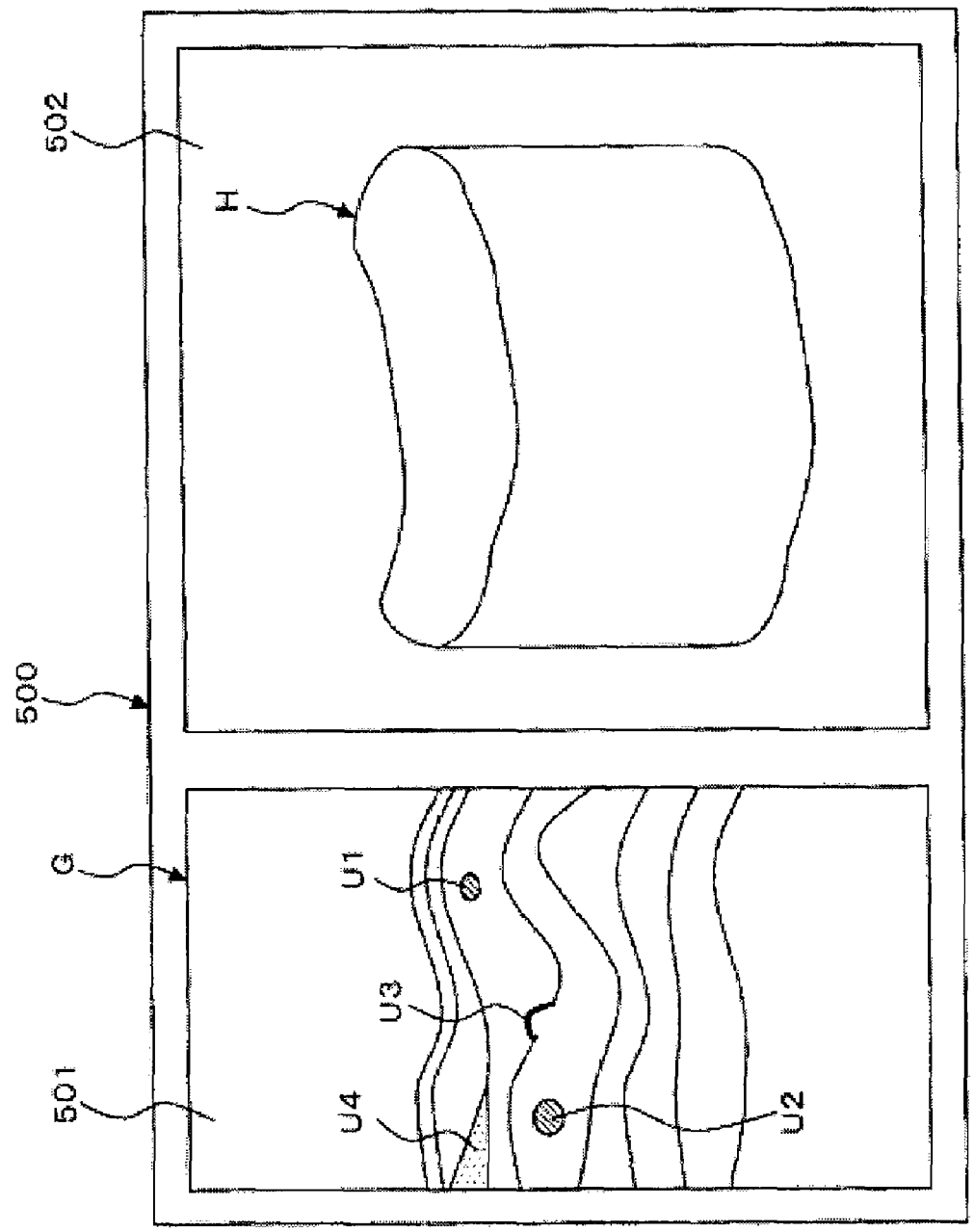
FIG. 15 is a schematic diagram showing one example of a display screen displayed in the preferred embodiment of the fundus oculi observation device according to the present invention.

The main controller 211 causes the display 240A to display a fundus oculi observation screen 500 as shown in FIG. 15. The tomographic image G is displayed in a tomographic image display 501 of the fundus oculi observation screen 500, and the 3-dimensional image H is displayed in a 3-dimensional image display 502 (S13). The 3-dimensional image H is a pseudo 3-dimensional image (perspective view) acquired by rendering volume data with respect to a view direction.

The examiner observes the tomographic image G to specify an attention site such as a lesion and also designate partial regions U1 through U4 of the tomographic image G equivalent to the specified attention site (S14). The main controller 211 finds the positions of the respective designated partial regions Ui, and causes the designated-position storage 213 to store (S15).

Because the 3-dimensional image H has been formed from the tomographic images Gi, a position in the tomographic image G and a position in the 3-dimensional image H are associated with each other by the aforementioned xyz coordinate system. The positions of the respective designated partial regions Ui are stored in the designated-position storage 213 as, for example, coordinate values of the xyz coordinate system.

Next, the depth detector 214 finds the depth di of each of the designated partial regions Ui (S16). The main controller 211 acts so as to display the designated-position information Vi indicating the position of each of the partial regions Ui in the 3-dimensional image H in the superimposed state on the 3-dimensional image H, based on the position (xi, yi, zi) of each of the partial regions Ui stored in the designated-position storage 213 and based on the depth di of each of the partial regions Ui (S17).

At this moment, the main controller 211 acts so as to display the 3-dimensional image H in a half-transparent state so that the designated-position information Vi positioned inside the 3-dimensional image H can be seen through.

Figure 16:
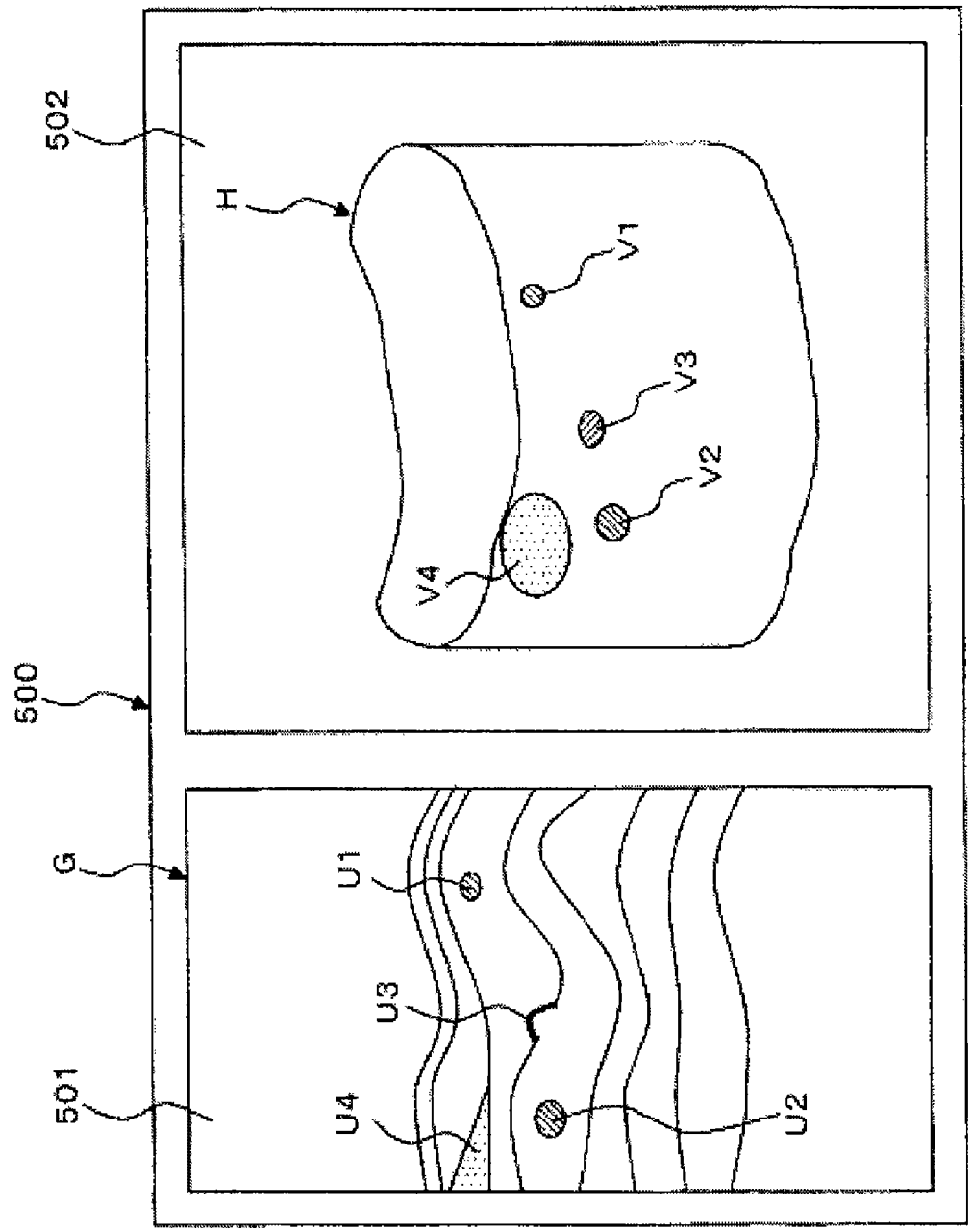
FIG. 16 is a schematic diagram showing one example of a display screen displayed in the preferred embodiment of the fundus oculi observation device according to the present invention.

FIG. 16 shows one example of a display mode of the designated-position information in the 3-dimensional image H. In the 3-dimensional image H of FIG. 16, the designated-position information Vi corresponding to each of the partial regions Ui is displayed. By displaying such designated-position information Vi, the examiner can grasp the 3-dimensional position of an attention site such as a lesion existing in the deep part of the fundus oculi. Therefore, it is possible to grasp in detail the size, position and distribution state of the attention site.

Also in this modification, it is possible, when plural types of the partial regions Ui are designated, to display the designated-position information Vi in different display modes for the respective types of the partial regions Ui, as in the above embodiment.

Likewise, in this modification, the designated-position information Vi may be displayed in a display mode appropriate for the depth di of the designated partial region Ui.

Further, the image processor 230 is capable of forming a tomographic image at any cross-sectional position of the 3-dimensional image H. Therefore, it is possible to properly display an image region of the designated-position information Vi positioned inside the 3-dimensional image H or a tomographic image of a cross-section crossing a peripheral region thereof. Consequently, it is possible to observe in detail an attention region indicated by the designated-position information V1 or a peripheral region thereof. At this moment, it is possible to display a tomographic image of the x-y cross section, a tomographic image of the y-z cross section and a tomographic image of the z-x cross section in any combination together with (a partial image of) the 3-dimensional image H.

In the fundus oculi observation device used only for the usage pattern according to this modification, the configuration for forming the fundus oculi image Ef is unnecessary among the configurations of the fundus oculi observation device 1 in the above embodiment. Therefore, this fundus oculi observation device can be composed of only an optical image measurement device.

The fundus oculi observation device related to this modification comprises an image forming part for forming a plurality of tomographic images Gi of the fundus oculi Ef and forming the 3-dimensional image H of the fundus oculi Ef based on the tomographic image Gi, a display, a controller for causing the display to display the tomographic image G and the 3-dimensional image H side by side, and a designating part for designating the partial region Ui of the tomographic image G. The controller acts so as to find the position in the 3-dimensional image H corresponding to the designated partial region Ui and display the designated-position information Vi in the superimposed state on the 3-dimensional image H.

In a case where the fundus oculi observation device of the modification is configured by modifying the fundus oculi observation device 1 in the above embodiment, the "image forming part" comprises each part of the retinal camera unit 1A for acquiring a tomographic image of the fundus oculi Ef, the OCT unit 150, the image forming part 220 (OCT image forming board 208b), and the image processor 230. The "display," "controller" and "designating part" are the same as in the above embodiment.

Second Embodiment

A fundus oculi observation device of a second embodiment related to the present invention is described. This fundus oculi observation device has almost the same constitution as in the first embodiment. Specifically, the constitutions shown in FIG. 1 through FIG. 6 are the same in this embodiment. From hereon, for identical constitutional portions as in the first embodiment, the same reference numerals are given for the explanation.

[Device Configuration]

Figure 17:
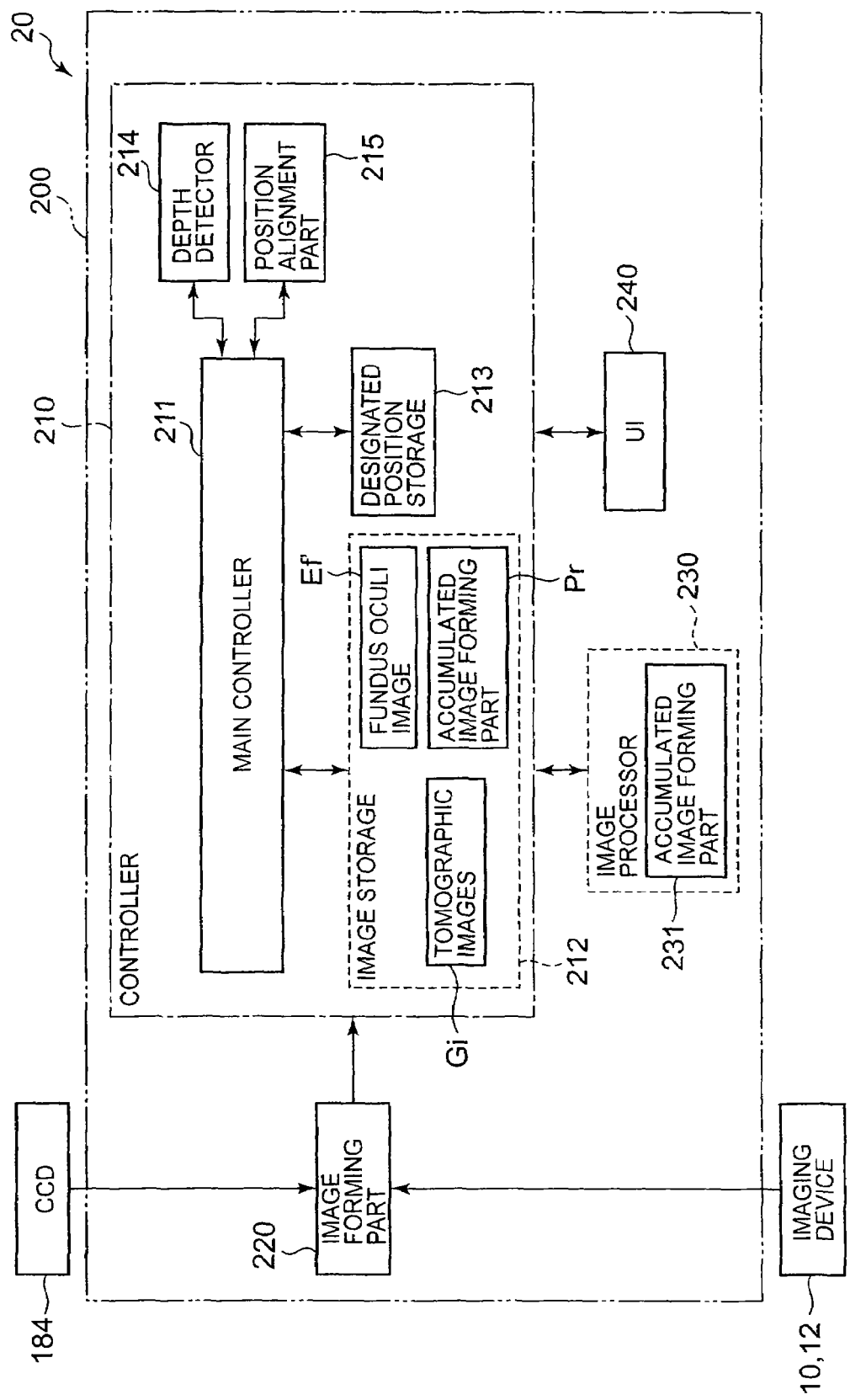
FIG. 17 is a schematic block diagram showing one example of the functional configuration of the arithmetic and control unit in the preferred embodiment of the fundus oculi observation device according to the present invention.

FIG. 17 shows one example of the configuration of an arithmetic control device 200 of a fundus oculi observation device 20 related to this embodiment. In addition to the configuration of the first embodiment, the fundus oculi observation device 20 shown in FIG. 17 comprises a position alignment part 215 and an accumulated image forming part 231.

The accumulated image forming part 231 executes a process for forming an image obtained by accumulating tomographic images Gi formed by the image forming part 220 in the depth direction (z-direction) (an accumulated image), and functions as one example of the "accumulated image forming part" in the present invention. To be more specific, the accumulated image forming part 231 accumulates the depth-wise images Gij composing the tomographic image Gi in the depth direction, thereby forming a dot image.

Here, "accumulating in the depth direction" refers to an arithmetic process of summing (projecting), in the depth direction, brightness values (pixel values) at the respective depth positions of the depth-wise images Gij. Therefore, the dot image obtained by accumulating the depth-wise image Gij has a brightness value, which is the sum of brightness values at the respective z positions of the depth-wise images Gij in the depth direction.

The accumulated image forming part 231, for each of m pieces of tomographic images G1 through Gm obtained through a series of scans with the signal light LS (refer to see FIG. 9), accumulates the respective depth-wise images Gij composing the tomographic image Gi in the depth direction, thereby forming an accumulated image composed of (m×n) pieces of dot images that are 2-dimensionally distributed in the scanning region R of the signal light LS at the time of acquisition of the m pieces of tomographic images G1 through Gm. This accumulated image becomes an image representing the state of the surface of the fundus oculi Ef in the same manner as the fundus oculi image Ef' in the scanning region R (a 2-dimensional image of a fundus oculi surface). The accumulated image is described in detail by the present applicant in Japanese Unexamined Patent Application Publication No. JP-A 2005-337628.

The position alignment part 215 is provided within the controller 210. The position alignment part 215 is for conducting position alignment of an accumulated image formed by the accumulated image forming part 231 with respect to the fundus oculi image Ef, and functions as one example of the "position alignment part" of the present invention.

A specific example of a process for position alignment of an image by the position alignment part 215 is described. As a first example, there is the process described in Japanese Patent Application No. 2006-160896 from the present applicant in which: (1-1) an image region (first vascular region) equivalent to the fundus oculi vascular is extracted from the fundus oculi image Ef' and an image region (second vascular region) equivalent to the fundus oculi vascular is extracted from the accumulated image; (1-2) position alignment of the first vascular region and the second vascular region is conducted; and (1-3) position alignment of the fundus oculi image Ef' and the accumulated image is conducted based on the result of the position alignment of the vascular regions.

Further, as a second example, there is the process described in Japanese Unexamined Patent Application Publication No. JP-A 2007-130403 from the present applicant et al in which: (2-1) as for each tomographic image Gi, the position of the tomographic image Gi and the measurement position of the tomographic image Gi (i.e. the scanning position (scanning point coordinate information) of the signal light LS when the tomographic image Gi is formed) are compared to detect displacement in the x-y direction between the two; and (2-2) the position shift in the x-y direction of each tomographic image Gi is corrected based on the detection result of the displacement. That is, the position of the tomographic image Gi is moved by the detection result of the displacement, thereby being aligned with the position of the fundus oculi image Ef'.

The process for position alignment of images by the position alignment part 215 is not limited to the position alignment in the x-y direction, but may also be conducted based on the magnifying ratio of the image (magnifying ratio for photographing or display magnifying ratio). For example, if the magnifying ratio of the fundus oculi image Ef' is $\alpha$, the position alignment part 215 multiplies the size of the fundus oculi image Ef' by $1/\alpha$ or multiplies the size of an accumulated image by a to conduct the position alignment process as described above.

Also, the process for position alignment of images by the position alignment part 215 may include a rotation in the x-y plane. The rotational angle of an image may be derived from the displacement (above first example) of the first vascular region and the second vascular region. Also, the rotational angle of the image may be derived based on the displacement of the vascular region at the edge of an accumulated image (image region equivalent to the fundus oculi vascular) and of a vascular region of the fundus oculi mage Ef' in contact with the edge.

As described, the process for position alignment of images by the position alignment part 215 includes an affine transformation into which a parallel movement, rotation, enlargement/reduction, etc. of the image are taken into consideration. Furthermore, in some cases, it is possible to constitute so that the reversal of the image (horizontal reversal, vertical reversal) can be performed.

[Usage Pattern]

Figure 18:
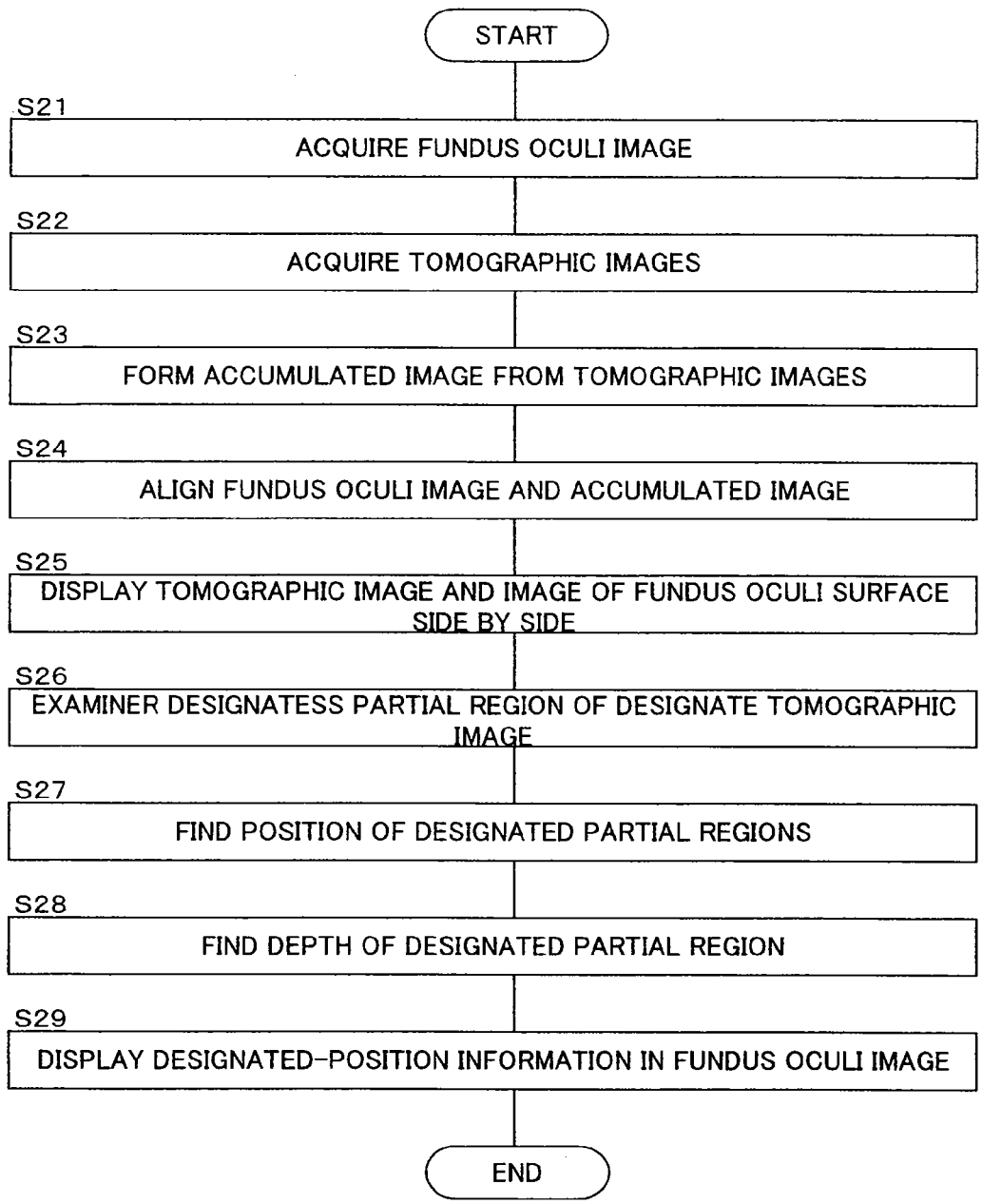
FIG. 18 is a flowchart showing one example of a usage pattern in the preferred embodiment of the fundus oculi observation device according to the present invention.

The usage pattern of the fundus oculi observation device 20 related to the present embodiment is described. The flowchart in FIG. 18 shows one example of the usage pattern of the fundus oculi observation device 20.

First, the fundus oculi image Ef' and the tomographic images Gi are acquired (S21, S22). The accumulated image forming part forms an accumulated image Pr of the fundus oculi Ef based on the acquired tomographic images Gi (S23). The main controller 211 causes the image storage 212 to store (image data of) the fundus oculi image Ef', tomographic images Gi and accumulated image Pr.

Figure 19:
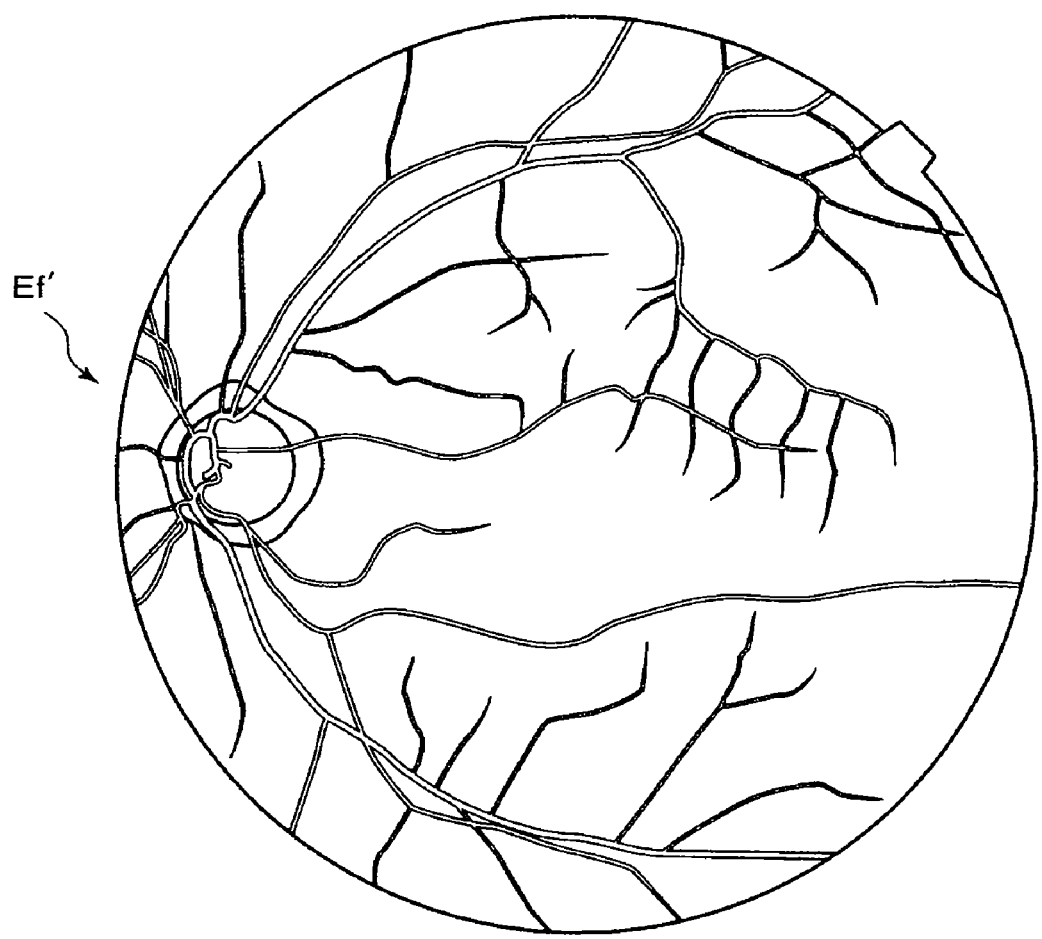
FIG. 19 is a schematic explanatory diagram for explaining one example of the usage pattern in a preferred embodiment of the fundus oculi observation device according to the present invention.
Figure 20:
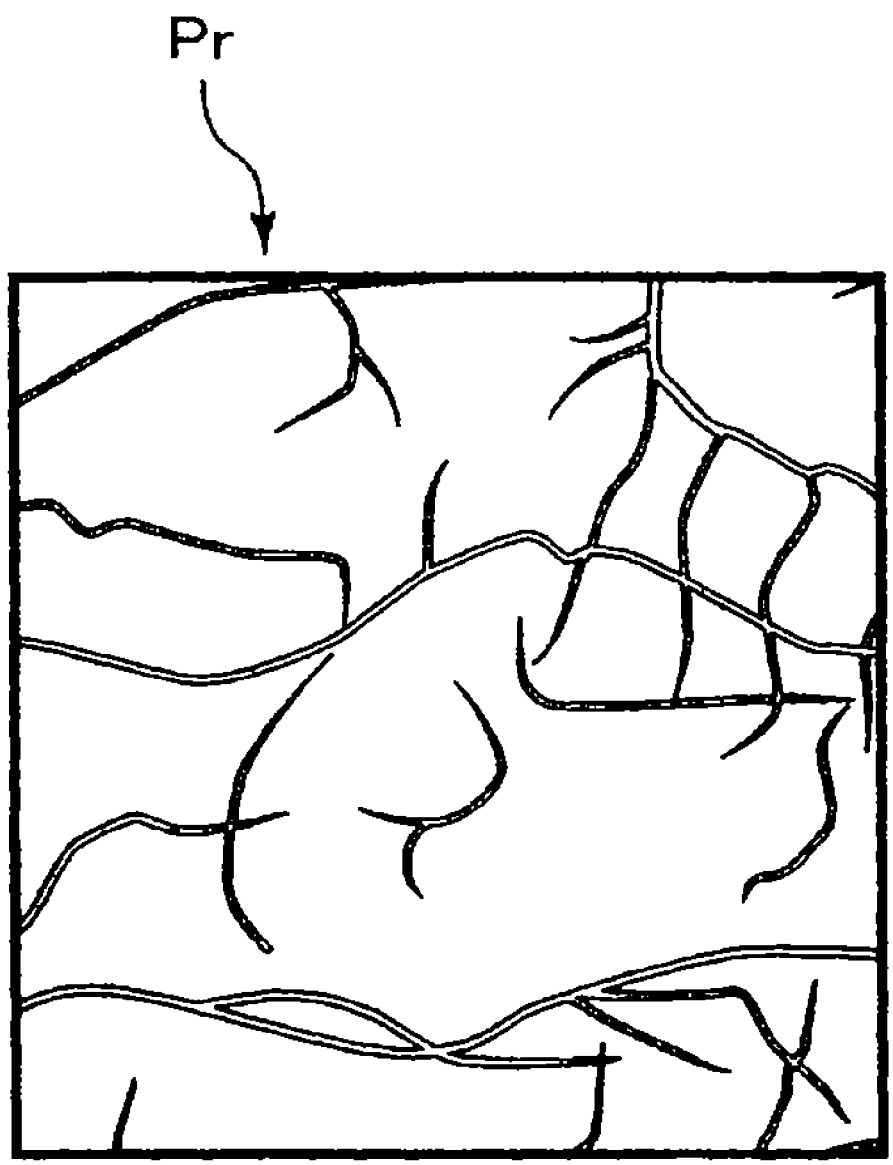
FIG. 20 is a schematic explanatory diagram for explaining one example of the usage pattern in a preferred embodiment of the fundus oculi observation device according to the present invention.

The position alignment part 215 conducts position alignment of the accumulated image Pr with respect to the fundus oculi image Ef' (S24). Herein, a case of conducting the process in step S24 is described with reference to FIG. 19 through FIG. 23 and using examples such as the above first example. FIG. 19 shows one example of the fundus oculi image Ef'. FIG. 20 shows one example of the accumulated image Pr.

Figure 21:
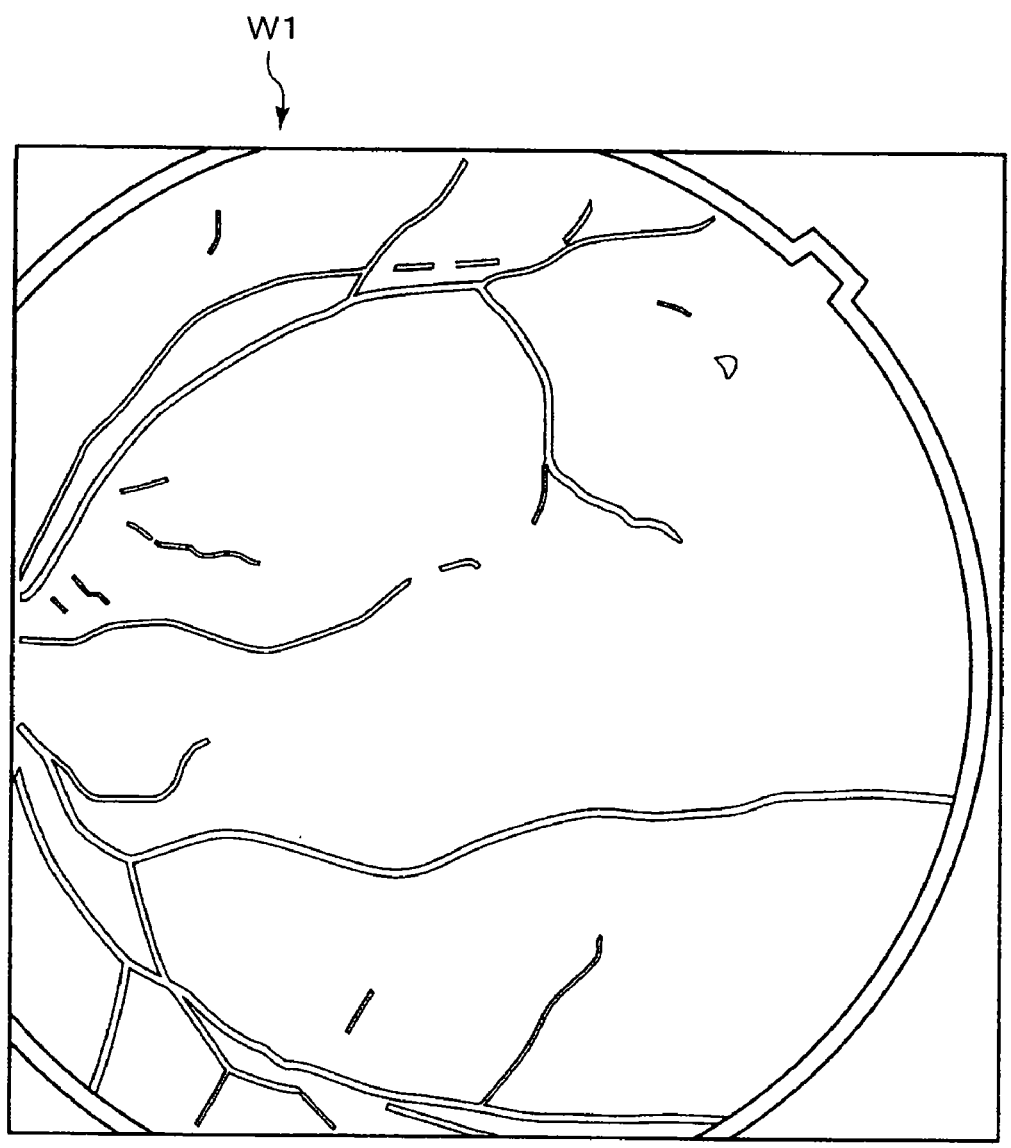
FIG. 21 is a schematic explanatory diagram for explaining one example of the usage pattern in a preferred embodiment of the fundus oculi observation device related to the present invention.
Figure 22:
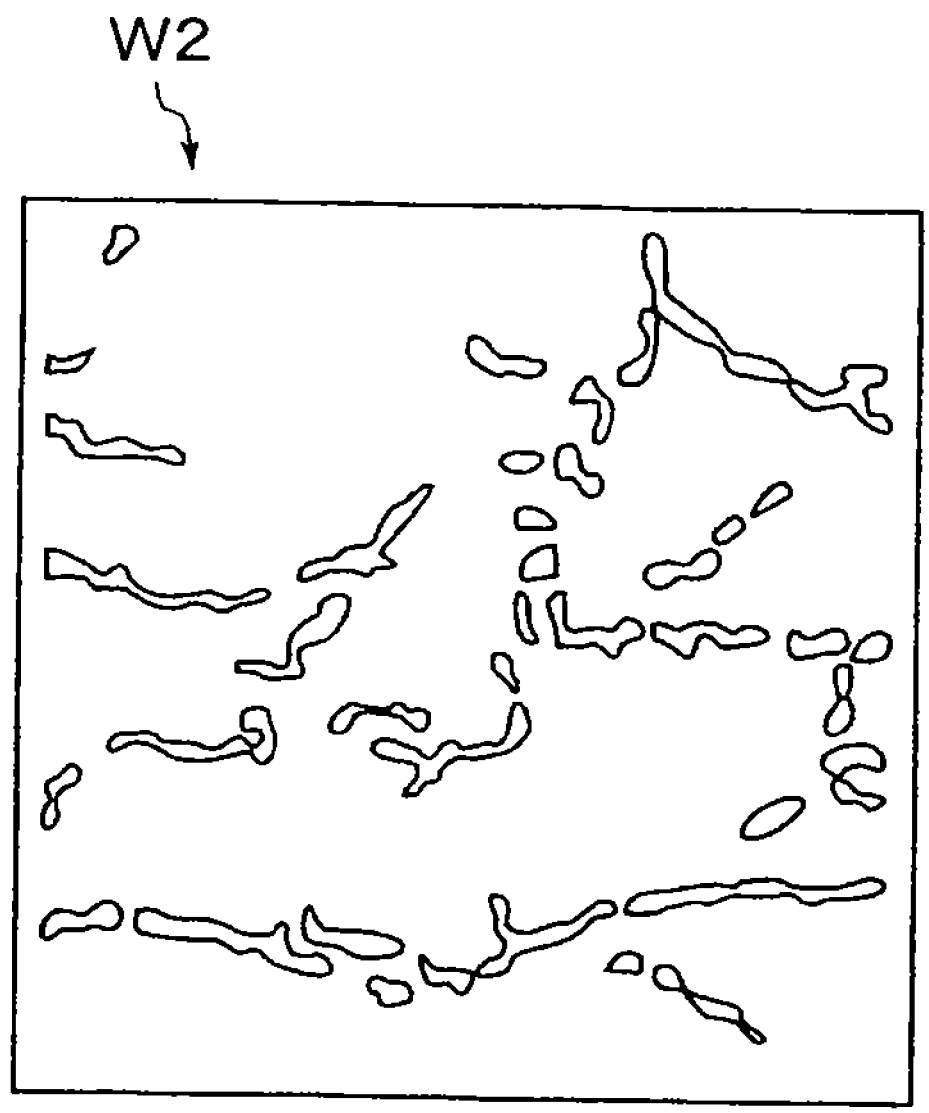
FIG. 22 is a schematic explanatory diagram for explaining one example of the usage pattern in a preferred embodiment of the fundus oculi observation device according to the present invention.

The position alignment part 215 extracts a vascular region W1 (ref. FIG. 21) included in the fundus oculi image Ef' and also extracts a vascular region W2 (ref. FIG. 22) included in the accumulated image Pr. Furthermore, the position alignment part 215 conducts position alignment between the vascular region W1 extracted from the fundus oculi image Ef' and the vascular region W2 extracted from the accumulated image Pr by conducting the affine transformation or the like.

Figure 23:
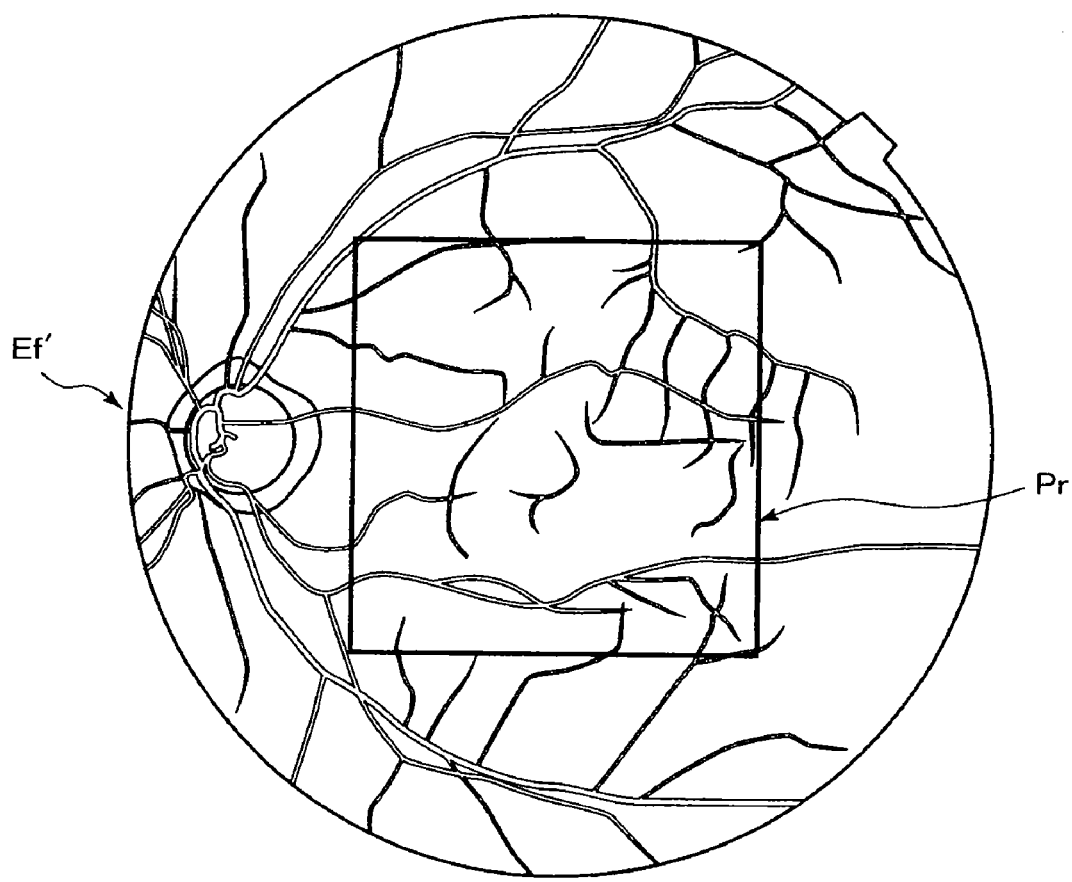
FIG. 23 is a schematic explanatory diagram for explaining one example of the usage pattern in a preferred embodiment of the fundus oculi observation device according to the present invention.

The position alignment part 215 conducts position alignment of the accumulated image Pr with respect to the fundus oculi image Ef' by using the result of the position alignment of the vascular regions W1, W2. FIG. 23 shows one example of a state of an image when the fundus oculi image Ef' and the accumulated image Pr thus aligned are superimposed (that is, when the accumulated image Pr is embedded in the fundus oculi image Ef').

Figure 24:
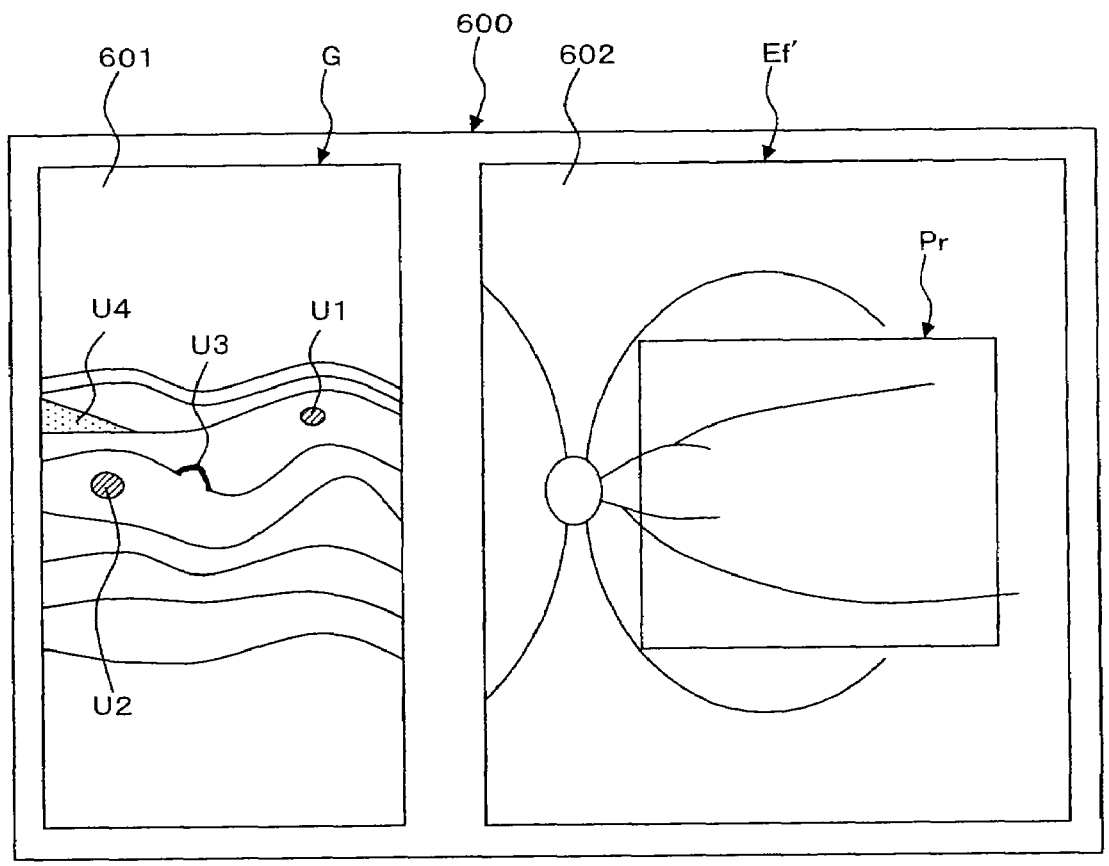
FIG. 24 is a schematic diagram showing one example of a display screen displayed in a preferred embodiment of the fundus oculi observation device according to the present invention.

The main controller 211 causes the display 240A to display a fundus oculi observation screen 600 as shown in FIG. 24. A tomographic image display 601 of the fundus oculi observation screen 600 displays a tomographic image G and a fundus oculi surface image display 602 displays a fundus oculi image Ef' into which an accumulated image Pr is embedded (S25). From hereon, a fundus oculi image Ef' in which an accumulated image Pr is embedded may be referred to as a "fundus oculi surface image."

The examiner observes the tomographic image G to specify an attention site such as a lesion and also designate partial regions U1 through U4 of the tomographic image G equivalent to the specified attention site (S26). The main controller 211 finds the position of each designated partial region Ui and causes the designated-position storage 213 to store (S27).

Because the position alignment of the accumulated image Pr and the fundus oculi image Ef' have been conducted, the position in the tomographic image G and the position in the fundus oculi surface image are associated with each other by the previously described xyz coordinate system. The position of each designated partial region Ui is stored in the designated-position storage 213, for example, as a coordinate value of the xyz coordinate system.

Next, the depth detector 214 finds the depth di of each designated partial region Ui (S28). The main controller 211 acts so as to display the designated-position information Vi indicating the position of each partial region Ui in the fundus oculi surface image (accumulated image Pr) in the superimposed state on the fundus oculi surface image, based on the position (xi, yi, zi) of each partial region Ui stored in the designated-position storage 213 and the depth di of each partial region Ui (S29). Then, each designated-position information Vi is displayed in the accumulated image Pr within the fundus oculi surface image.

Figure 25:
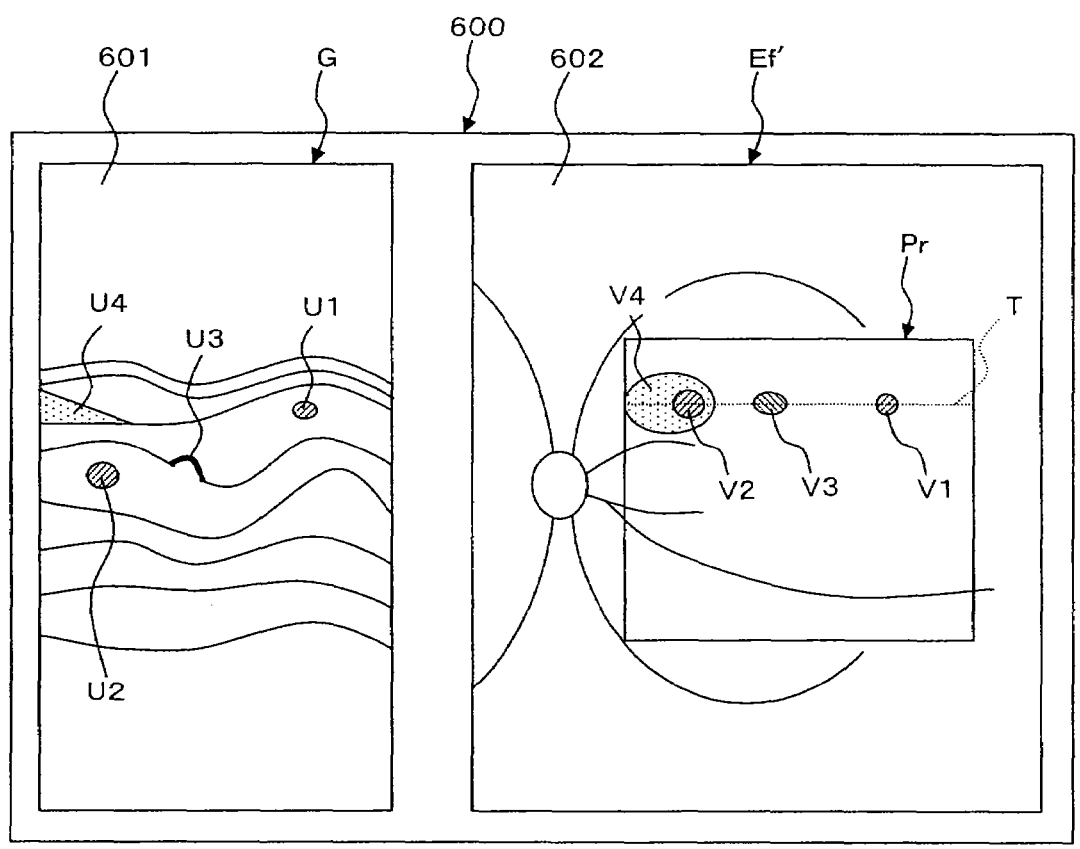
FIG. 25 is a schematic diagram showing one example of a display screen displayed in a preferred embodiment of the fundus oculi observation device according to the present invention.

FIG. 25 shows one example of display modes of designated-position information. Designated-position information V1, V2, V3, V4 indicating positions that correspond to partial regions U1, U2, U3, U4 are displayed in the accumulated image Pr of the fundus oculi surface image in the fundus oculi observation screen 600 shown FIG. 25. The symbol T indicates cross-section position information indicating the cross-sectional position of the tomographic image G in a fundus oculi surface image (accumulated image Pr). There is no need to display this cross-section position information.

Furthermore, the designated-position information Vi is displayed in a display mode appropriate for the type of partial region Ui or the depth di of the partial region Ui. For example, the designated-position information V1, V2 that corresponds to cavities U1, U2 are displayed in blue, the designated-position information V3 that corresponds to the protruding part U3 is displayed in green, and the designated-position information V4 that corresponds to the peeled area U4 is displayed in pink.

[Actions and Advantageous Effects]

The actions and advantageous effects of such a fundus oculi observation device 20 are described.

This fundus oculi observation device 20 forms tomographic images Gi of a fundus oculi Ef and forms an accumulated image Pr based on the tomographic images Gi, and displays the tomographic image G and the accumulated image Pr side by side in the display 240A. Furthermore, in response to the examiner's designation of a partial region Ui of the tomographic image G, the fundus oculi observation device 20 acts so as to find the position in the accumulated image Pr corresponding to the partial region Ui and display the designated-position information Vi in the superimposed state on the accumulated image Pr.

According to the described fundus oculi observation device 20, the examiner can grasp of what site of the fundus oculi surface an attention site such as a lesion existing in the deep part of the fundus oculi is located in the deep part. Therefore, it is possible to grasp in detail the size, position and distribution state of the attention site.

Further, according to the fundus oculi observation device 20, when plural types of the partial regions Ui are designated, the device acts so as to display the designated-position information Vi in different display modes for the respective types of the partial regions Ui, so that it is possible to grasp in detail the states and positions of attention sites such as lesions of the fundus oculi Ef.

Further, according to the fundus oculi observation device 1, the device acts so as to detect the depth di of the designated partial region Ui in the tomographic image G and display the designated-position information Vi in a display mode appropriate for the depth di, so that it is possible to grasp in detail the state and position of an attention site such as a lesion of the fundus oculi Ef.

In addition, this fundus oculi observation device 20 further forms a 2-dimensional image of the surface of a fundus oculi Ef (fundus oculi image Ef') and conducts position alignment of an accumulated image Pr with respect to the fundus oculi image Ef'. Then, based on the result of the position alignment, the device acts so as to display the accumulated image Pr in the superimposed state on the fundus oculi image Ef and display the designated-position information Vi in the superimposed state on the accumulated image Pr.

The examiner is therefore able to grasp in detail the position of the accumulated image Pr in the fundus oculi Ef by observing the fundus oculi surface image composed of the fundus oculi image Ef' and the accumulated image Pr, and also grasp in detail the position in the fundus oculi Ef of an attention site corresponding to the designated-position information Vi displayed in the accumulated image Pr.

In the fundus oculi observation device related to this embodiment, in the case of not acquiring a fundus oculi image Ef', the constitution for acquiring the fundus oculi image Ef' is not required among the constitutions of the fundus oculi observation device 1 in the first embodiment. Therefore, the fundus oculi observation device can be composed of only an optical measurement device alone.

When the fundus oculi observation device related to the embodiment is configured by modifying the fundus oculi observation device 1 of the first embodiment, the "image forming part" comprises at least the retinal camera unit 1A for acquiring a tomographic image of a fundus oculi Ef, the OCT unit 150, the image forming part 220 (OCT image forming board 208*b*), and the image processor 230. When a constitution that is further capable of photographing a fundus oculi image Ef' is applied, the "image forming part" is constituted further including each part of the retinal camera unit 1A for photographing the fundus oculi image Ef'. The "display," "controller" and "designating part" are the same as in the above embodiment, respectively.

Third Embodiment

A fundus oculi observation device of a third embodiment related to the present invention is described. With the fundus oculi observation device 1, 20 (or the modification) of the first and second embodiments, the examiner observes tomographic images and manually designates an attention site such as a lesion. On the other hand, a fundus oculi observation device related to the third embodiment is characterized to function so that the lesion, etc. in a tomographic image can be extracted automatically.

The fundus oculi observation device of this embodiment has almost the same configuration as in the first and second embodiments. Specifically, the configurations shown in FIGS. 1 through 6 are the same in this embodiment. From hereon, for identical constitutional portions as in the first and second embodiments, the same reference numerals are given for the explanation.

[Device Configuration]

Figure 26:
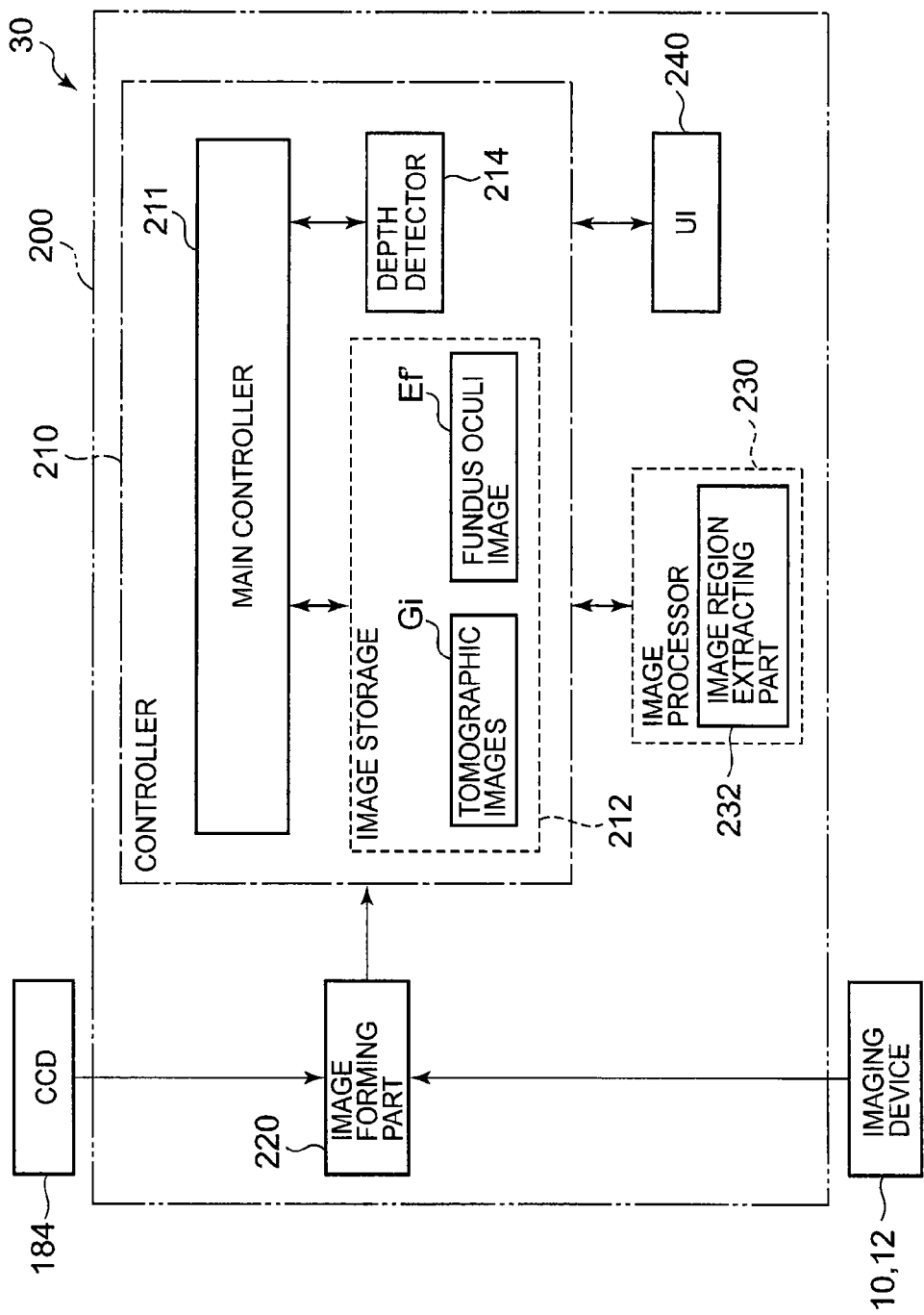
FIG. 26 is a schematic block diagram showing one example of the functional configuration of the arithmetic and control unit in the preferred embodiment of the fundus oculi observation device according to the present invention.

FIG. 26 shows one example of a constitution of an arithmetic control device 200 of a fundus oculi observation device 30 related to this embodiment. The fundus oculi observation device 30 shown in the same figure comprises an image-region extracting part 232 in the image processor 230.

The image-region extracting part 232 is for extracting a specific image region by analyzing a tomographic image, and functions as one example of the "extracting part" of the present invention. The "extracting part" is one example of the "designating part". The image-region extracting part 232 extracts a specific image region within a tomographic image, for example by analyzing the pixel value (brightness value) of the tomographic image.

An example of the specific image region subject to extraction is an image region equivalent to a cavity within a fundus oculi Ef, an image region equivalent to a protruding part such as a tumor, and an image region equivalent to a peeled area of a layer (refer to the first embodiment).

In the case of extraction of an image region equivalent to a cavity, information (cavity morphology information) related to the morphology of the cavity (such as size or shape of the cavity based on clinical data) is preliminarily stored in the image-region extracting part 232. The image region equivalent to the cavity of a fundus oculi Ef can be extracted from a tomographic image by analyzing the pixel value of the tomographic image and searching for an image region equivalent to the morphology indicated in the cavity morphological information.

In the case of extraction of an image region equivalent to a protruding part, information (protruding part morphological information) related to the morphology of a protruding part (such as size or shape of the protruding part based on clinical data) is preliminarily stored in the image-region extracting part 232. The image region equivalent to the protruding part of a fundus oculi Ef can be extracted from a tomographic image by analyzing the pixel value of the tomographic image and searching for an image region equivalent to the morphology indicated in the protruding part morphological information.

Moreover, in the case of extraction of the protruding part in a border position between layers, various layers within a tomographic image (e.g. inner plexform layer, photoreceptor layer, or retinal pigment epithelium) are specified and the shape of a region equivalent to the border between the layers is traced. Then, with regard to the region, the protruding part in the border position can be extracted by searching for the image region in a protrusion shape.

In the case of extraction of an image region equivalent to a peeled area, the image-region extracting part 232 specifies various kinds of layers within a tomographic image and searches for an area where there is a separation between the layers. This separated part is the peeled area.

[Usage Pattern]

Figure 27:
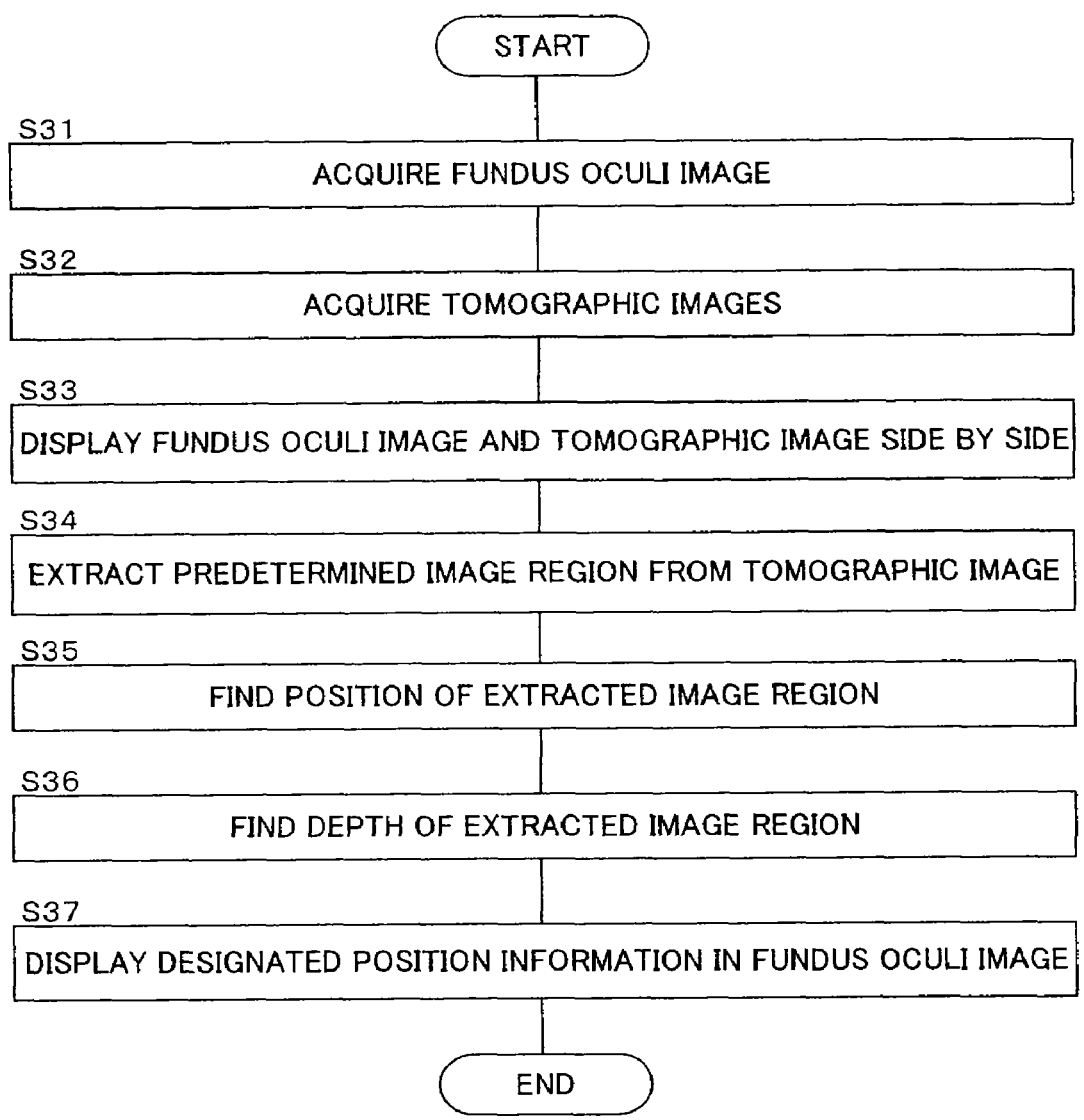
FIG. 27 is a flowchart showing one example of the usage pattern in the preferred embodiment of the fundus oculi observation device according to the present invention.

The usage pattern of the fundus oculi observation device 30 having the configuration as described above will be described. The flowchart in FIG. 27 shows one example of the usage pattern of the fundus oculi observation device 30.

First, a fundus oculi image Ef' and tomographic images Gi are acquired (S31, S32). The main controller 211 causes the image storage 212 to store the acquired fundus oculi image Ef' and the tomographic images Gi.

The main controller 211 causes the same fundus oculi observation screen 400 (ref. FIG. 11) as in the first embodiment to display the tomographic image G and the fundus oculi image Ef' (S33).

The image-region extracting part 232 analyzes the tomographic image G and extracts a specific image region such as a cavity, protruding part, peeled part, or the like (S34). The specific image region extracted by the image-region extracting part 232 may be an image region spreading 2-dimensionally, or a 1-dimensional linear image region, or an image region composed of a single point. Also, the image-region extracting part 232 is capable of extracting any number (one or more) of image regions (from hereon, ref. FIG. 12).

Next, the main controller 211 finds the position of each image region Ui (partial region of a tomographic image G) having been extracted (S35). The depth detector 214 finds the depth di of each image region Ui having been extracted (S36).

The main controller 211 acts so as to display the designated-position information Vi (ref. FIG. 13) indicating the position of each image region Ui within the fundus oculi image Ef' in the superimposed state on a fundus oculi image Ef', based on the position of each image region Ui obtained in Step S35 and the depth di of each image region Ui (S37).

The designated-position information Vi may be displayed in a display mode appropriate for the type of image region Ui. Then, the type of image region Ui can be specified based on the results of extraction of the image region Ui by the image-region extracting part 232. Moreover, the designated-position information Vi may be displayed in a display mode appropriate for the depth di of the image region Ui.

[Actions and Advantageous Effects]

The actions and advantageous effects of such a fundus oculi observation device 30 are described.

This fundus oculi observation device 30 forms a 2-dimensional image of the surface of a fundus oculi Ef (fundus oculi image Ef') and tomographic images Gi of the fundus oculi Ef, and causes the display 240A to display the fundus oculi image Ef' and the tomographic image G side by side. Furthermore, the fundus oculi observation device 30 acts so as to extract a partial region (a specific image region) Ui of the tomographic image G, find the position in the fundus oculi image Ef' that corresponds to the partial region Ui, and display the designated-position information Vi in the superimposed state on the fundus oculi image Ef'.

According to the described fundus oculi observation device 30, the examiner can grasp of what site of the fundus oculi surface an attention site such as a lesion existing in the deep part of the fundus oculi is located in the deep part. Therefore, it is possible to grasp in detail the size, position and distribution state of the attention site.

Moreover, according to this fundus oculi observation device 30, it is convenient because a partial region of a tomographic image equivalent to a lesion, etc. can be specified automatically. Specifically, even in cases where the examiner is not fully trained in observing tomographic images, they will still be able to specify a lesion, etc.

According to the present invention, because the constitution allows for a 2-dimensional image of the surface of a fundus oculi and a tomographic image of the fundus oculi to be displayed side-by-side while also displaying the designated-position information in an overlapping manner over the 2-dimensional image by obtaining the position in the 2-dimensional image that corresponds to a designated partial region of the tomographic image, an examiner is able to determine where lesions, etc. in the deep areas of the fundus oculi are located within the deep part of the fundus oculi surface. Therefore, it is possible to capture in detail the size, location, and distribution state of lesions, etc. of the fundus oculi.

Furthermore, the present invention is constituted so as to display a tomographic image and an accumulated image of a fundus oculi side-by-side and to display the designated-position information in an overlapping manner over the accumulated image by obtaining the position in the accumulated image that corresponds to a designated partial region of the tomographic image. The accumulated image is an image acquired by accumulating a plurality of tomographic images in a depth-wise direction of a fundus oculi and is an image representing the morphology of the fundus oculi surface. Therefore, because an examiner is able to determine where lesions, etc. in the deep part of a fundus oculi are located in the deep part of the fundus oculi surface, it is possible to capture in detail the size, location, and distribution state of lesions, etc. of the fundus oculi.

According to the present invention, because the constitution allows for the displaying of a tomographic image and a 3-dimensional image of a fundus oculi side-by-side and displays the designated-position information in an overlapping manner over the 3-dimensional image by obtaining the position in the 3-dimensional image that corresponds to a designated partial region of the tomographic image, an examiner is able to determine the 3-dimensional location of lesions, etc. present in the deep part of the fundus oculi. Therefore, it is possible to capture in detail the size, location, and distribution state of lesions, etc.

Modification

A modification of the fundus oculi observation device 30 related to this embodiment will be described.

Modification 1

Figure 28:
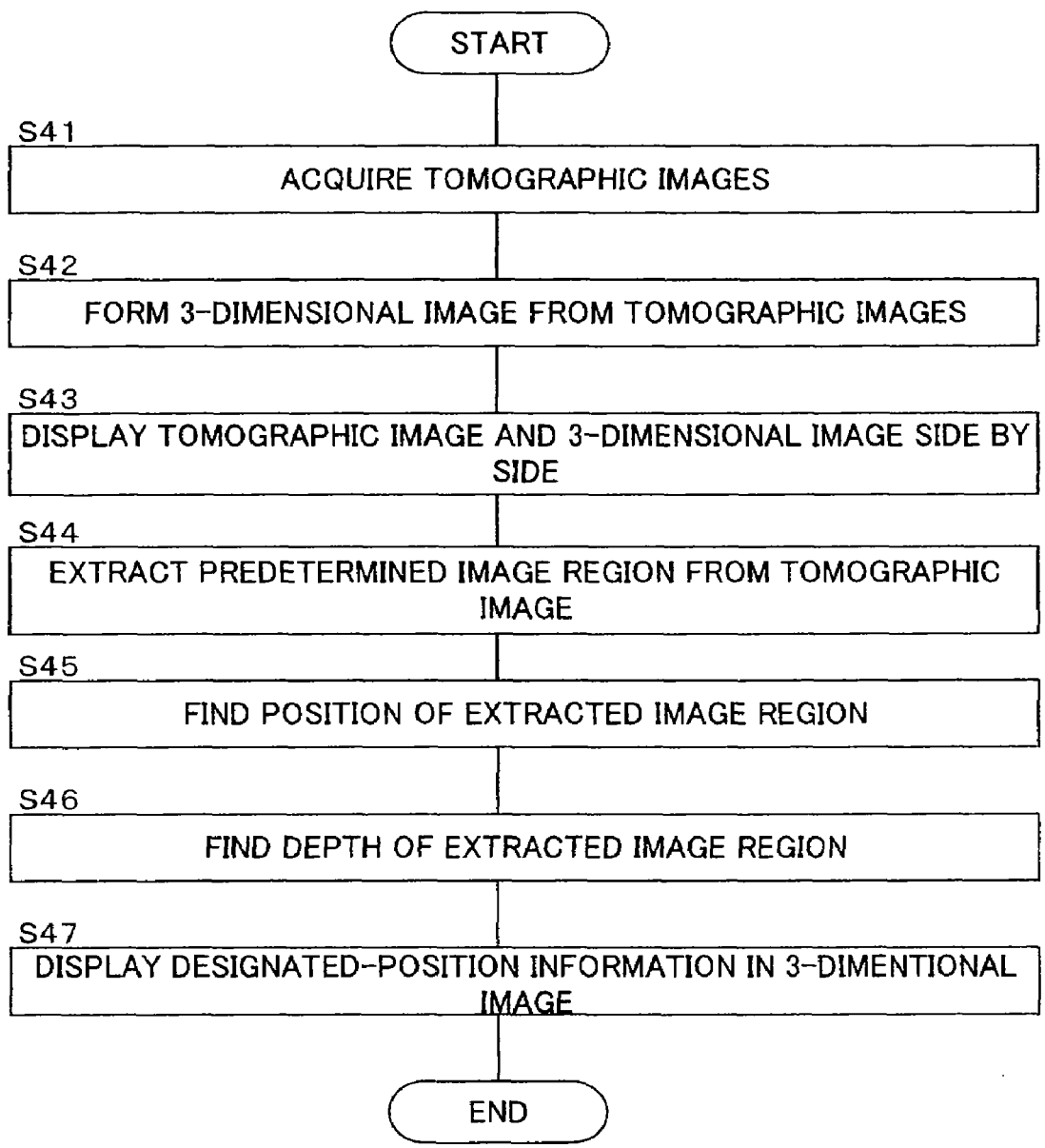
FIG. 28 is a flowchart showing one example of the usage pattern in the preferred embodiment of the fundus oculi observation device according to the present invention.

In the above third embodiment, the designated-position information that corresponds to the partial region of the tomographic image G is displayed in the fundus oculi image Ef', but the same designated-position information may be displayed so as to be superimposed on a 3-dimensional image. One example of the usage pattern is described below (ref. flow chart in FIG. 28, FIG. 15, FIG. 16).

First, tomographic images Gi are acquired (S41). The image processor 230 forms a 3-dimensional image H of a fundus oculi Ef based on the acquired tomographic images Gi (S42). The main controller 211 causes the image storage 212 to store (image data of) the tomographic images Gi and 3-dimensional image H.

The main controller 211 causes a fundus oculi observation screen 500 as in FIG. 15 to display the tomographic image G and the 3-dimensional image H (S43).

The image-region extracting part 232 extracts a specific image region Ui such as a cavity, protruding part, or peeled area by analyzing the tomographic image G (S44). The main controller 211 finds the position of each image region Ui that has been extracted (S45).

Next, the depth detector 214 finds the depth di of each image region Ui that has been extracted (S46). The main controller 211 acts so as to display the designated-position information Vi (ref. FIG. 16) indicating the position of each image region Ui within the 3-dimensional image H in the superimposed state on the 3-dimensional image H, based on the position of each image region Ui obtained in step S44 and the depth di of each image region Ui (S47).

Then, the main controller 211 acts so as to display the 3-dimensional image H in a half-transparent state so that the designated-position information Vi positioned inside the 3-dimensional image H can be seen through.

According to the modification 1, the examiner is able to grasp the 3-dimensional position of a lesion, etc. present in the deep part of a fundus oculi by visually checking the designated-position information Vi. Therefore, it is possible to grasp in detail the size, location, distribution state, etc. of a lesion, etc. Furthermore, it is convenient because a partial region of a tomographic image equivalent to a lesion, etc. can be specified automatically.

Also in this modification example, the designated-position information Vi may be displayed in a display mode appropriate for the type of image region Ui or the depth di.

Furthermore, it is possible to form a tomographic image in any cross-section of a 3-dimensional image H, and properly display the tomographic image of a cross-section crossing the image region of the designated-position information Vi positioned inside the 3-dimensional image H or a peripheral region thereof.

In the fundus oculi observation device used for the usage pattern related to this modification, a constitution for forming the fundus oculi image Ef' is not required among constitutions of the fundus oculi observation device 30 in the above embodiment. Therefore, the fundus oculi observation device can be composed of only an optical image measurement device.

Modification 2

Figure 29:
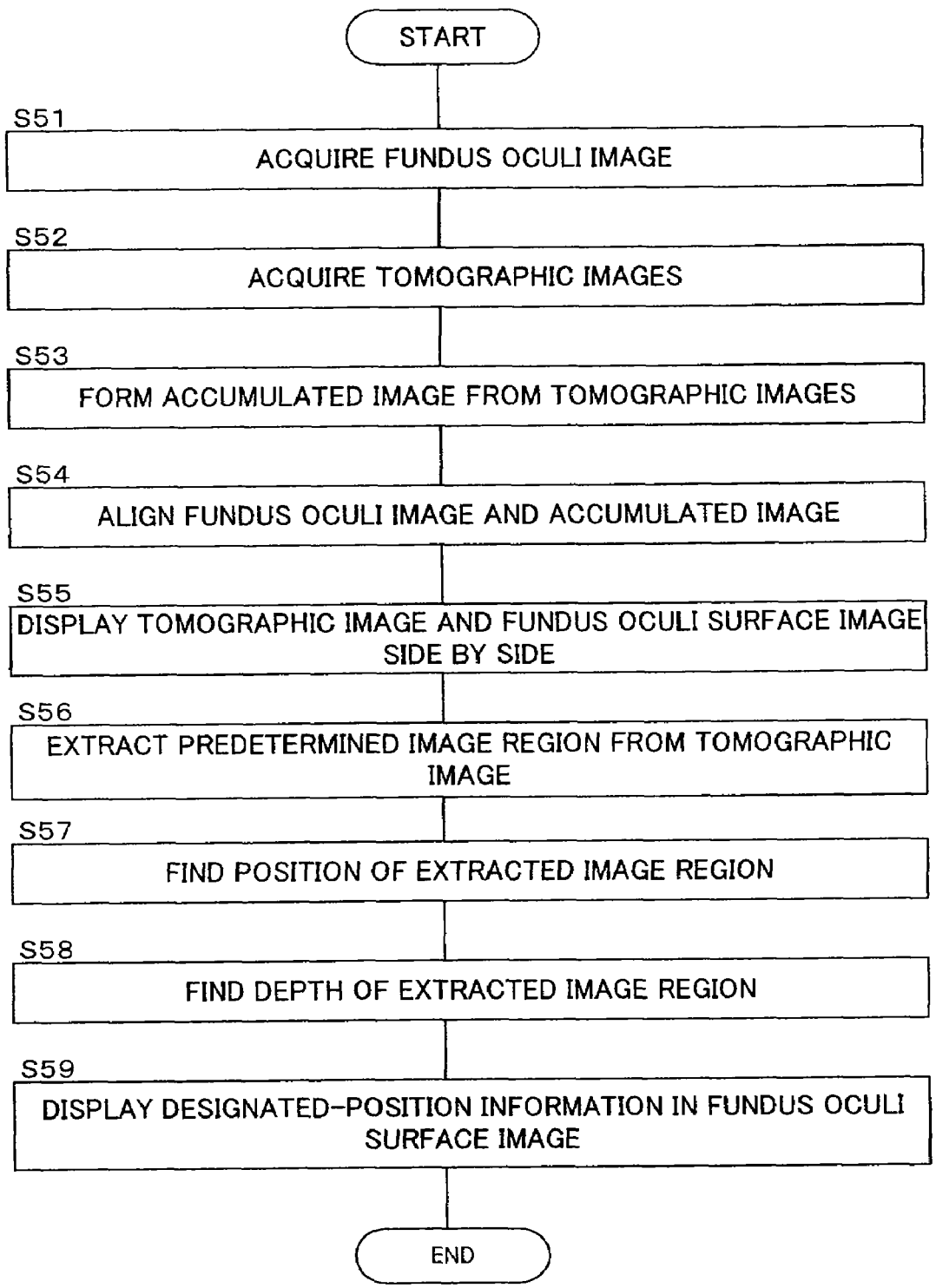
FIG. 29 is a flowchart showing one example of the usage pattern in the preferred embodiment of the fundus oculi observation device according to the present invention.

The same designated-position information as in the above third embodiment may be displayed in the superimposed state on an accumulated image (ref. second embodiment). The fundus oculi observation device in this modification further comprises the depth detector 214, the position alignment part 215, and the accumulated image forming part 231 as described in the second embodiment. One example of the usage pattern of the fundus oculi observation device in this modification example 2 is described below (flowchart in FIG. 29, FIG. 24, and FIG. 25).

First, a fundus oculi image Ef and tomographic images Gi are acquired (S51, S52). The accumulated image forming part forms an accumulated image Pr of a fundus oculi Ef based on the acquired tomographic images Gi (S53). The main controller 211 causes the image storage 212 to store (image data of) the fundus oculi image Ef, tomographic images Gi, and accumulated image Pr.

The position alignment part 215 conducts position alignment of the accumulated image Pr with respect to the fundus oculi image Ef (S54). The main controller 211 causes a fundus oculi observation screen 600 in FIG. 24 to display a tomographic image G and a fundus oculi surface image (fundus oculi image Ef into which an accumulated image Pr has been embedded) (S55).

The image-region extracting part 232 analyzes the tomographic image G and extracts a specific image region Ui such as a cavity, protruding part, or a peeled area (S56). The main controller 211 finds the position of each image region Ui that has been extracted (S57).

Next, the depth detector 214 finds the depth di of each image region Ui that has been extracted (S58). The main controller 211 acts so as to display the designated-position information Vi indicating the position of each image region Ui within the fundus oculi surface image (accumulated image Pr) in the superimposed state on the fundus oculi surface image, based on the position and depth di of each image region Ui (S59). Then, each designated-position information Vi is displayed in the accumulated image Pr within the fundus oculi surface image (ref. FIG. 25).

According to this modification 2, the examiner can grasp of what site of the fundus oculi surface a lesion, etc. existing in the deep part of a fundus oculi is located within the deep part. Therefore, it is possible to grasp in detail the size, location, the distribution state, etc. of an attention site. Furthermore, it is convenient because a partial region of a tomographic image equivalent to a lesion, etc. can be specified automatically.

Also in this modification, the designated-position information Vi may be displayed in a display mode appropriate for the type of image region Ui or the depth di.

[Fundus Oculi Image Display Device]

A fundus oculi image display device according to the present invention will be explained. Incidentally, in the embodiments above, the arithmetic and control unit 200 is employed as the fundus oculi image display device.

A first fundus oculi image display device related to the present invention comprises a storage (image storage 212; ref. FIG. 7) for storing (image data) of a 2-dimensional image of the surface of a fundus oculi (fundus oculi image Ef) and tomographic images Gi.

Furthermore, the first fundus oculi image display device comprises a display (display 240A), and a controller for causing the display to display the fundus oculi image Ef and the tomographic image G stored in the storage side by side. When displaying a tomographic image G other than the tomographic images Gi, the tomographic image G is formed by the image processor 230 based on a 3-dimensional image based on the tomographic images Gi or the like. The tomographic image G that has been formed is stored in the storage.

When a partial region of the tomographic image G is designated by the designating part, the controller functions so as to obtain the position in the fundus oculi image Ef corresponding to this partial region and display the designated-position information in the superimposed state on the position of the fundus oculi image Ef.

According to the first fundus oculi observation device, the examiner can grasp of what site of the fundus oculi surface an attention site such as a lesion existing in the deep part of the fundus oculi is located in the deep part. Therefore, it is possible to grasp in detail the size, position and distribution state of the attention site.

A second fundus oculi image display device related to the present invention comprises: a storage for storing a plurality of tomographic images Gi of a fundus oculi and an accumulated image Pr obtained by accumulating the respective tomographic images Gi in a depth direction; a display; and a controller for causing the display to display the tomographic image G stored in the storage and the accumulated image Pr side by side. Herein, a fundus oculi image Ef into which the accumulated image Pr has been embedded (fundus oculi surface image) may also be displayed along with the tomographic image G.

When a partial region of the tomographic image G is designated by the designating part, the controller functions so as to find the position in the accumulated image Pr that corresponds to this partial region and display the designated-position information in the superimposed state on the position of the accumulated image Pr.

According to this fundus oculi observation device, the examiner can grasp of what site of the fundus oculi surface an attention site such as a lesion existing in the deep part of the fundus oculi is located in the deep part. Therefore, it is possible to grasp in detail the size, position and distribution state of the attention site.

A third fundus oculi image display device related to the present invention comprises: a storage for storing a plurality of tomographic images Gi of a fundus oculi and a 3-dimensional image H based on these tomographic images Gi; a display; and a controller for causing the display to display the tomographic images G stored in the storage and the 3-dimensional image H side by side.

When a partial region of the tomographic image G is designated by the designating part, the controller functions so as to find the position in the 3-dimensional image H that corresponds to this partial region and display the designated-position information in the superimposed state on the position of the 3-dimensional image H.

According to this fundus oculi observation device, the examiner can grasp the 3-dimensional position of an attention site such as a lesion existing in the deep part of the fundus oculi. Therefore, it is possible to grasp in detail the size, position and distribution state of the attention site.

It is possible to dispose any function disposed to the first to third fundus oculi observation devices to the first through third fundus oculi image display devices. Specifically, the designating part may be an operating part for the examiner to designate a partial region of a tomographic image, or may be an extracting part for extracting a specific image region by analyzing the tomographic image.

[Program]

A program configured to control the device according to the present invention will be explained hereunder. In the above embodiments, the control program 204a is equivalent to the program.

The program configured to control the device according to the present invention is a computer program for causing a computer comprising a storage, a display, a controller and a designating part to function as the above fundus oculi image display device.

The program configured to control the device according to the present invention can be recorded in any recording medium readable by a drive of the computer. For example, a recording medium such as an optical disk, a magneto-optical disk (CD-ROM, DVD-ROM, DVD-ROM, MO, etc.) and a magnetic storage medium (hard disk, Floppy Disk™, ZIP, etc.) can be used. Moreover, it is also possible to store the program in a storage device such as a hard disk drive or a memory. Furthermore, it is also possible to transmit the program via a network such as the Internet and a LAN.

[Modification or the Like]

The fundus oculi observation device, the fundus oculi image display device, and the program that are described above are merely specific examples for favorably implementing the present invention. Therefore, it is possible to properly make any modification within the scope and intent of the present invention.

Figure 30:
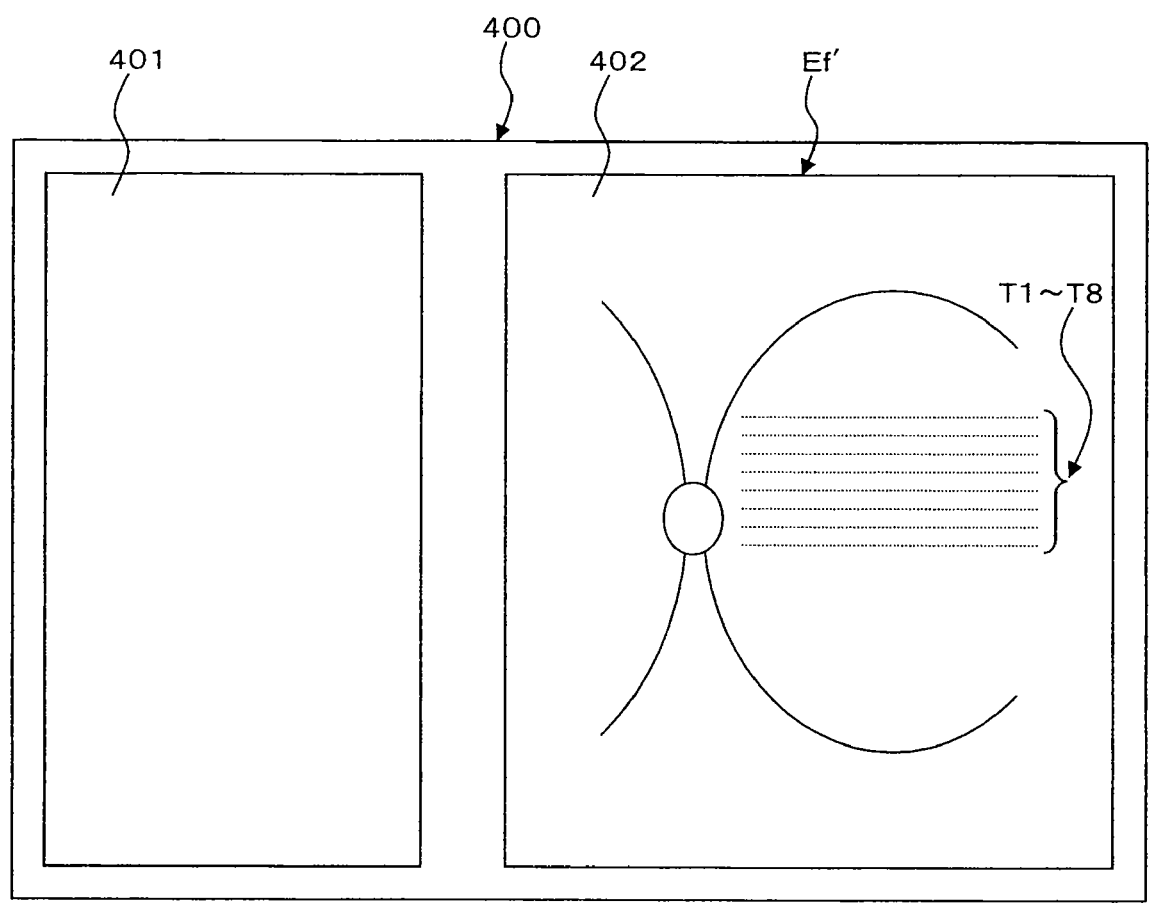
FIG. 30 is a schematic diagram showing one example of a display screen displayed in a modification of the preferred embodiment of the fundus oculi observation device according to the present invention.

FIGS. 30 through 35 show a usage example of the above fundus oculi observation device. As shown in FIG. 30, this usage example is used at the time of observation of tomographic images based on a plurality of (eight, herein) scanning lines. The reference numerals T1 through T8 denote cross-section position information indicating the cross-sectional positions of eight tomographic images. Herein, the cross-section information is denoted by reference numerals T1, T2 . . . T8 in the order from the upper part of the fundus oculi observation screen 400. The cross-sectional positions of these tomographic images are arranged in parallel along the y-direction. For example, the examiner can operate the operating part 240B, thereby selectively displaying a desired one of the eight tomographic images. When a tomographic image is selected, the selected tomographic image and a fundus oculi image Ef' are displayed side by side, and only the cross-section position information of the selected tomographic image is displayed in the fundus oculi image Ef' (consequently, it is possible to grasp what cross-sectional position in the fundus oculi image Ef' an observed tomographic image is located).

Figure 31:
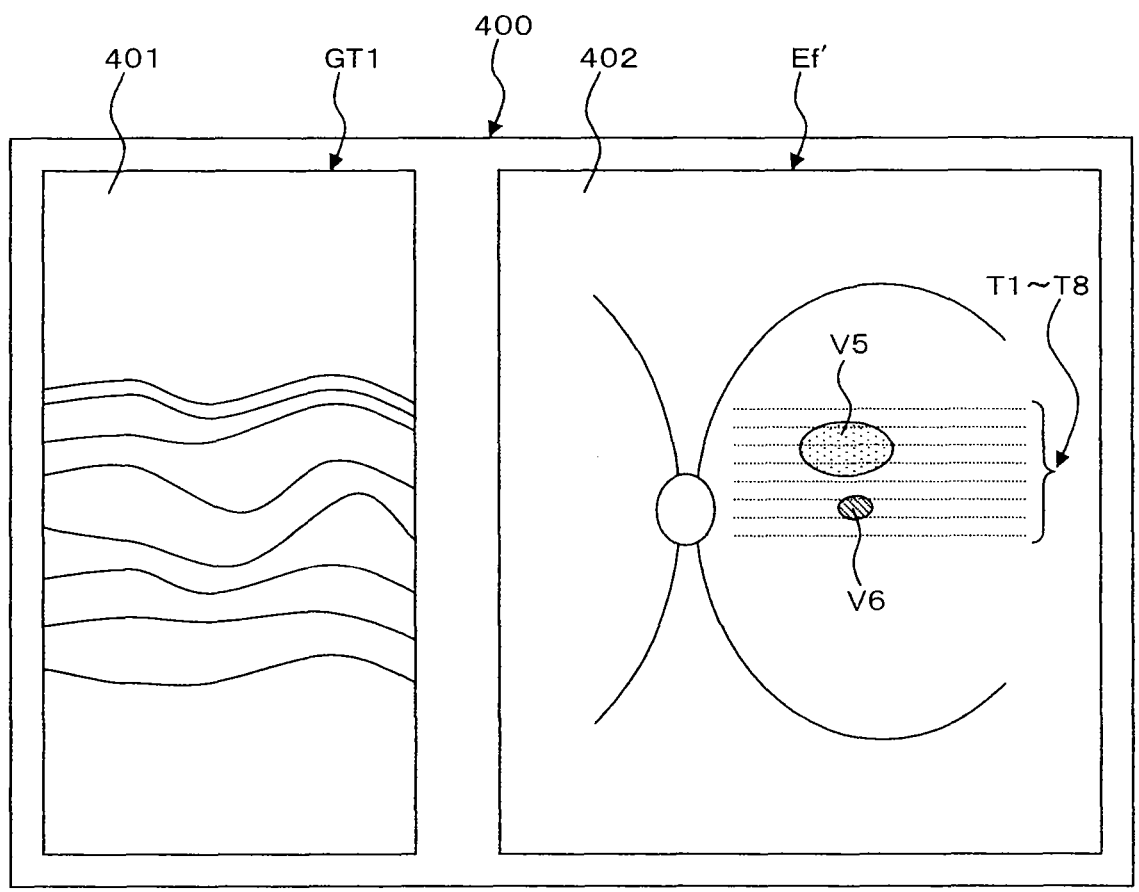
FIG. 31 is a schematic diagram showing one example of a display screen displayed in a modification of the preferred embodiment of the fundus oculi observation device according to the present invention.

FIG. 31 shows a state in which a tomographic image GT1 at a cross-sectional position indicated by the cross-section position information T1 is displayed along with the fundus oculi image Ef'. Herein, it is assumed that a partial region of the tomographic image has been already designated (or extracted). In the fundus oculi image Ef' of FIG. 31, designated-position information V5, V6 corresponding to the partial regions of the tomographic image are displayed. In this usage example, as shown in FIG. 31, the cross-section position information T2, T3, T4 are crossed with the designated-position information V5, and the cross-section position information T6 and T7 are crossed with the designated-position information V6. As for the tomographic image GT1 shown in FIG. 31, the cross-sectional position is not crossed with the designated-position information V5, V6, and the partial regions corresponding to the designated-position information V5, V6 are not displayed.

Figure 32A:
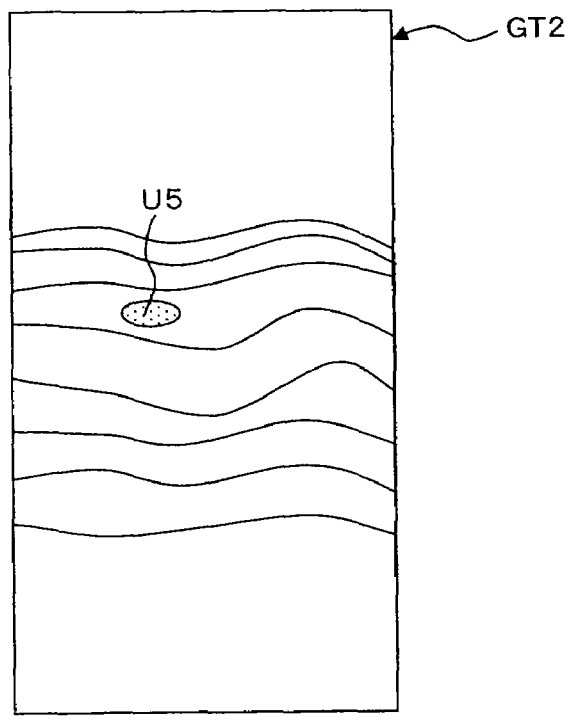
FIG. 32 is a schematic diagram showing one example of a display screen displayed in a modification of the preferred embodiment of the fundus oculi observation device according to the present invention.

FIG. 32A shows a tomographic image GT2 at a cross-sectional position indicated by the cross-section position information T2 displayed side by side with the fundus oculi image Ef'. Also in this case, the designated-position information V5, V6 are displayed in the fundus oculi image Ef'. Furthermore, a partial region U5 that corresponds to the designated-position information V5 is displayed in the tomographic image GT2. The partial region U5 represents a cross section of a lesion, etc. indicated by the designated-position information V5 at the cross-sectional position indicated by the cross-section position information T2.

Figure 32B:
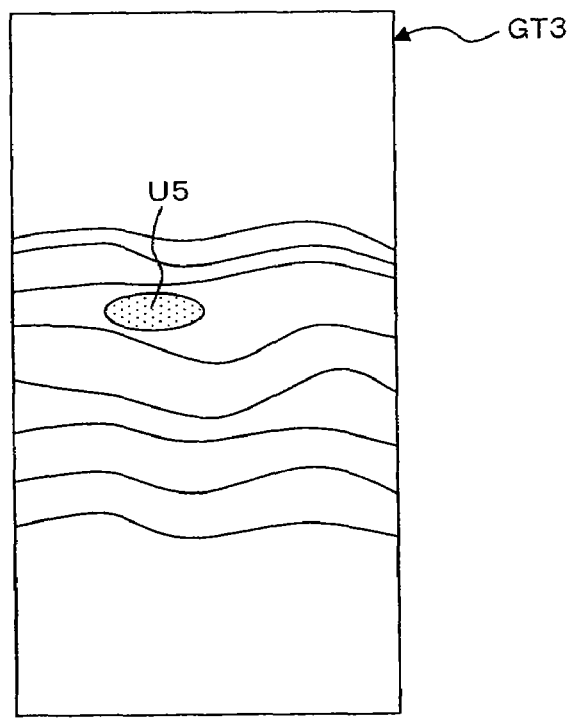

FIG. 32B shows a tomographic image GT3 at a cross-sectional position indicated by the cross-section position information T3 displayed side by side with the fundus oculi image Ef'. Also in this case, the designated-position information V5, V6 are displayed in the fundus oculi image Ef', and a partial region U5 that corresponds to the designated-position information V5 is displayed in the tomographic image GT3. The partial region U5 represents the cross section of a lesion, etc. indicated by the designated-position information V5 at the cross-sectional position indicated by the cross-section position information T3.

Figure 33A:
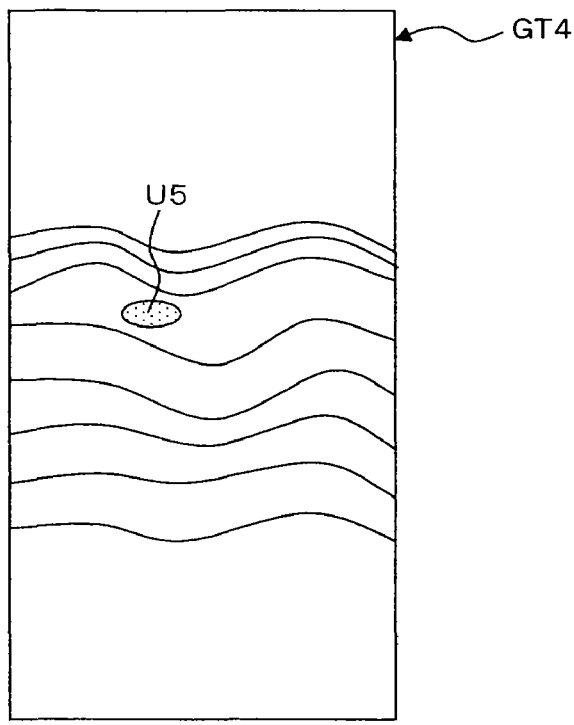
FIG. 33 is a schematic diagram showing one example of a display screen displayed in a modification of the preferred embodiment of the fundus oculi observation device according to the present invention.

FIG. 33A shows a tomographic image GT4 at a cross-sectional position indicated by the cross-section position information T4 displayed side by side with the fundus oculi image Ef'. Also in this case, the designated-position information V5, V6 are displayed in the fundus oculi image Ef', and a partial region U5 that corresponds to the designated-position information V5 is displayed in the tomographic image GT4. The partial region U5 represents the cross-section of a lesion, etc. indicated by the designated-position information V5 at the cross-sectional position indicated by the cross-section position information T4.

Figure 33B:
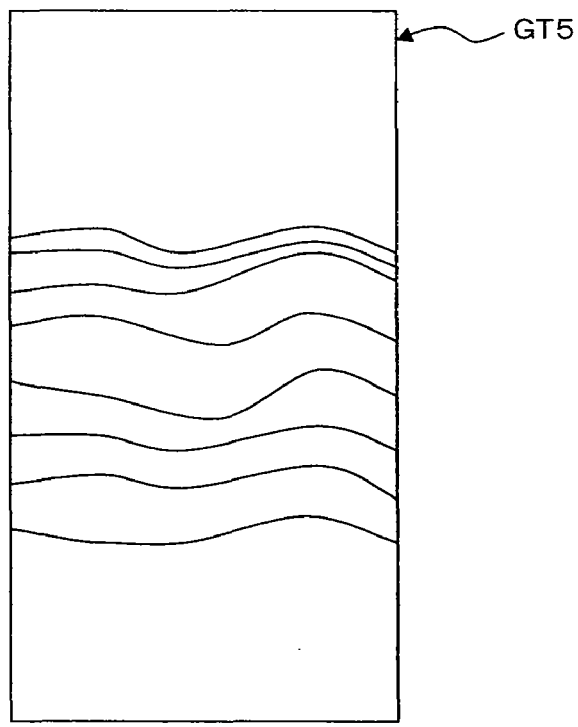

FIG. 33B shows a tomographic image GT5 at a cross-sectional position indicated by the cross-section position information T5 displayed side by side with the fundus oculi image Ef. Also in this case, the designated-position information V5, V6 are displayed in the fundus oculi image Ef'. Furthermore, as previously described, because the cross-sectional position indicated by the cross-sectional information T5 is not crossed with the designated-position information V5, V6, and the partial region indicating a lesion, etc. is not displayed in the tomographic image GT5.

Figure 34A:
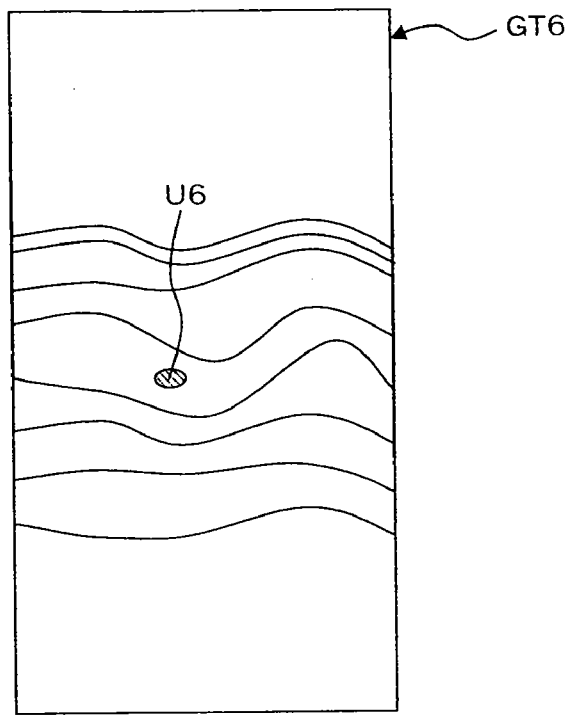
FIG. 34 is a schematic diagram showing one example of a display screen displayed in a modification of the preferred embodiment of the fundus oculi observation device according to the present invention.

FIG. 34A shows a tomographic image GT6 at a cross-sectional position indicated by the cross-section position information T6 displayed side by side with the fundus oculi image Ef'. Also in this case, the designated-position information V5, V6 are displayed in the fundus oculi image Ef'. Furthermore, a partial region U6 that corresponds to the designated-position information V6 is displayed in the tomographic image GT6. The partial region U6 represents the cross-section of a lesion, etc. indicated by the designated-position information V6 at the cross-sectional position indicated by the cross-section position information T6.

Figure 34B:
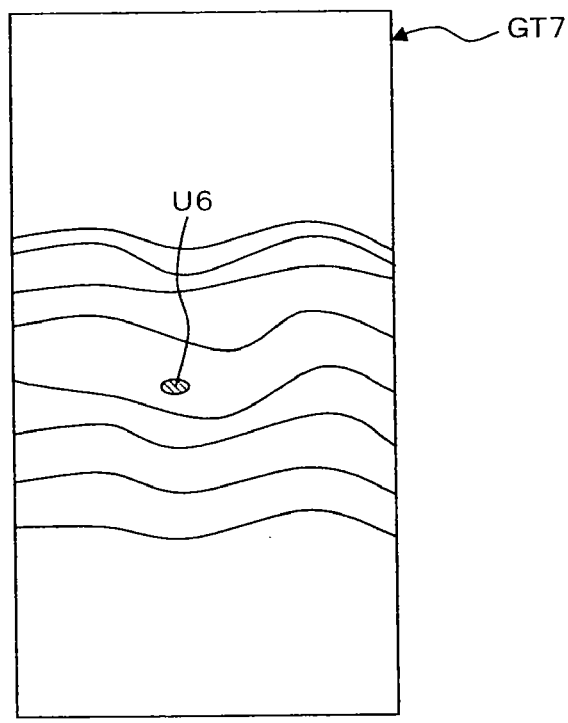

FIG. 34B shows a tomographic image GT7 at a cross-sectional position indicated by the cross-section position information T7 displayed side by side with the fundus oculi image Ef'. Also in this case, the designated-position information V5, V6 are displayed in the fundus oculi image Ef', and a partial region U6 that corresponds to the designated-position information V6 is displayed in the tomographic image GT7. The partial region U6 represents the cross-section of a lesion, etc. indicated by the designated-position information V6 at the cross-sectional position indicated by the cross-section position information T7.

Figure 35:
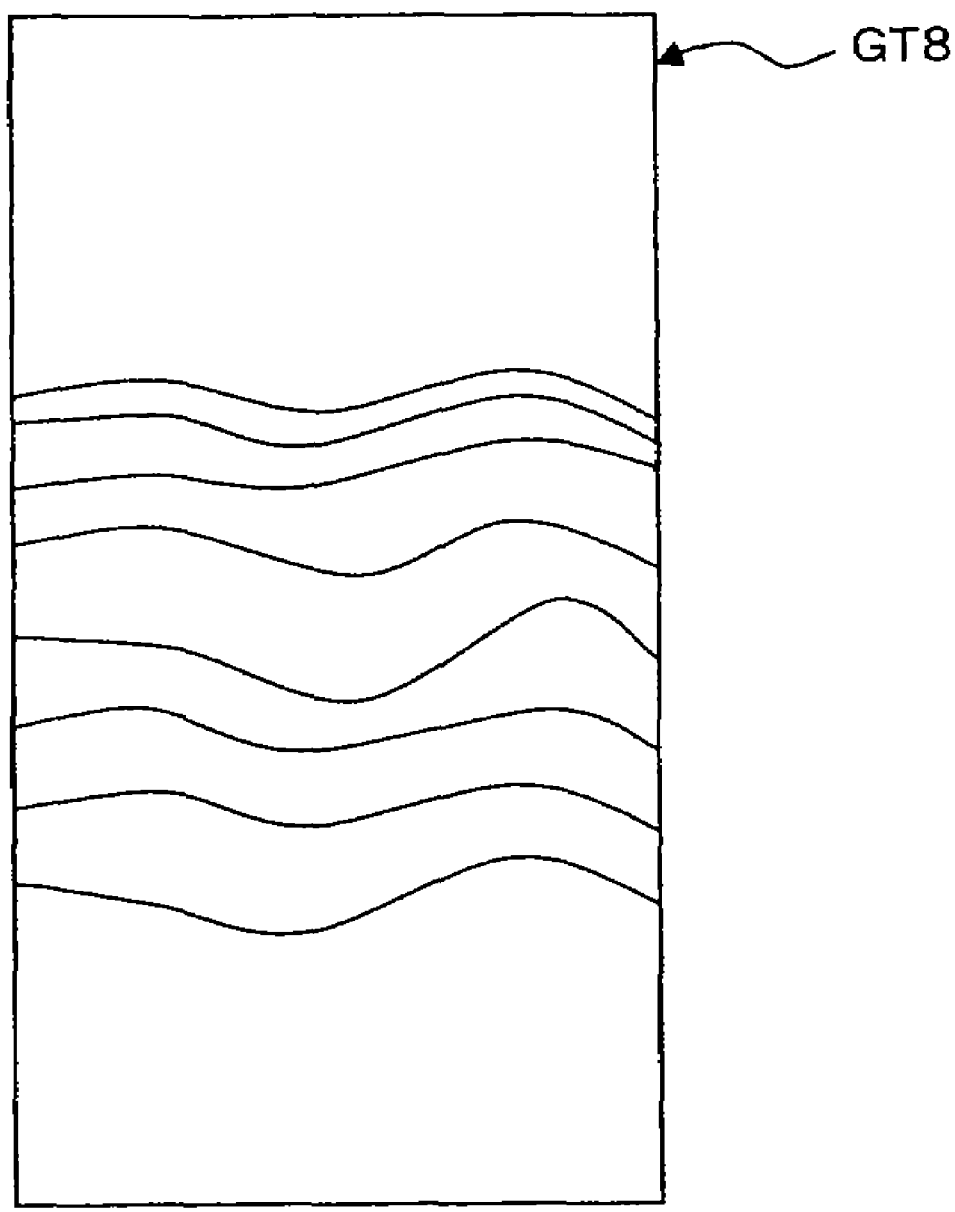
FIG. 35 is a schematic diagram showing one example of a display screen displayed in a modification of the preferred embodiment of the fundus oculi observation device according to the present invention.

FIG. 35 shows a tomographic image GT8 at a cross-sectional position indicated by the cross-section positional information T8 displayed side by side with the fundus oculi image Ef'. Also in this case, the designated-position information V5, V6 are displayed in the fundus oculi image Ef'. Furthermore, as previously described, because the cross-sectional position indicated by the cross-sectional information T8 is not crossed with the designated-position information V5, V6, the partial region indicating a lesion, etc. is not displayed in the tomographic image GT8.

Thus, it is possible to observe various portions of an attention site such as a lesion by observing tomographic images and a fundus oculi image Ef' while changing the cross-sectional position, so that the examiner can grasp in detail the state and location of the area of a lesion, etc. of a fundus oculi.

This usage example can also be applied to any case other than a case where a plurality of cross-sectional positions are arranged in parallel as described above: for example, cross-sectional positions are arranged concentrically, arranged spirally, arranged in vertical and horizontal directions, and arranged randomly.

Moreover, one tomographic image is displayed with a fundus oculi image Ef' in the above description, but it is also possible to display two or more tomographic images along with the fundus oculi image Ef'.

This usage example can also be applied not only a case of displaying a fundus oculi image Ef' and a tomographic image side by side, but also a case of displaying a 3-dimensional image and a tomographic image of a fundus oculi Ef side by side, or a case of displaying an accumulated image and a tomographic image side by side.

Moreover, the fundus oculi observation devices of the above embodiments are configured so as to contain a Fourier domain OCT device, but the configuration of the present invention can also be applied to a time domain OCT device. Incidentally, a time domain OCT device is described, for example, such as in Japanese Unexamined Patent Application Publication 2005-241464 filed by the present applicant. Moreover, it is also possible to use an OCT device of any other type such as a swept source type.

What is claimed is:

1. A fundus oculi observation device comprising:
a first image forming part configured to optically acquire data and form a 2-dimensional image of a surface of a fundus oculi of an eye based on the data;
a second image forming part configured to optically acquire data and form a tomographic image of the fundus oculi based on the data;
a display;
a control means for controlling the display to display the 2-dimensional image and the tomographic image side by side; and
a designating means for designating a lesion as a partial region on the displayed tomographic image,
wherein the control means determines a corresponding position of the designated partial region of the tomographic image on the 2-dimensional image which is seen from the anterior side of the eye, and causes the display to display designated-position information of the determined position of the designated partial region within the 2-dimensional image, together with the 2-dimensional image.

2. The fundus oculi observation device according to claim 1, wherein:
the designating means includes an operating part configured for an examiner to designate the partial region of the tomographic image.

3. The fundus oculi observation device according to claim 1, wherein:
the designating means includes an extracting part configured to analyze the displayed tomographic image and extract a specific image region, and designates the extracted specific image region as the partial region.

4. The fundus oculi observation device according to claim 1, wherein:
when plural types of partial regions are designated by the designating means, the control means displays the designated-position information in different display modes for each of the plural types.

5. The fundus oculi observation device according to claim 1, wherein:
the control means includes a depth detector configured to detect a depth in the tomographic image of the partial region designated by the designating means, and displays the designated-position information in a display mode appropriate for the detected depth.

6. A fundus oculi observation device comprising:
an image forming part configured to optically acquire data, form a plurality of tomographic images of a fundus oculi of an eye based on the data, accumulate the plurality of tomographic images in a depth direction, and form an accumulated image of the fundus oculi;
a display;
a control means for controlling the display to display one or more of the tomographic images and the accumulated image side by side; and
a designating means for designating a lesion as a partial region on the displayed tomographic image,
wherein the control means determines a corresponding position of the designated partial region of the tomographic image on the accumulated image which is seen from the anterior side of the eye, and causes the display to display designated-position information of the determined position of the designated partial region within the accumulated image, together with the accumulated image.

7. The fundus oculi observation device according to claim 6, wherein:
the image forming part optically acquires data and, based on the data, forms a 2-dimensional image of the surface of the fundus oculi including a region equivalent to the accumulated image;
the means includes a position alignment means for performing position alignment of the accumulated image with respect to the 2-dimensional image; and
the control means displays the accumulated image in a superimposed state on the 2-dimensional image based on the result of the position alignment, and displays the designated-position information in a superimposed state on the accumulated image.

8. The fundus oculi observation device according to claim 6, wherein:
the designating means includes an operating part configured for an examiner to designate partial regions of the tomographic images.

9. The fundus oculi observation device according to claim 6, wherein:
the designating means includes an extracting part configured to analyze the displayed tomographic image and extract a specific image region, and designates the extracted specific image region as the partial region.

10. The fundus oculi observation device according to claim 6, wherein:
when plural types of partial regions are designated by the designating means, the control means displays the designated-position information in different display modes for each of the plural types.

11. The fundus oculi observation device according to claim 6, wherein:
the control means includes a depth detector configured to detect a depth in the displayed tomographic image of the partial region designated by the designating means, and displays the designated-position information in a display mode appropriate for the detected depth.

12. A fundus oculi observation device comprising:
an image forming part configured to optically acquire data, form a plurality of tomographic images of a fundus oculi of an eye based on the data, and form a 3-dimensional image of the fundus oculi based on the plurality of tomographic images;
a display;
a control means for controlling the display to display one or more of the tomographic images and the 3-dimensional image side by side; and
a designating means for designating a lesion as a partial region on the displayed tomographic image,
wherein the control means determines a corresponding position of the designated partial region on the 3-dimensional image which is seen from the anterior side of the eye, and causes the display to display designated-position information of the determined position of the designated partial region within the 3-dimensional image, together with the 3-dimensional image.

13. The fundus oculi observation device according to claim 12, wherein:
the designating means includes an operating part configured for an examiner to designate partial regions of the tomographic images.

14. The fundus oculi observation device according to claim 12, wherein:
the designating means includes an extracting part configured to analyze the displayed tomographic image and extract a specific image region, and designates the extracted specific image region as the partial region.

15. The fundus oculi observation device according to claim 12, wherein:
when plural types of partial regions are designated by the designating means, the control means displays the designated-position information in different display modes for each of the plural types.

16. The fundus oculi observation device according to claim 12, wherein:
the control means includes a depth detector configured to detect a depth in the displayed tomographic image of the partial region designated by the designating means, and displays the designated-position information in a display mode appropriate for the detected depth.

17. A fundus oculi image display device comprising:
a storage configured to store an image representing a surface of a fundus oculi of an eye and a tomographic image of the fundus oculi;
a display;
a control means for controlling the display to display the image representing the surface of the fundus oculi and the tomographic image side by side; and
a designating means for designating a lesion as a partial region on the displayed tomographic image,
wherein the control means determines a corresponding position of the designated partial region within the image representing the surface of the fundus oculi which is seen from the anterior side of the eye, and causes the display to display designated-position information of the determined position of the designated partial region within the image representing the surface of the fundus oculi, together with the image representing the surface of the fundus oculi.

18. The fundus oculi image display device according to claim 17, wherein:
the storage stores a 2-dimensional image acquired by photographing the surface of the fundus oculi as the image representing the surface of the fundus oculi.

19. The fundus oculi image display device according to claim 17, wherein:
the storage stores a plurality of the tomographic images, and further stores an accumulated image of the fundus oculi obtained by accumulating the plurality of tomographic images in the depth direction as the image representing the surface of the fundus oculi.

20. A fundus oculi image display device comprising:
a storage configured to store a plurality of tomographic images of a fundus oculi of an eye and a 3-dimensional image of the fundus oculi based on the plurality of tomographic images;
a display;
a control means for controlling the display to display the tomographic images and the 3-dimensional image side by side; and
a designating means for designating a lesion and a partial region on the displayed tomographic image,
wherein the control means determines a corresponding position of the designated partial region within the 3-dimensional image which is seen from the anterior side of the eye, and causes the display to display designated-position information of the determined position of the designated partial region within the 3-dimensional image, together with the 3-dimensional image.

* * * * *